(12) United States Patent  (10) Patent No.: US 8,678,979 B2
Stark et al.  (45) Date of Patent: Mar. 25, 2014

(54) REMOTE MONITORING OF A PATIENT

(75) Inventors: John G. Stark, Excelsior, MN (US);
Duane P. M. Oyen, Maple Grove, MN (US); Thomas Bybee, Ramsey, MN (US); Arthur M. Lohmann, Minnetonka, MN (US); Joel L. Boyd, Eden Prairie, MN (US)

(73) Assignee: IZEX Technologies, Inc., Minneapolis, MN (US)

( * ) Notice: Subject to any disclaimer, the term of this patent is extended or adjusted under 35 U.S.C. 154(b) by 996 days.

(21) Appl. No.: 11/714,669

(22) Filed: Mar. 6, 2007

(65) Prior Publication Data

US 2007/0155588 A1 Jul. 5, 2007

Related U.S. Application Data

(63) Continuation of application No. 11/017,593, filed on Dec. 20, 2004, now abandoned, which is a continuation of application No. 09/382,433, filed on Aug. 25, 1999, now Pat. No. 6,872,187.

(60) Provisional application No. 60/098,779, filed on Sep. 1, 1998.

(51) Int. Cl.
*A63B 71/00* (2006.01)
*A61B 5/103* (2006.01)
*A61B 5/117* (2006.01)

(52) U.S. Cl.
USPC .................................. 482/8; 482/9; 600/595

(58) Field of Classification Search
USPC ............ 705/2, 3; 600/301, 595, 300, 500, 59;
128/904, 903, 920; 482/51, 4, 5, 8, 9, 482/44, 115, 116, 139; 602/16, 23, 26
See application file for complete search history.

(56) References Cited

U.S. PATENT DOCUMENTS 2,693,796 A 11/1954 Warner
2,777,439 A 1/1957 Tuttle
(Continued)

FOREIGN PATENT DOCUMENTS

EP 173161 A1 3/1986
EP 4815469 3/1989
(Continued)

OTHER PUBLICATIONS

"Put Your Patient's Recovery Steps Ahead with the Sutter CPM™ 9000," by Sutter Biomedical Inc., SUT 133, V85, Jan. 1985, pp. 1-6.
(Continued)

*Primary Examiner* — Oren Ginsberg
(74) *Attorney, Agent, or Firm* — Schwegman Lundberg & Woessner, P.A.

(57) ABSTRACT

Orthoses with microprocessor control placed around the joint of a patient are used to perform and to monitor isometric, range-of-motion, proprioception and isotonic exercises of the joint. A variety of improved hardware elements result in an orthosis that is easier to use and interacts more efficiently with the controller to allow the monitoring of a greater range of motions while holding down cost and provide suitable accurate evaluation of the exercises. Efficient ways of programming the exercises, monitoring the exercises and evaluating the exercise provide a comprehensive program for the rehabilitation of an injured or weakened joint.

19 Claims, 20 Drawing Sheets

(56) References Cited

U.S. PATENT DOCUMENTS

| | | |
|---|---|---|
| 2,832,334 A | 4/1958 | Whitelaw |
| 3,253,588 A | 5/1966 | Vuilleumier et al. |
| 3,373,992 A | 3/1968 | Ludeman |
| 3,374,675 A | 3/1968 | Michael, Keropian |
| 3,495,824 A | 2/1970 | Cuinier |
| 3,521,623 A | 7/1970 | Nichols et al. |
| 3,667,457 A | 6/1972 | Zumaglini |
| 3,734,087 A | 5/1973 | Sauer et al. |
| 3,866,604 A | 2/1975 | Curless et al. |
| 3,929,335 A | 12/1975 | Malick et al. |
| 3,976,057 A | 8/1976 | Barclay |
| 3,986,498 A | 10/1976 | Lewis |
| 4,037,480 A | 7/1977 | Wagner |
| 4,039,039 A | 8/1977 | Gottfried |
| 4,135,503 A | 1/1979 | Ramano |
| 4,178,923 A | 12/1979 | Curlee |
| 4,235,437 A | 11/1980 | Ruis et al. |
| 4,256,094 A | 3/1981 | Kapp et al. |
| 4,270,527 A | 6/1981 | Peters et al. |
| 4,306,571 A | 12/1981 | Mcleod, Jr. |
| 4,323,080 A | 4/1982 | Melhart |
| 4,331,133 A | 5/1982 | Arkans |
| 4,336,245 A | 6/1982 | Wason |
| 4,354,676 A | 10/1982 | Ariel |
| 4,375,217 A | 3/1983 | Arkans |
| 4,396,010 A | 8/1983 | Arkans |
| 4,397,308 A | 8/1983 | Hepburn |
| 4,407,496 A | 10/1983 | Johnson |
| 4,408,559 A | 10/1983 | Sugiura |
| 4,408,599 A | 10/1983 | Mummert |
| 4,419,988 A | 12/1983 | Mummert |
| 4,422,634 A | 12/1983 | Hopkins |
| 4,426,884 A | 1/1984 | Polchaninoff |
| 4,436,099 A | 3/1984 | Raftopoulos |
| 4,436,303 A | 3/1984 | McKillip et al. |
| 4,485,808 A | 12/1984 | Hepburn |
| 4,501,148 A | 2/1985 | Nicholas et al. |
| 4,508,111 A | 4/1985 | Hepburn |
| 4,512,567 A | 4/1985 | Phillips |
| 4,520,804 A | 6/1985 | DiGeorge |
| 4,522,213 A | 6/1985 | Wallroth |
| 4,538,595 A | 9/1985 | Hajianpour |
| 4,538,600 A | 9/1985 | Hepburn |
| 4,544,154 A | 10/1985 | Ariel |
| 4,548,208 A | 10/1985 | Niemi |
| 4,553,124 A | 11/1985 | Malicki |
| 4,556,216 A | 12/1985 | Pitkanen |
| 4,576,158 A | 3/1986 | Boland |
| 4,586,495 A | 5/1986 | Petrofsky |
| 4,590,925 A | 5/1986 | Dillon |
| 4,604,098 A | 8/1986 | Seamone et al. |
| 4,620,532 A | 11/1986 | Housewerth |
| 4,621,620 A | 11/1986 | Anderson |
| 4,624,246 A | 11/1986 | Ajemian |
| 4,645,199 A | 2/1987 | Bloemendaal |
| 4,651,719 A | 3/1987 | Funk et al. |
| 4,653,479 A | 3/1987 | Maurer |
| 4,654,010 A | 3/1987 | Havriluk |
| 4,681,097 A | 7/1987 | Pansiera |
| 4,697,808 A | 10/1987 | Larson et al. |
| 4,711,242 A | 12/1987 | Petrofsky |
| 4,716,889 A | 1/1988 | Saringer |
| 4,718,665 A | 1/1988 | Airy et al. |
| 4,757,453 A | 7/1988 | Nasiff |
| 4,762,134 A | 8/1988 | Gala |
| 4,763,901 A | 8/1988 | Richter |
| 4,785,674 A | 11/1988 | Orman et al. |
| 4,796,641 A | 1/1989 | Mills et al. |
| 4,801,138 A | 1/1989 | Airy et al. |
| 4,815,469 A | 3/1989 | Cohen et al. |
| 4,817,588 A | 4/1989 | Bledsoe |
| 4,822,336 A | 4/1989 | Ditraglia |
| 4,825,852 A | 5/1989 | Genovese et al. |
| 4,828,257 A | 5/1989 | Dyer et al. |
| 4,830,021 A | 5/1989 | Thornton |
| 4,836,218 A | 6/1989 | Gay et al. |
| 4,839,822 A | 6/1989 | Dormond et al. |
| 4,848,152 A * | 7/1989 | Pratt, Jr. ............... 73/379.06 |
| 4,858,620 A * | 8/1989 | Sugarman et al. ............ 600/587 |
| 4,863,157 A | 9/1989 | Mendel et al. |
| 4,875,469 A | 10/1989 | Brook et al. |
| 4,905,560 A | 3/1990 | Suzuki et al. |
| 4,909,262 A | 3/1990 | Halpern et al. |
| 4,912,638 A | 3/1990 | Pratt, Jr. |
| 4,913,163 A | 4/1990 | Roger et al. |
| 4,922,925 A | 5/1990 | Crandall et al. |
| 4,928,674 A | 5/1990 | Halperin et al. |
| 4,928,959 A | 5/1990 | Bassett et al. |
| 4,930,497 A | 6/1990 | Saringer |
| 4,934,694 A | 6/1990 | McIntosh |
| 4,944,288 A | 7/1990 | Rawcliffe |
| 4,952,928 A | 8/1990 | Carroll et al. |
| 4,958,632 A | 9/1990 | Duggan et al. |
| 4,958,645 A | 9/1990 | Cadell et al. |
| 4,988,981 A | 1/1991 | Zimmerman et al. |
| 5,000,169 A | 3/1991 | Swicegood et al. |
| 5,003,965 A | 4/1991 | Talish et al. |
| 5,012,820 A | 5/1991 | Meyer |
| 5,013,037 A | 5/1991 | Stermer |
| 5,019,974 A | 5/1991 | Beckers |
| 5,020,795 A | 6/1991 | Airy et al. |
| 5,031,604 A | 7/1991 | Dye |
| 5,042,504 A | 8/1991 | Huberti |
| 5,050,618 A | 9/1991 | Larsen |
| 5,052,375 A | 10/1991 | Stark et al. |
| 5,052,379 A | 10/1991 | Airy et al. |
| 5,054,771 A | 10/1991 | Mansfield |
| 5,078,152 A | 1/1992 | Bond et al. |
| 5,090,421 A | 2/1992 | Wagoner, III |
| 5,116,296 A | 5/1992 | Watkins et al. |
| 5,121,747 A | 6/1992 | Andrews |
| 5,125,412 A | 6/1992 | Thornton |
| 5,133,732 A | 7/1992 | Wiktor |
| 5,135,536 A | 8/1992 | Hillstead |
| 5,153,584 A | 10/1992 | Engira |
| 5,178,160 A | 1/1993 | Gracovetsky et al. |
| 5,181,902 A | 1/1993 | Erickson et al. |
| 5,186,163 A | 2/1993 | Dye |
| 5,195,941 A | 3/1993 | Erickson et al. |
| 5,209,712 A | 5/1993 | Feri |
| 5,211,161 A | 5/1993 | Stef |
| 5,218,954 A | 6/1993 | van Bemmelen |
| 5,227,874 A | 7/1993 | Von Kohorn |
| 5,239,987 A | 8/1993 | Kaiser et al. |
| 5,252,102 A | 10/1993 | Singer et al. |
| 5,255,188 A | 10/1993 | Telepko |
| 5,263,491 A | 11/1993 | Thornton |
| 5,265,010 A | 11/1993 | Evans-Paganelli et al. |
| 5,280,265 A | 1/1994 | Kramer et al. |
| 5,280,783 A | 1/1994 | Focht et al. |
| 5,282,460 A | 2/1994 | Boldt |
| 5,284,131 A | 2/1994 | Gray |
| 5,287,546 A | 2/1994 | Tesic et al. |
| 5,297,540 A | 3/1994 | Kaiser et al. |
| 5,307,791 A | 5/1994 | Senoue et al. |
| 5,335,674 A | 8/1994 | Siegler |
| 5,336,245 A | 8/1994 | Adams et al. |
| 5,337,758 A | 8/1994 | Moore et al. |
| 5,338,157 A | 8/1994 | Blomquist |
| 5,354,162 A | 10/1994 | Burdea et al. |
| 5,360,392 A | 11/1994 | McCoy |
| 5,368,546 A | 11/1994 | Stark et al. |
| 5,373,852 A | 12/1994 | Harrison et al. |
| 5,391,141 A | 2/1995 | Hamilton |
| 5,396,896 A | 3/1995 | Tumey et al. |
| 5,410,472 A | 4/1995 | Anderson |
| 5,417,643 A | 5/1995 | Taylor |
| 5,425,750 A | 6/1995 | Moberg |
| 5,435,321 A | 7/1995 | Mcmillen et al. |
| 5,437,610 A | 8/1995 | Cariapa et al. |
| 5,437,617 A | 8/1995 | Heinz et al. |
| 5,443,440 A | 8/1995 | Tumey et al. |
| 5,452,205 A | 9/1995 | Telepko |
| 5,453,075 A | 9/1995 | Bonutti et al. |

(56) References Cited

U.S. PATENT DOCUMENTS

| | | | |
|---|---|---|---|
| 5,462,504 A | 10/1995 | Trulaske et al. | |
| 5,466,213 A | 11/1995 | Hogan et al. | |
| 5,474,083 A | 12/1995 | Church et al. | |
| 5,474,088 A | 12/1995 | Zaharkin et al. | |
| 5,474,090 A | 12/1995 | Begun et al. | |
| 5,476,441 A | 12/1995 | Durfee et al. | |
| 5,484,389 A * | 1/1996 | Stark et al. | 601/34 |
| 5,515,858 A | 5/1996 | Myllymaeki | |
| 5,520,622 A | 5/1996 | Bastyr et al. | |
| 5,538,005 A | 7/1996 | Harrison et al. | |
| 5,553,609 A | 9/1996 | Chen et al. | |
| 5,556,421 A | 9/1996 | Prutchi et al. | |
| 5,558,627 A | 9/1996 | Singer et al. | |
| 5,569,120 A | 10/1996 | Anjanappa et al. | |
| 5,571,959 A | 11/1996 | Griggs | |
| 5,579,378 A | 11/1996 | Arlinghaus, Jr. | |
| 5,583,758 A | 12/1996 | McIlroy et al. | |
| 5,586,067 A | 12/1996 | Gross et al. | |
| 5,596,994 A * | 1/1997 | Bro | 600/545 |
| 5,597,373 A | 1/1997 | Bond et al. | |
| 5,598,849 A * | 2/1997 | Browne | 600/520 |
| 5,625,882 A | 4/1997 | Vook et al. | |
| 5,651,763 A | 7/1997 | Gates | |
| 5,662,693 A | 9/1997 | Johnson et al. | |
| 5,671,733 A | 9/1997 | Raviv et al. | |
| 5,683,351 A | 11/1997 | Kaiser et al. | |
| 5,704,364 A | 1/1998 | Saltzstein et al. | |
| 5,713,841 A | 2/1998 | Graham | |
| 5,722,418 A | 3/1998 | Bro | |
| 5,751,959 A | 5/1998 | Sato et al. | |
| 5,754,121 A | 5/1998 | Ward et al. | |
| 5,772,611 A | 6/1998 | Hocherman | |
| 5,775,332 A | 7/1998 | Goldman | |
| 5,778,618 A | 7/1998 | Abrams | |
| 5,785,666 A | 7/1998 | Costello et al. | |
| 5,788,618 A | 8/1998 | Joutras | |
| 5,792,077 A | 8/1998 | Gomes | |
| 5,792,085 A | 8/1998 | Walters | |
| 5,801,756 A | 9/1998 | Iizawa | |
| 5,810,747 A * | 9/1998 | Brudny et al. | 600/595 |
| 5,823,975 A | 10/1998 | Stark et al. | |
| 5,827,209 A | 10/1998 | Gross | |
| 5,830,162 A | 11/1998 | Giovannetti | |
| 5,836,304 A | 11/1998 | Kellinger et al. | |
| 5,842,175 A | 11/1998 | Andros et al. | |
| 5,843,120 A | 12/1998 | Israel et al. | |
| 5,851,193 A | 12/1998 | Arikka et al. | |
| 5,868,647 A | 2/1999 | Belsole | |
| 5,882,203 A | 3/1999 | Correa et al. | |
| 5,888,173 A | 3/1999 | Singhal | |
| 5,890,997 A | 4/1999 | Roth | |
| 5,908,383 A * | 6/1999 | Brynjestad | 600/300 |
| 5,913,310 A | 6/1999 | Brown | |
| 5,915,240 A | 6/1999 | Karpf | |
| 5,918,603 A | 7/1999 | Brown | |
| 5,929,782 A * | 7/1999 | Stark et al. | 340/870.01 |
| 5,935,086 A | 8/1999 | Beacon et al. | |
| 5,935,162 A | 8/1999 | Dang | |
| 5,940,801 A | 8/1999 | Brown | |
| 5,954,621 A | 9/1999 | Joutras et al. | |
| 5,961,446 A | 10/1999 | Beller et al. | |
| 5,980,435 A * | 11/1999 | Joutras et al. | 482/114 |
| 5,980,447 A | 11/1999 | Trudeau | |
| 5,989,157 A | 11/1999 | Walton | |
| 5,997,476 A | 12/1999 | Brown | |
| 6,007,459 A | 12/1999 | Burgess | |
| 6,012,926 A | 1/2000 | Hodges et al. | |
| 6,014,432 A | 1/2000 | Modney | |
| 6,014,631 A | 1/2000 | Teagarden et al. | |
| 6,029,138 A | 2/2000 | Khorasani et al. | |
| 6,039,688 A | 3/2000 | Douglas et al. | |
| 6,050,924 A | 4/2000 | Shea | |
| 6,053,873 A | 4/2000 | Govari et al. | |
| 6,059,506 A | 5/2000 | Kramer | |
| 6,059,692 A | 5/2000 | Hickman | |
| 6,119,516 A | 9/2000 | Hock | |
| 6,123,861 A | 9/2000 | Santini et al. | |
| 6,126,253 A | 10/2000 | Kelley et al. | |
| 6,127,596 A | 10/2000 | Brown et al. | |
| 6,129,663 A | 10/2000 | Ungless et al. | |
| 6,132,337 A | 10/2000 | Krupka et al. | |
| 6,140,697 A | 10/2000 | Usami et al. | |
| 6,151,586 A * | 11/2000 | Brown | 705/14 |
| 6,161,095 A | 12/2000 | Brown | |
| 6,162,189 A | 12/2000 | Girone et al. | |
| 6,162,253 A | 12/2000 | Conzemius et al. | |
| 6,166,518 A | 12/2000 | Echarri et al. | |
| 6,168,563 B1 | 1/2001 | Brown | |
| 6,171,237 B1 | 1/2001 | Avitall et al. | |
| 6,177,940 B1 | 1/2001 | Bond et al. | |
| 6,183,259 B1 | 2/2001 | Macri et al. | |
| 6,184,797 B1 | 2/2001 | Stark et al. | |
| 6,190,287 B1 | 2/2001 | Nashner | |
| 6,198,971 B1 | 3/2001 | Leysieffer | |
| 6,206,829 B1 | 3/2001 | Iliff | |
| 6,224,486 B1 | 5/2001 | Walker | |
| 6,231,344 B1 | 5/2001 | Merzenich et al. | |
| 6,246,975 B1 | 6/2001 | Rivonelli et al. | |
| 6,248,065 B1 | 6/2001 | Brown | |
| 6,249,809 B1 | 6/2001 | Bro et al. | |
| 6,270,457 B1 | 8/2001 | Bardy | |
| 6,272,481 B1 | 8/2001 | Lawrence et al. | |
| 6,283,761 B1 | 9/2001 | Joao | |
| 6,283,923 B1 * | 9/2001 | Finkelstein et al. | 600/532 |
| 6,296,595 B1 | 10/2001 | Stark et al. | |
| 6,302,844 B1 | 10/2001 | Walker et al. | |
| 6,312,378 B1 | 11/2001 | Bardy | |
| 6,322,502 B1 | 11/2001 | Schoenberg et al. | |
| 6,371,123 B1 | 4/2002 | Stark et al. | |
| 6,413,190 B1 | 7/2002 | Wood et al. | |
| 6,413,279 B1 | 7/2002 | Metzger et al. | |
| 6,442,413 B1 | 8/2002 | Silver | |
| 6,471,723 B1 | 10/2002 | Ashworth et al. | |
| 6,475,477 B1 | 11/2002 | Kohn et al. | |
| 6,491,666 B1 | 12/2002 | Santini, Jr. et al. | |
| 6,515,593 B1 * | 2/2003 | Stark et al. | 340/870.07 |
| 6,530,954 B1 | 3/2003 | Eckmiller | |
| 6,531,417 B2 | 3/2003 | Choi et al. | |
| 6,540,707 B1 | 4/2003 | Stark et al. | |
| 6,563,464 B2 | 5/2003 | Ballantine et al. | |
| 6,572,543 B1 | 6/2003 | Christopherson et al. | |
| 6,610,069 B2 | 8/2003 | Euteneuer et al. | |
| 6,632,158 B1 * | 10/2003 | Nashner | 482/8 |
| 6,638,231 B2 | 10/2003 | Govari et al. | |
| 6,641,540 B2 | 11/2003 | Fleischman et al. | |
| 6,676,706 B1 | 1/2004 | Mears et al. | |
| 6,689,056 B1 | 2/2004 | Kilcoyne et al. | |
| 6,695,866 B1 | 2/2004 | Kuehn et al. | |
| 6,706,005 B2 | 3/2004 | Roy et al. | |
| 6,718,163 B2 | 4/2004 | Tandy | |
| 6,781,284 B1 | 8/2004 | Pelrine et al. | |
| 6,783,260 B2 | 8/2004 | Machi et al. | |
| 6,783,499 B2 | 8/2004 | Schwartz | |
| 6,790,227 B2 | 9/2004 | Burgermeister | |
| 6,821,299 B2 | 11/2004 | Kirking et al. | |
| 6,827,670 B1 | 12/2004 | Stark et al. | |
| 6,850,804 B2 | 2/2005 | Eggers et al. | |
| 6,858,220 B2 | 2/2005 | Greenberg et al. | |
| 6,872,187 B1 | 3/2005 | Stark et al. | |
| 6,875,208 B2 | 4/2005 | Santini, Jr. et al. | |
| 6,937,736 B2 | 8/2005 | Toda | |
| 6,939,377 B2 | 9/2005 | Jayaraman et al. | |
| 7,104,955 B2 | 9/2006 | Bardy | |
| 7,117,028 B2 | 10/2006 | Bardy | |
| 7,226,442 B2 | 6/2007 | Sheppard, Jr. et al. | |
| 7,251,609 B1 | 7/2007 | McAlindon et al. | |
| 7,416,537 B1 | 8/2008 | Stark et al. | |
| 7,510,509 B2 * | 3/2009 | Hickman | 482/8 |
| 8,308,794 B2 | 11/2012 | Martinson et al. | |
| 8,491,572 B2 | 7/2013 | Martinson et al. | |
| 2002/0017834 A1 | 2/2002 | Macdonald | |
| 2002/0029784 A1 | 3/2002 | Stark et al. | |
| 2002/0177782 A1 | 11/2002 | Penner | |
| 2002/0188282 A1 | 12/2002 | Greenberg | |

(56) References Cited

U.S. PATENT DOCUMENTS

| | | | |
|---|---|---|---|
| 2003/0032892 A1 | 2/2003 | Erlach et al. | |
| 2003/0125017 A1 | 7/2003 | Greene et al. | |
| 2003/0153819 A1* | 8/2003 | Iliff | 600/300 |
| 2003/0225331 A1 | 12/2003 | Diederich et al. | |
| 2004/0034332 A1 | 2/2004 | Uhland | |
| 2004/0073175 A1 | 4/2004 | Jacobson et al. | |
| 2004/0102854 A1 | 5/2004 | Zhu | |
| 2004/0106963 A1 | 6/2004 | Tsukamoto et al. | |
| 2004/0143221 A1 | 7/2004 | Shadduck | |
| 2004/0162189 A1* | 8/2004 | Hickman | 482/8 |
| 2004/0172083 A1 | 9/2004 | Penner | |
| 2004/0176672 A1 | 9/2004 | Silver et al. | |
| 2004/0220552 A1 | 11/2004 | Heruth et al. | |
| 2004/0249675 A1 | 12/2004 | Stark et al. | |
| 2005/0054988 A1 | 3/2005 | Rosenberg et al. | |
| 2005/0113652 A1* | 5/2005 | Stark et al. | 600/300 |
| 2005/0113904 A1 | 5/2005 | Shank et al. | |
| 2005/0187797 A1 | 8/2005 | Johnson | |
| 2005/0273170 A1 | 12/2005 | Navarro et al. | |
| 2006/0129050 A1 | 6/2006 | Martinson et al. | |
| 2006/0204532 A1 | 9/2006 | John et al. | |
| 2006/0244532 A1 | 11/2006 | Trifonov et al. | |
| 2006/0271112 A1 | 11/2006 | Martinson et al. | |
| 2008/0040153 A1 | 2/2008 | Davis, Jr. | |
| 2008/0097143 A1 | 4/2008 | Califorrni | |
| 2010/0121160 A1 | 5/2010 | Stark | |
| 2012/0116806 A1 | 5/2012 | Stark et al. | |
| 2012/0271200 A1 | 10/2012 | Martinson et al. | |
| 2013/0066426 A1 | 3/2013 | Martinson et al. | |

FOREIGN PATENT DOCUMENTS

| | | |
|---|---|---|
| EP | 6689056 | 2/2004 |
| EP | 6875208 | 4/2005 |
| GB | 2177603 A | 1/1987 |
| JP | 4-44708 A | 2/1992 |
| JP | 05-038684 A | 2/1993 |
| JP | 5-38684 A | 2/1993 |
| JP | 05038684 A | 2/1993 |
| JP | 5-146476 A | 6/1993 |
| JP | 5146476 | 6/1993 |
| JP | 5146476 A | 6/1993 |
| JP | 7-504102 A | 5/1995 |
| JP | 3023228 U | 4/1996 |
| JP | 09-084771 | 3/1997 |
| JP | 9-84771 A | 3/1997 |
| JP | 09084771 A | 3/1997 |
| JP | 09-114671 A | 5/1997 |
| JP | 9-114671 A | 5/1997 |
| JP | 09114671 A | 5/1997 |
| NL | 7806-327 | 12/1979 |
| NL | 7806327 | 12/1979 |
| SU | 1380747 A | 3/1988 |
| SU | 1750681 A | 7/1992 |
| WO | WO 95/01769 | 1/1995 |
| WO | WO-9522307 A1 | 8/1995 |
| WO | WO-9604848 A1 | 2/1996 |
| WO | WO-9620464 A1 | 7/1996 |
| WO | WO-9636278 | 11/1996 |
| WO | WO-9636278 A1 | 11/1996 |
| WO | WO-9837926 | 9/1998 |
| WO | WO-9837926 A1 | 9/1998 |
| WO | 98/42257 A1 | 10/1998 |
| WO | WO-9842257 A1 | 10/1998 |
| WO | WO-0012041 A2 | 3/2000 |
| WO | WO-0040171 A2 | 7/2000 |
| WO | WO-01/26548 A1 | 4/2001 |
| WO | WO-0126548 A1 | 4/2001 |
| WO | WO-0135473 A1 | 5/2001 |
| WO | WO-2004093725 A2 | 11/2004 |
| WO | WO-2005046514 A2 | 5/2005 |
| WO | WO-2005082452 A1 | 9/2005 |
| WO | WO-2005084257 A2 | 9/2005 |

OTHER PUBLICATIONS

1994 Thera-Kinetics Product literatuare.

"Let Your Fingers Do the Talking" by, Fred Hapgood, Boston, vol. 19, Iss. 17, Nov. 18, 1997, pp. 119-120.

English translation of Office Action for Japanese Patent Application No. 2000-567165, dated Apr. 9, 2009.

"U.S. Appl. No. 10/854,400, Decision on Pre-Appeal Brief Request mailed Oct. 23, 2012", 2 pgs.

"U.S. Appl. No. 10/854,400, Pre-Appeal Brief Request filed Sep. 24, 2012", 5 pgs.

"U.S. Appl. No. 11/267,386, Notice of Allowability mailed Oct. 5, 2012", 2 pgs.

"U.S. Appl. No. 12/689,568, Pre-Appeal Brief Request for Review filed Sep. 25, 2012", 5 pgs.

"U.S. Appl. No. 13/184,289, Response filed Nov. 5, 2012 to Non Final Office Action mailed Jun. 8, 2012", 13 pgs.

"U.S. Appl. No. 09/329,880, Notice of Allowance mailed Mar. 15, 2001", 6 pgs.

"U.S. Appl. No. 09/329,880, Notice of Allowance mailed Jun. 8, 2000", 3 pgs.

"U.S. Appl. No. 09/329,880, Notice of Allowance mailed Oct. 29, 2001", 5 pgs.

"U.S. Appl. No. 09/339,071, Final Office Action mailed Jul. 13, 2007", 9 pgs.

"U.S. Appl. No. 09/339,071, Advisory Action mailed May 4, 2004", 3 pgs.

"U.S. Appl. No. 09/339,071, Advisory Action mailed Jun. 7, 2006", 5 pgs.

"U.S. Appl. No. 09/339,071, Advisory Action mailed Jul. 7, 2005", 3 pgs.

"U.S. Appl. No. 09/339,071, Examiner Interview Summary mailed Apr. 7, 2004", 4 pgs.

"U.S. Appl. No. 09/339,071, Examiner Interview Summary mailed Aug. 15, 2006", 3 pgs.

"U.S. Appl. No. 09/339,071, Final Office Action mailed Jan. 25, 2006", 13 pgs.

"U.S. Appl. No. 09/339,071, Final Office Action mailed Jan. 28, 2004", 13 pgs.

"U.S. Appl. No. 09/339,071, Final Office Action mailed Aug. 27, 2002", 10 pgs.

"U.S. Appl. No. 09/339,071, Final Office Action mailed Dec. 15, 2004", 13 pgs.

"U.S. Appl. No. 09/339,071, Non Final Office Action mailed May 21, 2003", 11 pgs.

"U.S. Appl. No. 09/339,071, Non Final Office Action mailed Jun. 24, 2004", 8 pgs.

"U.S. Appl. No. 09/339,071, Non Final Office Action mailed Aug. 2, 2005", 13 pgs.

"U.S. Appl. No. 09/339,071, Non Final Office Action mailed Oct. 12, 2006", 8 pgs.

"U.S. Appl. No. 09/339,071, Non Final Office Action mailed Nov. 15, 2007", 10 pgs.

"U.S. Appl. No. 09/339,071, Non Final Office Action mailed Dec. 17, 2001", 8 pgs.

"U.S. Appl. No. 09/339,071, Notice of Allowance mailed Apr. 23, 2009", 6 pgs.

"U.S. Appl. No. 09/339,071, Preliminary Amendment filed Feb. 27, 2003", 9 pgs.

"U.S. Appl. No. 09/339,071, Preliminary Amendment filed Sep. 25, 2006", 11 pgs.

"U.S. Appl. No. 09/339,071, Preliminary Amendment filed Oct. 16, 2007", 10 pgs.

"U.S. Appl. No. 09/339,071, Response filed Feb. 15, 2008 to Non Final Office Action mailed Nov. 15, 2007", 5 pgs.

"U.S. Appl. No. 09/339,071, Response filed Apr. 15, 2004 to Final Office Action mailed Jan. 28, 2004", 8 pgs.

"U.S. Appl. No. 09/339,071, Response filed Apr. 16, 2007 to Non Final Office Action mailed Oct. 12, 2006", 11 pgs.

(56) References Cited

OTHER PUBLICATIONS

"U.S. Appl. No. 09/339,071, Response filed May 23, 2006 to Final Office Action mailed Jan. 25, 2006", 14 pgs.
"U.S. Appl. No. 09/339,071, Response filed Jun. 17, 2002 to Non Final Office Action mailed Dec. 17, 2001", 7 pgs.
"U.S. Appl. No. 09/339,071, Response filed Jun. 28, 2005 to Final Office Action mailed Dec. 15, 2004", 15 pgs.
"U.S. Appl. No. 09/339,071, Response filed Jul. 3, 2000 to Restriction Requirement mailed Jun. 9, 2000", 2 pgs.
"U.S. Appl. No. 09/339,071, Response filed Sep. 24, 2004 to Non Final Office Action mailed Jun. 24, 2004", 11 pgs.
"U.S. Appl. No. 09/339,071, Response filed Nov. 2, 2005 to Non Final Office Action mailed Aug. 2, 2005", 12 pgs.
"U.S. Appl. No. 09/339,071, Response filed Nov. 21, 2003 to Non Final Office Action mailed May 21, 2003", 11 pgs.
"U.S. Appl. No. 09/339,071, Restriction Requirement mailed Jun. 9, 2000", 8 pgs.
"U.S. Appl. No. 09/382,433, Amendment filed Jan. 23, 2003 in Response to Non-Final Office Action mailed Jul. 23, 2002", 8 pgs.
"U.S. Appl. No. 09/382,433, Amendment filed Jun. 4, 2001 in Response to Non-Final Office Action mailed Feb. 28, 2001", 5 pgs.
"U.S. Appl. No. 09/382,433, Amendment filed Jun. 18, 2002 in Response to Office Action mailed Jun. 3, 2002", 2 pgs.
"U.S. Appl. No. 09/382,433, Amendment filed Jul. 23, 2004 in Response to Non-Final Office Action mailed Jan. 28, 2004", 11 pgs.
"U.S. Appl. No. 09/382,433, Amendment filed Oct. 13, 2003 in Response to Non-Final Office Action mailed Apr. 11, 2003", 11 pgs.
"U.S. Appl. No. 09/382,433, Amendment filed Nov. 30, 2000 in Response to Office Action mailed Nov. 20, 2000", 2 pgs.
"U.S. Appl. No. 09/382,433, Final Office Action mailed Aug. 24, 2001", 7 pgs.
"U.S. Appl. No. 09/382,433, Non-Final Office Action mailed Jan. 28, 2004", 9 pgs.
"U.S. Appl. No. 09/382,433, Non-Final Office Action mailed Feb. 28, 2001", 7 pgs.
"U.S. Appl. No. 09/382,433, Non-Final Office Action mailed Apr. 11, 2003", 13 pgs.
"U.S. Appl. No. 09/382,433, Non-Final Office Action mailed Jul. 23, 2002", 5 pgs.
"U.S. Appl. No. 09/382,433, Notice of Allowance mailed Sep. 8, 2004", 5 pgs.
"U.S. Appl. No. 09/382,433, Office Action mailed Jun. 3, 2002", 4 pgs.
"U.S. Appl. No. 09/382,433, Preliminary Amendment filed Feb. 25, 2002 in Response to Final Office Action mailed Aug. 24, 2001", 7 pgs.
"U.S. Appl. No. 09/416,192, Final Office Action mailed Jul. 2, 2002", 4 pgs.
"U.S. Appl. No. 09/416,192, Final Office Action mailed Nov. 18, 2003", 5 pgs.
"U.S. Appl. No. 09/416,192, Non Final Office Action mailed Mar. 7, 2003", 4 pgs.
"U.S. Appl. No. 09/416,192, Non Final Office Action mailed Jul. 19, 2001", 4 pgs.
"U.S. Appl. No. 09/416,192, Notice of Allowance mailed May, 14, 2004", 5 pgs.
"U.S. Appl. No. 09/416,192, Response filed Jan. 2, 2003 to Final Office Action mailed Jul. 2, 2002", 3 pgs.
"U.S. Appl. No. 09/416,192, Response filed Jan. 17, 2002 to Non Final Office Action mailed Jul. 19, 2001", 4 pgs.
"U.S. Appl. No. 09/416,192, Response filed Feb. 18, 2004 to Final Office Action mailed Nov. 18, 2003", 5 pgs.
"U.S. Appl. No. 09/416,192, Response filed May 1, 2001 to Restriction Requirement mailed Mar. 27, 2001", 6 pgs.
"U.S. Appl. No. 09/416,192, Response filed Sep. 8, 2003 to Non Final Office Action mailed Mar. 7, 2003", 3 pgs.
"U.S. Appl. No. 09/968,595, Advisory Action mailed Mar. 30, 2007", 3 pgs.
"U.S. Appl. No. 09/968,595, Examiner Interview Summary filed Jul. 18, 2006", 3 pgs.
"U.S. Appl. No. 09/968,595, Examiner Interview Summary mailed Oct. 10, 2008", 2 pgs.
"U.S. Appl. No. 09/968,595, Examiner Interview Summary mailed Nov. 17, 2009", 3 pgs.
"U.S. Appl. No. 09/968,595, Final Office Action mailed Jan. 8, 2007", 16 pgs.
"U.S. Appl. No. 09/968,595, Final Office Action mailed Feb. 11, 2008", 14 pgs.
"U.S. Appl. No. 09/968,595, Final Office Action mailed May 11, 2010", 22 pgs.
"U.S. Appl. No. 09/968,595, Non Final Office Action mailed Mar. 23, 2006", 12 pgs.
"U.S. Appl. No. 09/968,595, Non Final Office action mailed Jun. 3, 2009", 14 pgs.
"U.S. Appl. No. 09/968,595, Non Final Office Action mailed Jun. 18, 2007", 18 pgs.
"U.S. Appl. No. 09/968,595, Non Final Office Action mailed Jun. 27, 2008", 15 pgs.
"U.S. Appl. No. 09/968,595, Non Final Office Action mailed Aug. 16, 2010", 27 pgs.
"U.S. Appl. No. 09/968,595, Non Final Office Action mailed Oct. 26, 2009", 16 pgs.
"U.S. Appl. No. 09/968,595, Preliminary Amendment filed Apr. 3, 2007", 13 pgs.
"U.S. Appl. No. 09/968,595, Response filed Jan. 26, 2010 to Non Final Office Action mailed Oct. 26, 2009", 1 pg.
"U.S. Appl. No. 09/968,595, Response filed Mar. 7, 2007 to Final Office Action mailed Jan. 8, 2007", 2 pgs.
"U.S. Appl. No. 09/968,595, Response filed Apr. 11, 2008 to Final Office Action mailed Feb. 11, 2008", 10 pgs.
"U.S. Appl. No. 09/968,595, Response filed Jul. 5, 2006 to Non Final Office Action mailed Mar. 23, 2006", 14 pgs.
"U.S. Appl. No. 09/968,595, Response filed Jul. 12, 2010 to Final Office Action mailed May 11, 2010", 14 pgs.
"U.S. Appl. No. 09/968,595, Response filed Jul. 30, 2009 to Non Final Office Action mailed Jun. 3, 2009", 12 pgs.
"U.S. Appl. No. 09/968,595, Response filed Sep. 26, 2008 to Non Final Office Action mailed Jun. 27, 2008", 9 pgs.
"U.S. Appl. No. 09/968,595, Response filed Oct. 4, 2007 to Non Final Office Action mailed Jun. 18, 2007", 2 pgs.
"U.S. Appl. No. 09/968,595, Response filed Oct. 12, 2006 to Non Final Office Action mailed Oct. 6, 2006", 2 pgs.
"U.S. Appl. No. 09/968,595, Supplemental Response to Non Final Office Action mailed Jun. 27, 2008", 11 pgs.
"U.S. Appl. No. 10/403,650, Advisory Action mailed Mar. 15, 2010", 4 pgs.
"U.S. Appl. No. 10/403,650, Advisory Action mailed Sep. 17, 2008", 3 pgs.
"U.S. Appl. No. 10/403,650, Advisory Action mailed Oct. 2, 2009", 3 pgs.
"U.S. Appl. No. 10/403,650, Examiner Interview Summary filed Oct. 20, 2009", 2 pgs.
"U.S. Appl. No. 10/403,650, Final Office Action mailed Jun. 24, 2009", 7 pgs.
"U.S. Appl. No. 10/403,650, Final Office Action mailed Jun. 27, 2008", 9 pgs.
"U.S. Appl. No. 10/403,650, Final Office Action mailed Oct. 17, 2007", 7 pgs.
"U.S. Appl. No. 10/403,650, Final Office Action mailed Nov. 25, 2009", 7 pgs.
"U.S. Appl. No. 10/403,650, Non Final Office Action mailed Apr. 12, 2007", 11 pgs.
"U.S. Appl. No. 10/403,650, Non Final Office Action mailed Nov. 15, 2005", 5 pgs.
"U.S. Appl. No. 10/403,650, Non Final Office Action mailed Nov. 26, 2007", 8 pgs.
"U.S. Appl. No. 10/403,650, Non Final Office Action mailed Dec. 24, 2008", 8 pgs.
"U.S. Appl. No. 10/403,650, Preliminary Amendment filed Feb. 26, 2008", 10 pgs.
"U.S. Appl. No. 10/403,650, Preliminary Amendment filed Sep. 22, 2008", 10 pgs.

(56) References Cited

OTHER PUBLICATIONS

"U.S. Appl. No. 10/403,650, Preliminary Amendment filed Oct. 30, 2007", 9 pgs.
"U.S. Appl. No. 10/403,650, Response filed Aug. 24, 2009 to Non Final Office Action mailed Jun. 24, 2009", 11 pgs.
"U.S. Appl. No. 10/403,650, Response filed Jan. 25, 2010 to Final Office Action mailed Nov. 25, 2009", 10 pgs.
"U.S. Appl. No. 10/403,650, Response filed Feb. 15, 2006 to Non Final Office Action mailed Nov. 15, 2005", 9 pgs.
"U.S. Appl. No. 10/403,650, Response filed Mar. 24, 2009 to Non Final Office Action mailed Dec. 24, 2008", 9 pgs.
"U.S. Appl. No. 11/403,650, Response filed Jul. 28, 2005 to Restriction Requirement mailed Jul. 12, 2005", 2 pgs.
"U.S. Appl. No. 10/403,650, Response filed Aug. 10, 2007 to Non final Office Action mailed Apr. 12, 2007", 11 pgs.
"U.S. Appl. No. 10/403,650, Response filed Aug. 25, 2008 to Final Office Action mailed Jun. 27, 2008", 10 pgs.
"U.S. Appl. No. 10/819,092, Final Office Action mailed Jan. 9, 2008", 11 pgs.
"U.S. Appl. No. 10/819,092, Final Office Action mailed Mar. 13, 2009", 11 pgs.
"U.S. Appl. No. 10/819,092, Final Office Action mailed Sep. 28, 2009", 13 pgs.
"U.S. Appl. No. 10/819,092, Non Final Office Action mailed Sep. 3, 2008", 11 pgs.
"U.S. Appl. No. 10/819,092, Preliminary Amendment filed Jul. 10, 2009 to Final Office Action mailed Mar. 13, 2009", 9 pgs.
"U.S. Appl. No. 10/819,092, Response filed Mar. 10, 2008 to Final Office Action mailed Jan. 9, 2008", 10 pgs.
"U.S. Appl. No. 10/819,092, Response filed Jun. 9, 2008 to Restriction Requirement mailed May 12, 2008", 6 pgs.
"U.S. Appl. No. 10/819,092, Response filed Dec. 3, 2008 to Non Final Office Action mailed Sep. 3, 2008", 8 pgs.
"U.S. Appl. No. 10/845,400, Response filed Dec. 22, 2010 to Non Final Office mailed Jun. 22, 2010", 7 pgs.
"U.S. Appl. No. 10/854,400, Response filed Jan. 11, 2012 to Non Final Office Action mailed Oct. 11, 2011", 7 pgs.
"U.S. Appl. No. 10/854,400, Advisory Action mailed Apr. 6, 2010", 2 pgs.
"U.S. Appl. No. 10/854,400, Final Office Action mailed Jan. 19, 2010", 11 pgs.
"U.S. Appl. No. 10/854,400, Final Office Action mailed Mar. 14, 2011", 11 pgs.
"U.S. Appl. No. 10/854,400, Non Final Office Action mailed Jun. 22, 2010", 10 pgs.
"U.S. Appl. No. 10/854,400, Non Final Office Action mailed Jul. 9, 2009", 12 pgs.
"U.S. Appl. No. 10/854,400, Non Final Office Action mailed Oct. 11, 2011", 9 pgs.
"U.S. Appl. No. 10/854,400, Preliminary Amendment filed May 26, 2004", 2 pgs.
"U.S. Appl. No. 10/854,400, Response filed Mar. 23, 2010 to Final Office Action mailed Jan. 19, 2010", 6 pgs.
"U.S. Appl. No. 10/854,400, Response filed Jul. 14, 2011 to Final Office Action mailed Mar. 14, 2011", 7 pgs.
"U.S. Appl. No. 10/854,400, Response filed Oct. 2, 2009 to Non Final Office Action mailed Jul. 9, 2009", 13 pgs.
"U.S. Appl. No. 10/997,737, Advisory Action mailed Aug. 29, 2008", 3 pgs.
"U.S. Appl. No. 10/997,737, Advisory Action mailed Dec. 5, 2006", 3 pgs.
"U.S. Appl. No. 10/997,737, Examiner Interview Summary mailed Jan. 19, 2010", 2 pgs.
"U.S. Appl. No. 10/997,737, Examiner Interview Summary mailed Oct. 31, 2007", 2 pgs.
"U.S. Appl. No. 10/997,737, Final Office Action mailed Feb. 20, 2008", 10 pgs.
"U.S. Appl. No. 10/997,737, Final Office Action mailed Jun. 10, 2008", 11 pgs.
"U.S. Appl. No. 10/997,737, Final Office Action mailed Oct. 24, 2006", 6 pgs.
"U.S. Appl. No. 10/997,737, Non Final Office Action mailed Mar. 16, 2009", 7 pgs.
"U.S. Appl. No. 10/997,737, Amendment filed Jun. 8, 2009 in Response to Non Final Office Action mailed Mar. 16, 2009", 12 pgs.
"U.S. Appl. No. 10/997,737, Non Final Office Action mailed Jun. 27, 2006", 12 pgs.
"U.S. Appl. No. 10/997,737, Non Final Office Action mailed Oct. 29, 2008", 8 pgs.
"U.S. Appl. No. 10/997,737, Preliminary Amendment filed Feb. 21, 2007", 9 pgs.
"U.S. Appl. No. 10/997,737, Preliminary Amendment filed Nov. 24, 2004", 3 pgs.
"U.S. Appl. No. 10/997,737, Response filed Jan. 11, 2008 to Non Final Office Action mailed Jul. 24, 2007", 14 pgs.
"U.S. Appl. No. 10/997,737, Response filed Apr. 4, 2008 to Final Office Action mailed Feb. 20, 2008", 11 pgs.
"U.S. Appl. No. 10/997,737, Response filed Jun. 13, 2008 to Final Office Action mailed Jun. 10, 2008", 11 pgs.
"U.S. Appl. No. 10/997,737, Response filed Sep. 10, 2009 to Non Final Office Action mailed Mar. 16, 2009", 15 pgs.
"U.S. Appl. No. 10/997,737, Response filed Sep. 27, 2006 to Non Final Office Action mailed Jun. 27, 2006", 7 pgs.
"U.S. Appl. No. 10/997,737, Response filed Oct. 17, 2007 to Restriction Requirement mailed Jul. 24, 2007", 14 pgs.
"U.S. Appl. No. 10/997,737, Response filed Nov. 10, 2006 to Final Office Action mailed Oct. 24, 2006", 10 pgs.
"U.S. Appl. No. 10/997,737, Response filed on Dec. 12, 2008 to Non Final Office Action mailed Oct. 29, 2008", 11 pgs.
"U.S. Appl. No. 10/997,737, Restriction Requirement mailed Jul. 24, 2007", 10 pgs.
"U.S. Appl. No. 11/017,593, Final Office Action mailed Sep. 6, 2006", 10 pgs.
"U.S. Appl. No. 11/017,593, Non Final Office Action mailed Sep. 7, 2005", 7 pgs.
"U.S. Appl. No. 11/017,593, Response filed Feb. 7, 2006 to Non Final Office Action mailed Sep. 7, 2005", 11 pgs.
"U.S. Appl. No. 11/017,593, Response filed May 12, 2006 to Restriction Requirement mailed Apr. 18, 2006", 7 pgs.
"U.S. Appl. No. 11/267,386, Advisory Action mailed May 22, 2009", 3 pgs.
"U.S. Appl. No. 11/267,386, Advisory Action mailed Jun. 4, 2010", 3 pgs.
"U.S. Appl. No. 11/267,386, Advisory Action mailed Jun. 16, 2009", 3 pgs.
"U.S. Appl. No. 11/267,386, Examiner Interview Summary filed Sep. 8, 2009", 2 pgs.
"U.S. Appl. No. 11/267,386, Final Office Action mailed Mar. 10, 2009", 8 pgs.
"U.S. Appl. No. 11/267,386, Final Office Action mailed Mar. 30, 2010", 11 pgs.
"U.S. Appl. No. 11/267,386, Final Office Action mailed Jul. 7, 2009", 10 pgs.
"U.S. Appl. No. 11/267,386, Final Office Action mailed Aug. 19, 2011", 13 pgs.
"U.S. Appl. No. 11/267,386, Non Final Action mailed Sep. 29, 2009", 10 pgs.
"U.S. Appl. No. 11/267,386, Non Final Office Action mailed Jun. 17, 2008", 10 pgs.
"U.S. Appl. No. 11/267,386, Non Final Office Action mailed Nov. 29, 2010", 11 pgs.
"U.S. Appl. No. 11/267,386, Preliminary Amendment filed Jun. 10, 2009", 6 pgs.
"U.S. Appl. No. 11/267,386, Request for Continued Examination filed Jun. 10, 2009", 6 pgs.
"U.S. Appl. No. 11/267,386, Response filed Jan. 18, 2012 to Final Office Action mailed Aug. 19, 2011", 7 pgs.
"U.S. Appl. No. 11/267,386, Response filed May 1, 2008 to Non Final Office Action mailed Apr. 2, 2008", 6 pgs.
"U.S. Appl. No. 11/267,386, Response filed May 7, 2009 to Final Office Action mailed Mar. 10, 2009", 6 pgs.

(56) References Cited

OTHER PUBLICATIONS

"U.S. Appl. No. 11/267,386, Response filed May 20, 2010 to Non Final Office Action mailed Mar. 30, 2010", 7 pgs.
"U.S. Appl. No. 11/267,386, Response filed May 27, 2011 to Non Final Office Action mailed Nov. 29, 2010", 7 pgs.
"U.S. Appl. No. 11/267,386, Response filed May 28, 2009 to Advisory Action mailed May 22, 2009", 2 pgs.
"U.S. Appl. No. 11/267,386, Response filed Sep. 17, 2008 to Non Final Office Action mailed Jun. 17, 2008", 8 pgs.
"U.S. Appl. No. 11/267,386, Response filed Dec. 29, 2009 to Non Final Office Action mailed Sep. 29, 2009", 6 pgs.
"U.S. Appl. No. 11/267,386, Non Final Office Action mailed Apr. 2, 2008", 10 pgs.
"U.S. Appl. No. 11/494,719, Advisory Action mailed Jan. 23, 2008", 3 pgs.
"U.S. Appl. No. 11/494,719, Advisory Action mailed Mar. 25, 2009", 3 pgs.
"U.S. Appl. No. 11/494,719, Examiner Interview Summary mailed Feb. 23, 2010", 3 pgs.
"U.S. Appl. No. 11/494,719, Examiner Interview Summary mailed Aug. 27, 2009", 2 pgs.
"U.S. Appl. No. 11/494,719, Final Office Action mailed Jan. 8, 2009", 7 pgs.
"U.S. Appl. No. 11/494,719, Final Office Action mailed Nov. 8, 2007", 8 pgs.
"U.S. Appl. No. 11/494,719, Final Office Action mailed Nov. 16, 2009", 8 pgs.
"U.S. Appl. No. 11/494,719, Non Final Action mailed Mar. 28, 2008", 9 pgs.
"U.S. Appl. No. 11/494,719, Non Final Office Action mailed May 30, 2007", 9 pgs.
"U.S. Appl. No. 11/494,719, Non Final Office Action mailed Jun. 30, 2009", 7 pgs.
"U.S. Appl. No. 11/494,719, Response filed Jan. 8, 2008 to Final Office Action mailed Nov. 8, 2007", 11 pgs.
"U.S. Appl. No. 11/494,719, Response filed Feb. 18, 2010 to Final Office Action mailed Nov. 16, 2009", 10 pgs.
"U.S. Appl. No. 11/494,719, Response filed Mar. 9, 2009 to Final Office Action mailed Jan. 8, 2009", 9 pgs.
U.S. Appl. No. 11/494,719, Response filed Jun. 25, 2008 to Non Final Office Action mailed Mar. 28, 2008, 13 pgs.
"U.S. Appl. No. 11/494,719, Response filed Aug. 30, 2007 to Non Final Office Action mailed May 30, 2007", 2 pgs.
"U.S. Appl. No. 11/494,719, Response filed Oct. 13, 2008 to Restriction Requirement mailed Sep. 12, 2008", 6 pgs.
"U.S. Appl. No. 11/494,719, Response filed Sep. 1, 2009 to Non Final Office Action mailed Jun. 30, 2009", 10 pgs.
"U.S. Appl. No. 12/689,568, Non Final Office Action mailed Sep. 8, 2011", 22 pgs.
"U.S. Appl. No. 12/689,568, Preliminary Amendment filed Jan. 19, 2010", 5 pgs.
"U.S. Appl. No. 12/689,568, Response filed Feb. 8, 2012 to Non-Final Office Action mailed Sep. 8, 2011", 11 pgs.
"U.S. Appl. No. 12/689,568, Response filed Jun. 29, 2011 to Restriction Requirement mailed May 31, 2011", 8 pgs.
"U.S. Appl. No. 12/689,568, Restriction Requirement mailed May 31, 2011", 7 pgs.
"Chinese Application Serial No. 99812468.0, First Office Action issued Jul. 25, 2003", (w/ English Translation), 10 pgs.
*Clinical Biomechanics of the Spine,* 2nd Edition, J. B. Lippincott Company, Philadelphia, PA (1990), p. 482.
"European Application Serial No. 99966681.1, Supplementary Search Report mailed Sep. 8, 2004", 6 pgs.
"European Application Serial No. 05822048.4, Supplementary European Search Report mailed Mar. 5, 2009", 6 pgs.
"European Application Serial No. 05822048.4, Supplementary European Search Report mailed Mar. 24, 2009", 12 pgs.
"European Application Serial No. 96920238.1, Supplementary Partial European Search Report mailed Nov. 21, 2002", 5 pgs.
"European Application Serial No. 98915149.3, Supplementary Partial European Search Report dated Apr. 1, 2003", 5 pgs.
"European Application Serial No. 98915149.3, Supplementary Partial European Search Report mailed Jul. 11, 2003", 5 pgs.
"European Application Serial No. 99966681.1, Office Action mailed Jan. 9, 2009", 5 pgs.
"European Application Serial No. 99966681.1, Office Action mailed Feb. 7, 2006", 5 pgs.
"European Application Serial No. 99966681.1, Office Action mailed Mar. 11, 2005", 3 pgs.
"European Application Serial No. 99966681.1, Office Action mailed Sep. 11, 2007", 5 pgs.
"European Application Serial No. 99966681.1, Reply filed Apr. 14, 2008 to Office Action mailed Sep. 11, 2007", 7 pgs.
"European Application Serial No. 99966681.1, Reply filed Jun. 19, 2006 to Office Action mailed Feb. 7, 2006", 11 pgs.
"European Application Serial No. 99966681.1, Response filed Jul. 21, 2005 to Office Action mailed Mar. 11, 2005", 3 pgs.
"European Application Serial No. 99966681.1, Response filed Jul. 23, 2004 to Partial European Search Report mailed Jun. 14, 2004", 4 pgs.
"European Application Serial No. 99966681.1, Supplementary Partial European Search Report", 6 pgs.
"International Application Serial No. PCT/US00/15888, International Preliminary Examination Report mailed Jul. 23, 2001", 43 pgs.
"International Application Serial No. PCT/US00/15888, International Search Report mailed Aug. 21, 2000", 2 pgs.
"International Application Serial No. PCT/US00/16859, International Preliminary Examination Report mailed Dec. 2, 2002", 8 pgs.
"International Application Serial No. PCT/US00/16859, International Search Report mailed Oct. 16, 2000", 7 pgs.
"International Application Serial No. PCT/US00/16859, Written Opinion mailed Oct. 19, 2001", 6 pgs.
"International Application Serial No. PCT/US00/26990, International Preliminary Examination Report mailed Oct. 24, 2001", 4 pgs.
"International Application Serial No. PCT/US00/26990, International Search Report mailed Dec. 27, 2000", 3 pgs.
"International Application Serial No. PCT/US05/41021, International Search Report mailed Jan. 25, 2007", 1 pg.
"International Application Serial No. PCT/US05/41021, Written Opinion mailed Jan. 25, 2007", 3 pgs.
"International Application Serial No. PCT/US2005/41339, International Search Report mailed Jun. 20, 2006", 3 pgs.
"International Application Serial No. PCT/US2005/41339, Written Opinion mailed Jun. 20, 2006", 6 pgs.
"International Application Serial No. PCT/US96/07047, International Preliminary Examination Report mailed Sep. 4, 1997", 5 pgs.
"International Application Serial No. PCT/US96/07047, International Search Report mailed Oct. 2, 1996", 7 pgs.
"International Application Serial No. PCT/US96/07047, Written Opinion mailed May 22, 1997", 4 pgs.
"International Application Serial No. PCT/US98/05600, International Preliminary Examination Report mailed Jun. 16, 1999", 7 pgs.
"International Application Serial No. PCT/US98/05600, International Search Report mailed Jul. 9, 1998", 6 pgs.
"International Application Serial No. PCT/US98/05600, Written Opinion mailed Jan. 27, 1999", 6 pgs.
"International Application Serial No. PCT/US99/19935, Article 34 Amendment filed Nov. 17, 2000", 19 pgs.
"International Application Serial No. PCT/US99/19935, International Preliminary Examination Report mailed Feb. 26, 2001", 23 pgs.
"International Application Serial No. PCT/US99/19935, International Search Report mailed Mar. 24, 2000", 6 pgs.
"International Application Serial No. PCT/US99/19935, Written Opinion mailed Sep. 19, 2000", 7 pgs.
"International Application Serial No. PCT/US99/31030, International Preliminary Examination Report mailed Jun. 12, 2001", 8 pgs.
"International Application Serial No. PCT/US99/31030, International Search Report Jul. 13, 2000", 5 pgs.
"International Application Serial No. PCT/US99/31030, Written Opinion mailed Dec. 13, 2000", 7 pgs.

(56) References Cited

OTHER PUBLICATIONS

"Japanese Application Serial No. 2000-567165, Office Action mailed Apr. 9, 2009", (English Translation), 3 pgs.

"Japanese Application Serial No. 2000-591930, Argument and Amendment filed Feb. 26, 2008 filed in Response to Office Action mailed Nov. 27, 2007", 4 pgs.

"Japanese Application Serial No. 2000-591930, Decision of Refusal mailed Mar. 25, 2008", (w/ English Translation), 3 pgs.

"Japanese Application Serial No. 2000-591930, Official Action mailed Nov. 27, 2007", (English Translation), 3 pgs.

"Japanese Application Serial No. 545857/98, Amendment and Argument filed Jan. 9, 2007", 11 pgs.

"Japanese Application Serial No. 545857/98, Appeal Brief and Amendment filed Jun. 25, 2007", 10 pgs.

"Japanese Application Serial No. 545857/98, Final Rejection mailed Mar. 26, 2007", (English Translation), 2 pgs.

"Japanese Application Serial No. 545857/98, Office Action mailed Aug. 17, 2006", (English Translation), 6 pgs.

"Machine Translation of JP 58-109212", 24 pgs.

"Put Your Patient's Recovery Steps Ahead with the Sutter CPM 9000", Sutter Biomedical Inc., *SUT 133*, V85, (Jan. 1985), 1-6.

"Thera-Kinetics Product Literature", (1994), 26 pgs.

Antich, T J, et al., "Modification of Quadriceps Femoris Muscle Exercises During Knee Rehabilitation", *Physical Therapy*, 66(8), (1986), 1246-1251.

Baumeister, T, et al., *Standard Handbook for Mechanical Engineers*, 8th ed., McGraw-Hill Book Company, New York, NY, (1978), p. 16-8.

Biering-Sorenson, F., "A One-Year Prospective Study of Low Back Trouble in a General Population", Danish Medical Bulletin, 31(5), (Oct. 1984), 362-375.

During, J., et al., "Toward Standards for Posture—Postural Characteristics of the Lower Back System in Normal and Pathologic Conditions", *Spine*, 10(1), (1985), 83-87.

Elnagger, I. M., et al., "Effects of Spinal Flexion and Extension Exercises on Low-Back Pain and Spinal Mobility in Chronic Mechanical Low-Back Pain Patients", *Spine*, 16(8), (1991), 967-972.

Gough, J, et al., "An Investigation Into the Effectiveness of Various Forms of Quadriceps Exercises", *Physiotherapy*, 57(8),, (1971), 356-361.

Haberichter, P. A., et al., "Muscle Pressure Effects on Motorneuron Excitability", (Abstract R-224), *Physical Therapy*, 65(5), (1985), p. 723.

Ibrahim, A., "Communicating in real-time on-line", *New Straits Times, Kuala Lumpar*, (Nov. 6, 1997), 5 pgs.

Kishino, N. D., et al., "Quantification of Lumbar Function—Part 4: Isometric and Isokinetic Lifting Simulation in Normal Subjects and Low-Back Dysfunction Patients", *Spine*, 10(10), (1985), 921-927.

Knapik, J., et al., "Angular Specificity and Test Mode Specificity of Isometric and Isokinetic Strength Testing", *The Journal of Orthopedic and Sports Physical Therapy*, 5(2), (1983), 58-65.

Krebs, D., et al., "Knee Joing Angle: Its Relationship to Quadriceps Femoris Activity in Normal and Postarthrotomy Limbs", *Arch Phys Med. Rehabil.*, vol. 64, (1983), 441-447.

Lieb, F. J., et al., "Quadriceps Function—An Electromyographic Study Under Isometric Conditions", *The Journal of Bone and Joint Surgery*, vol. 53-A(4), (1971), 749-758.

Lindh, M., "Increase of Muscle Strength From Isomeric Quadriceps Exercises at Different knee Angles", *Scand J Rehab Med.*, I I(1), (1979), 33-36.

Mayer, T. G, et al., "A prospective short-term study of chronic low back pain patients utilizing novel objective functional measurement", *Pain*, 25(1), (Apr. 1986), 53-68.

Mayer, T. G., et al., "Quantification of Lumbar Function—Part 2: Sagittal Plane Trunk Strength in Chronic Low-Back Pain Patients", *Spine*, 10(8), (1985), 765-772.

Million, R., et al., "Assessment of the progress of the back-pain patient 1981 Volvo Award in Clinical Science", *Spine*, 7(3), (May-Jun. 1982), 204-12.

Pollock, M. L., et al., "Chapter 22—Muscle", In: *Rehabiliation of the Spine: Science and Practice*, Hochschuler, S., et al., Editors, Mosby-Year Book, Inc., (1993), 263-284.

Rasch, P. J., "Progressive Resistance Exercise: Isotonic and Isometric: A Review", The *Journal of the Association for Physical and Mental Rehabilitation*, 15(2), (1961), 46-50.

Sikorski, J. M., et al., "A Rationalized Approach to Physiotherapy for Low-Back Pain", *Spine*, 10(6), (1985), 571-579.

Skurja, Jr., M., et al., "Quadriceps Action in Straight Leg Raise Versus Isolated Knee Extension", *EMG and Tension Study, Physical Therapy*, 60, (1980), p. 582.

Smidt, G., et al., "Assessment of Abdominal and Back Extensor Function—A Quantitative Approach and Results for Chronic Low-Back Patients", *Spine*, 8(2), (1983), 211-219.

Soderberg, G. L., et al., "An Electromyographic Analysis of Quadriceps Femoris Muscle Setting and Straight Leg Raising", *Phyiscal Therapy*, 63(9), (1983), 1434-1438.

Soderberg, G. L., et al., "Electromyographic Analysis of Knee Exercises in Healthy Subjects and in Patients with Knee Pathologies", *Physical Therapy*, 67(11), (1987), 1691-1696.

Stratford, P, "Electromyography of the Quadriceps Femoris Muscles in Subjects with Normal Knees", *Physical Therapy*, 62(3), (1981), 279-283.

Wild, J. J., et al., "Patellar Pain and Quadriceps Rehabilitation—An EMG Study", The *American Journal of Sports Medicine*, 10(1), (1982), 12-15.

"U.S. Appl. No. 10/854,400, Amendment and Response filed Apr. 29, 2013 to Non Final Office Action mailed Jan. 31, 2013", 11 pgs.

"U.S. Appl. No. 10/854,400, Examiner Interview Summary mailed Apr. 15, 2013", 3 pgs.

"U.S. Appl. No. 10/854,400, Non Final Office Action mailed Jan. 31, 2013", 14 pgs.

"U.S. Appl. No. 12/689,568, Final Office Action mailed Dec. 20, 2012", 20 pgs.

"U.S. Appl. No. 13/184,289, Final Office Action mailed Dec. 7, 2012", 21 pgs.

"U.S. Appl. No. 13/184,289, Preliminary Amendment filed Jan. 20, 2012", 8 pgs.

"U.S. Appl. No. 13/184,289, Pre-Appeal Brief Request filed Mar. 6, 2013", 4 pgs.

"U.S. Appl. No. 11/267,386, Notice of Allowance mailed Mar. 29, 2012", 10 pgs.

"U.S. Appl. No. 11/267,386, Supplemental Notice of Allowability mailed May 9, 2012", 7 pgs.

"U.S. Appl. No. 11/267,386, Supplemental Notice of Allowability mailed Jul. 18, 2012", 4 pgs.

"U.S. Appl. No. 11/494,719, Notice of Allowance mailed Apr. 18, 2012", 8 pgs.

"U.S. Appl. No. 12/689,568, Final Office Action mailed Apr. 25, 2012", 8 pgs.

"U.S. Appl. No. 13/184,289, Non Final Office Action mailed Jun. 8, 2012", 15 pgs.

"U.S. Appl. No. 10/854,400, Final Office Action mailed May 24, 2012", 9 pgs.

"U.S. Appl. No. 10/854,400, Final Office Action mailed Aug. 20, 2013", 13 pgs.

"U.S. Appl. No. 11/494,719, Notice of Allowance mailed May 29, 2013", 9 pgs.

"U.S. Appl. No. 12/689,568, Non Final Office Action mailed May 23, 2013", 22 pgs.

"U.S. Appl. No. 12/689,568, Response filed Sep. 20, 2013 to Non Final Office Action mailed May 23, 2013", 10 pgs.

"U.S. Appl. No. 13/184,289, Decision on Pre-Appeal Brief Request mailed Apr. 9, 2013", 2 pgs.

"U.S. Appl. No. 13/184,289, Non Final Office Action mailed Jun. 21, 2013", 25 pgs.

"U.S. Appl. No. 13/184,289, Response filed May 9, 2013 to Final Office Action mailed Dec. 7, 2012", 13 pgs.

"U.S. Appl. No. 13/536,660, Response filed Aug. 1, 2013 to Restriction Requirement mailed Jul. 15, 2013", 8 pgs.

(56) References Cited

OTHER PUBLICATIONS

"U.S. Appl. No. 13/536,660, Restriction Requirement mailed Jul. 15, 2013", 10 pgs.

"U.S. Appl. No. 13/611,232, Non Final Office Action mailed Aug. 22, 2013", 5 pgs.

"U.S. Appl. No. 13/611,232, Preliminary Amendment filed Sep. 12, 2012", 3 pgs.

"U.S. Appl. No. 13/611,232, Supplemental Preliminary Amendment filed Feb. 18, 2013", 7 pgs.

* cited by examiner

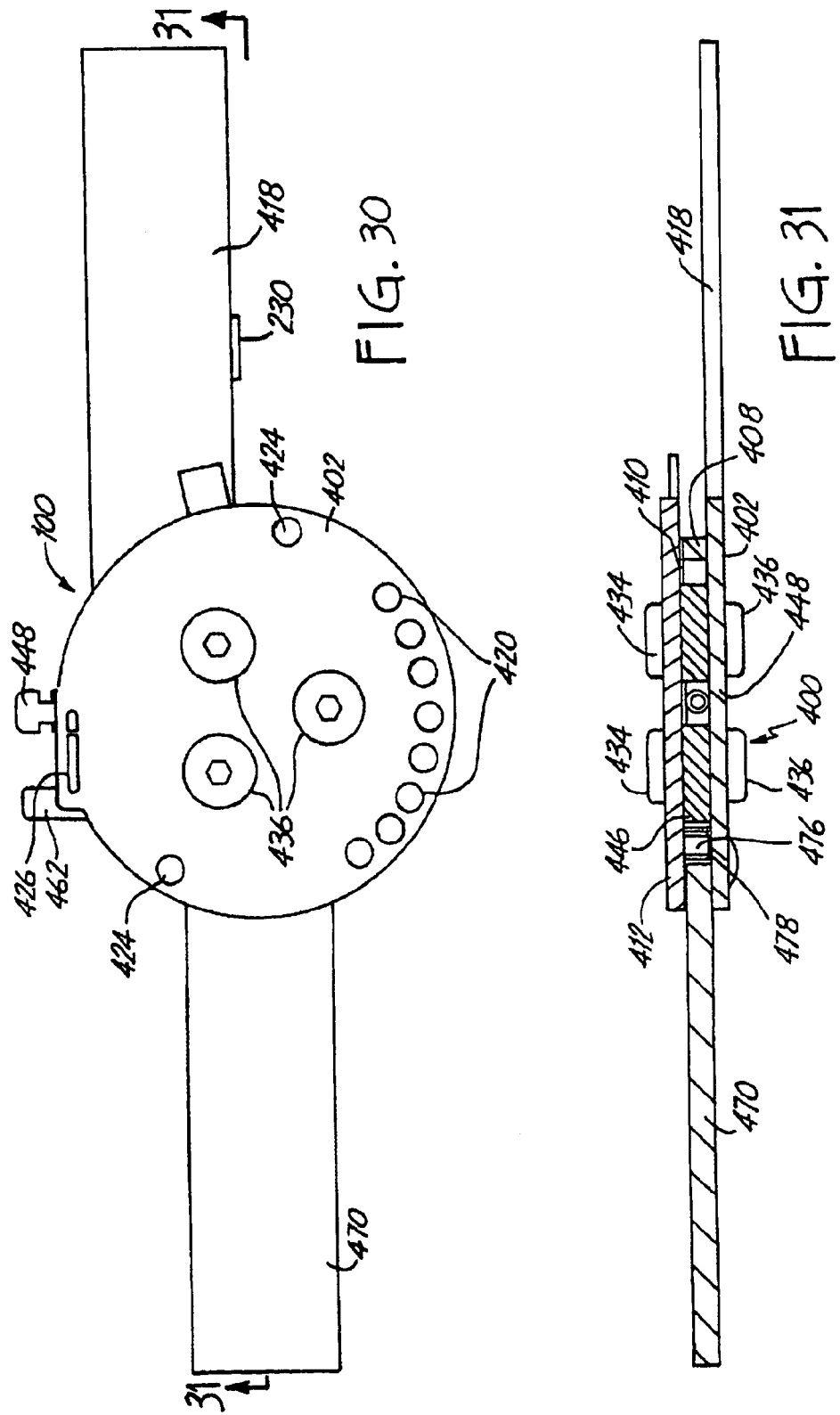

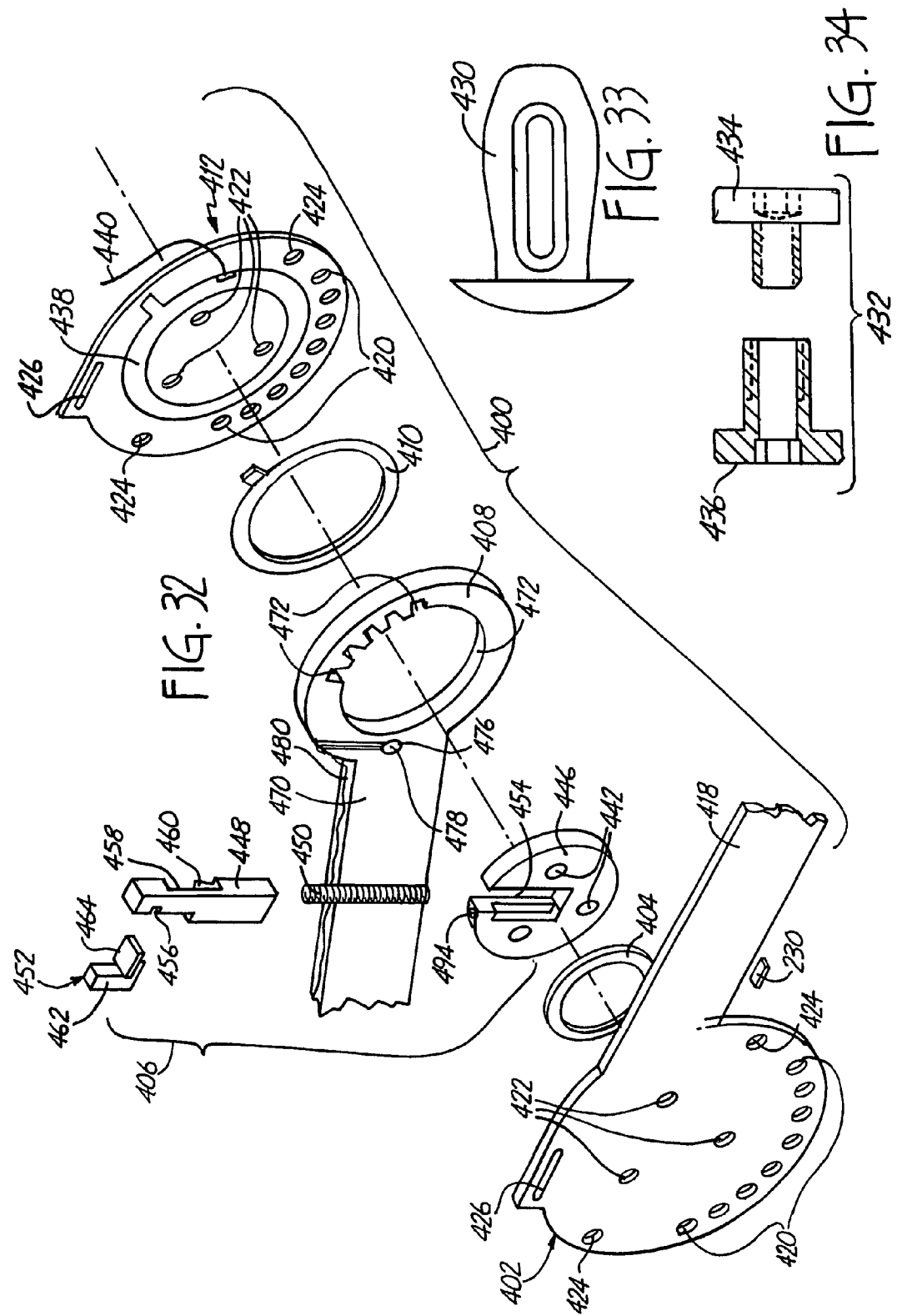

REMOTE MONITORING OF A PATIENT

CROSS REFERENCE TO RELATED APPLICATIONS

This application is a continuation of copending U.S. patent application Ser. No. 11/017,593, filed on Dec. 20, 2004, now abandoned, entitled "Orthoses for Joint Rehabilitation", which is a continuation of U.S. patent application Ser. No. 09/382,433 filed Aug. 25, 1999 to Stark et al., Now U.S. Pat. No. 6,872,187 to Stark et al., entitled "ORTHOSES FOR JOINT REHABILITATION, which claims priority to U.S. Provisional Application Ser. No. 60/098,779, entitled "ORTHOSES FOR JOINT REHABILITATION," filed on Sep. 1, 1998, all of which are incorporated herein by reference.

BACKGROUND OF THE INVENTION

The invention relates to orthoses useful for the rehabilitation of injured and/or weakened joints.

Both muscles and bones should be exercised to maintain strength. Also, bone fractures that are exposed to permissible weight bearing stress often heal more predictably and more rapidly than fractures that are not stressed at all. Improved healing based on application of appropriate stress is also believed to be true for connective tissue, such as ligaments and certain cartilage.

Suitable stress can be applied to the tissue by the performance of selected exercises. For example, isometric exercise generally involves the exertion of force against a relatively immovable object, which allows no motion of the limb. To perform isometric exercises, a restraining device can be used that has a substantially unchanging position for the duration of a particular exercise routine. Isotonic exercises involve exertion against the same weight or resistance through a range of motion. Isokinetic exercise is designed to mimic exertions that take place on a playing field or the like. When performing isokinetic exercises in a simulated environment, a machine is used to provide resistance in direct proportion to the exertion of the exerciser.

Isometric exercises are particularly useful with painful injuries to lower the risk of further injury. Also, because isometric exercises are performed in a static position, they allow very position specific therapy. For example, to climb stairs, a person needs more strength at an approximate 60° knee bend, when combined with the hip and ankle joints. Therefore, the isometric exercises can be designed to focus on the strengthening of a joint at optimum angles where additional strength is needed. If performed in a controlled manner, isometric exercises can be performed earlier in the recuperation period to speed recovery. As the patient's recovery progresses, isotonic exercises or other exercises can be used to reestablish a desired strength through a range of motion about a joint. As recovery progresses eventually the patient is able to perform a full range of exercises.

A difficulty with application of stress to an injured joint include a risk of inappropriately timed or excessive stress. This can impair healing and/or further injure the damaged tissues. Thus, exercises need to be carefully planned to provide appropriate amounts of stress. Also, the performance of the exercises should be monitored closely to reduce the risk of injury. Moreover, the need to carefully plan and closely monitor the exercises provides a cost and motivation barrier to accessing desirable amounts of exercise.

SUMMARY OF THE INVENTION

In a first aspect, the invention pertains to an orthosis comprising:

a first support portion that fits around a first body portion on a first side of a patient's joint;

a second support portion that fits around a second body portion, the second body portion being on the opposite side of the joint from the first body portion;

a hinge connecting the first support portion and the second support portion; and a resistance applicator connected to the hinge to provide resistance to rotation of the hinge, the resistance applicator comprising:

a first surface;

a second surface generally parallel to the first surface and selectively movable relative to the first surface;

a crank that is located between the first surface and second surface and that is rotatable relative the first surface; and a compression unit located between the first surface and the second surface, the compression unit applying resistance with respect to the rotation of the crank relative to the first surface with the amount of resistance being related to the distance of the first surface to the second surface.

The first body portion and the second body portion can be connected by way of a plurality of joints. The compression unit can include a plurality of crank rings interspersed with and in frictional contact with a plurality of housing rings, where the crank rings rotate with the crank and the housing rings rotate with the first surface.

In another aspect, the invention pertains to an orthosis comprising:

a first support portion that fits around a first body portion on a first side of a patient's joint;

a second support portion that fits around a second body portion, the second body portion being on the opposite side of the joint from the first body portion;

a hinge connecting the first support portion and the second support portion; and a resistance applicator applying selective resistance to rotation about the hinge;

a strain sensor operably connected to the first support portion; and a controller calibrated to measure the force applied to rotate the hinge using the electrical resistance of the strain sensor.

In preferred embodiments, the controller includes a digital microprocessor.

Moreover, the invention pertains to a method of performing closed chain exercises, the method comprising:

applying force against a force transducer with a repetition rate and force target specified with a digital microprocessor-based portable controller, the force transducer being held fixed in space by forces external to the patient;

measuring the force applied to the force transducer using the controller, the controller being operably connected to the force transducer; and displaying the force applied to the force transducer.

The digital microprocessor can be used to calculate relative forces within the physiological tissue of the patient.

In a further aspect, the invention features a method of performing coordination exercises for neuromotor training comprising:

flexing a joint such that a cursor on a display moves to reach a target position on the display at a selected, prescribed time, the motion of the cursor being correlated with the motion or strain of the joint by way of a sensor in an orthosis placed around the joint.

In some embodiments, the orthosis comprises:

a first support portion that fits around a first body portion on a first side of the joint;

a second support portion that fits around a second body portion, the second body portion being on the opposite side of the joint from the first body portion;

a flexible connection connecting the first support portion and the second support portion;

a position sensor operably connected to the flexible connection such that the position sensor detects the relative orientation of the first support portions with respect to the second support portion.

The position sensor can be operably connected to a controller, preferably with a digital microprocessors. Alternatively, lower cost analog decision array with resistor networks connected to a meter, light bank or audible output feedback could be used. A suitable analog controller for this purpose is an LM3914 integrated circuit LED driver.

Moreover, the invention pertains to an instrumented exercise device comprising:

an elastic cord;

a transducer connected to the elastic cord such that forces applied to the cord alter output from the transducer; and a display operably connected to the transducer.

The transducer and display can be connected to a digital microprocessor. The microprocessor can further be used to perform calculations and statistical analyses based on the output of the transducer.

Furthermore, the invention pertains to an instrumented exercise device comprising:

a frame comprising two lever arms connected at a joint;

a transducer connected to the frame such that torsional forces applied against the frame are measured by the transducer; and a display operably connected to the transducer.

In a further aspect, the invention pertains to a kit comprising:

two hinges;

two frame elements extending from each hinge such that relative motion of the frame elements extending from one of the hinges rotates that hinge;

four sleeves where the sleeve receives and holds fast a frame element, where each sleeve attaches to a body part cover;

a strain sensor connected to a frame member; and a controller that displays a reading related to the strain measured by the strain sensor.

The controller can include a microprocessor. The sleeves can releasably hold a corresponding frame element. Alternatively, the sleeves can irreversibly hold a corresponding frame element and wherein the sleeve can be cut without damaging the frame element.

Additionally, the invention pertains to an orthosis comprising:

a hinge;

two frame elements extending from the hinge such that relative motion of the frame elements extending from the hinge rotates the hinge;

two sleeves, where a sleeve receives and holds fast a frame element;

two disposable rigid body part covers, one body part cover fitting over a body part on one side of a patient's joint and the second body part cover fitting over a body part on the second side of a patient's joint;

a strain sensor connected to a frame member; and a controller that displays an output related to the strain measured by the strain sensor.

Moreover, the invention pertains to an orthosis comprising:

a first support portion that fits around a first body portion on a first side of a patient's joint;

a second support portion that fits around a second body portion, the second body portion being on the opposite side of the joint from the first body portion; and a hinge connecting the first support portion and the second support portion, the hinge having a locking mechanism that is released by depressing a button.

The orthosis can further include a slide member that can releasably hold the button in the depressed, unlocked position.

In addition, the invention pertains to an orthosis comprising:

a first support portion that fits around a first body portion on a first side of a patient's joint;

a second support portion that fits around a second body portion, the second body portion being on the opposite side of the joint from the first body portion;

a flexible connection connecting the first support portion and the second support portion; and a securing cuff connected to one of the support portions, where the securing cuff can be reversibly tightened around the corresponding body portion at a narrowing section of the skeletal system to inhibit the motion of the support portions relative to the body portions.

In another aspect, the invention pertains to a strain measuring circuit comprising:

a strain sensor;

a signal conditioner that biases the strain sensor with a known voltage and amplifies the biased signal so that the variable resistance of the strain sensor due to applied stress is output as an analog signal;

an analog-to-digital converter receiving the output of the signal conditioner;

a digital processor that receives the output of the analog-to-digital converter and that evaluates the error of the strain measurement based on the precision of the analog-to-digital converter and the properties of the signal conditioner to set an output signal to a digital-to-analog converter to adjust the reference of the strain measurement to bring the error of the measurement to within tolerance values; and a digital-to-analog converter receiving a digital output from the digital processor and outputting an analog signal as a reference signal to the signal conditioner.

Furthermore, the invention pertains to a method of calibrating a strain measurement comprising:

incorporating a strain sensor into a summing amplifier circuit, where the summing amplifier circuit performs the amplification based on a value input from a digital-to-analog converter;

digitizing the output of the summing amplifier circuit using an analog-to-digital convertor;

estimating the error of the strain measurement based on the number of bits of the output of the analog-to-digital convertor and the gain of the amplifier circuit;

determining if the estimate error is within tolerance values; and altering the output to the digital to analog converter if the error estimate is outside of tolerance values.

In a further aspect, the invention pertains to a joint force applicator comprising:

a force applicator that applies a correction force to a joint when placed around the joint;

a force distributor that distributes the force opposing the correction force such that the correction force applies a shear force at the joint to change joint alignment during motion involving the joint;

a force transducer measuring a quantity related to the correction force; and a processor displaying a value related to the correction force. The processor can be analog, or the processor can be a digital processor. The force distributor can comprise a strap, and the force transducer can comprise a strain sensor operably connected to the strap. The force transducer can include a pressure sensor operably connected to the force applicator.

In another aspect, the invention pertains to an orthosis comprising:
a first support portion that fits around a first body portion on a first side of a patient's joint;
a second support portion that fits around a second body portion, the second body portion being on the opposite side of the joint from the first body portion;
a flexible connection connecting the first support portion and the second support portion;
a position sensor operably connected to the flexible connection such that the position sensor detects the relative orientation of the first support portions with respect to the second support portion; and
and a microprocessor based portable controller connected to the position sensor, where the first support portion and the second support portion each have a connection for attachment to a continuous passive motion device. The orthosis can further include a continuous passive motion (CPM) device, the CPM device including a motor and a frame with matched connectors for attachment to the first support portion and the second support portion and the frame being operably connected to the motor such that motion of the motor moves the frame and moves the first support portion relative to the second support portion.

In addition, the invention pertains to a method of evaluating an exercise program or the patient's response to the injury comprising:
prompting responses by the patient to a series of inquiries using a portable controller; and
evaluating the condition of the patient in an exercise program by examining the responses to the questions.

The prompting of responses to the questions can occur away from a health care facility. The questions can relate to the pain felt by the patient.

In another aspect, the invention pertains to a method for programming a portable controller to guide a patient through an exercise routine, the method comprising:
downloading a program to the portable controller from a computer, wherein the program is assembled by the computer based on exercise parameters entered into the computer by a health care professional.

In a further aspect, the invention pertains to a monitoring station comprising:
a digital computer programmed to assemble a microprocessor program for a microprocessor based controller according to parameters entered into the digital computer upon prompting by the digital computer; and
a port configured to download the microprocessor program to the controller.

In addition, the invention pertains to an instrumented hinge comprising:
a first lever arm;
a second lever arm;
a biaxial hinge connecting the first lever arm and the second lever arm, the biaxial hinge including a position sensor providing an output related to the relative orientation of the first lever arm and the second lever arm, the biaxial hinge having two coupled rotational axes; and
an output device connected to the position sensor of the biaxial hinge.

The position sensor associated with the biaxial hinge and the display can be connected to a digital microprocessor. One or both lever arms connected to the biaxial hinge can include strain sensors. Also, the instrumented biaxial hinge can be incorporated into an instrumented orthosis comprising:
a first support portion that fits around a first body portion on a first side of the joint;
a second support portion that fits around a second body portion, the second body portion being on the opposite side of the joint from the first body portion;
a biaxial hinge connecting the first support portion and the second support portion, the biaxial hinge including a position sensor providing an output related to the relative orientation of the first support portion and the second support portion, the biaxial hinge having two coupled rotational axes; and
an output device connected to the position sensor of the biaxial hinge.

Furthermore, the invention pertains to an orthosis comprising:
a first support portion designed for external fixation to a body portion on a first side of a joint;
a second support portion designed for external fixation to a second body portion, the second body portion being on the opposite side of the joint from the first body portion;
a connector joining the first support portion and the second support portion;
a transducer connected to the lever arms such that torsional forces are measured by the transducer; and
an output device operably connected to the transducer.

BRIEF DESCRIPTION OF THE DRAWINGS

FIG. 30 is a side view of a hinge suitable for use with the resistance applicator of FIG. 15.

FIG. 31 is a sectional view of the hinge of FIG. 30 taken along line 31-31.

FIG. 32 is an exploded, perspective view of the hinge of FIG. 30.

FIG. 33 is side view of a stop pin useful with the hinge of FIG. 30.

FIG. 34 is a side view of a barrel bolt used for securing the hinge of FIG. 30.

Figures 59, 60, 61:
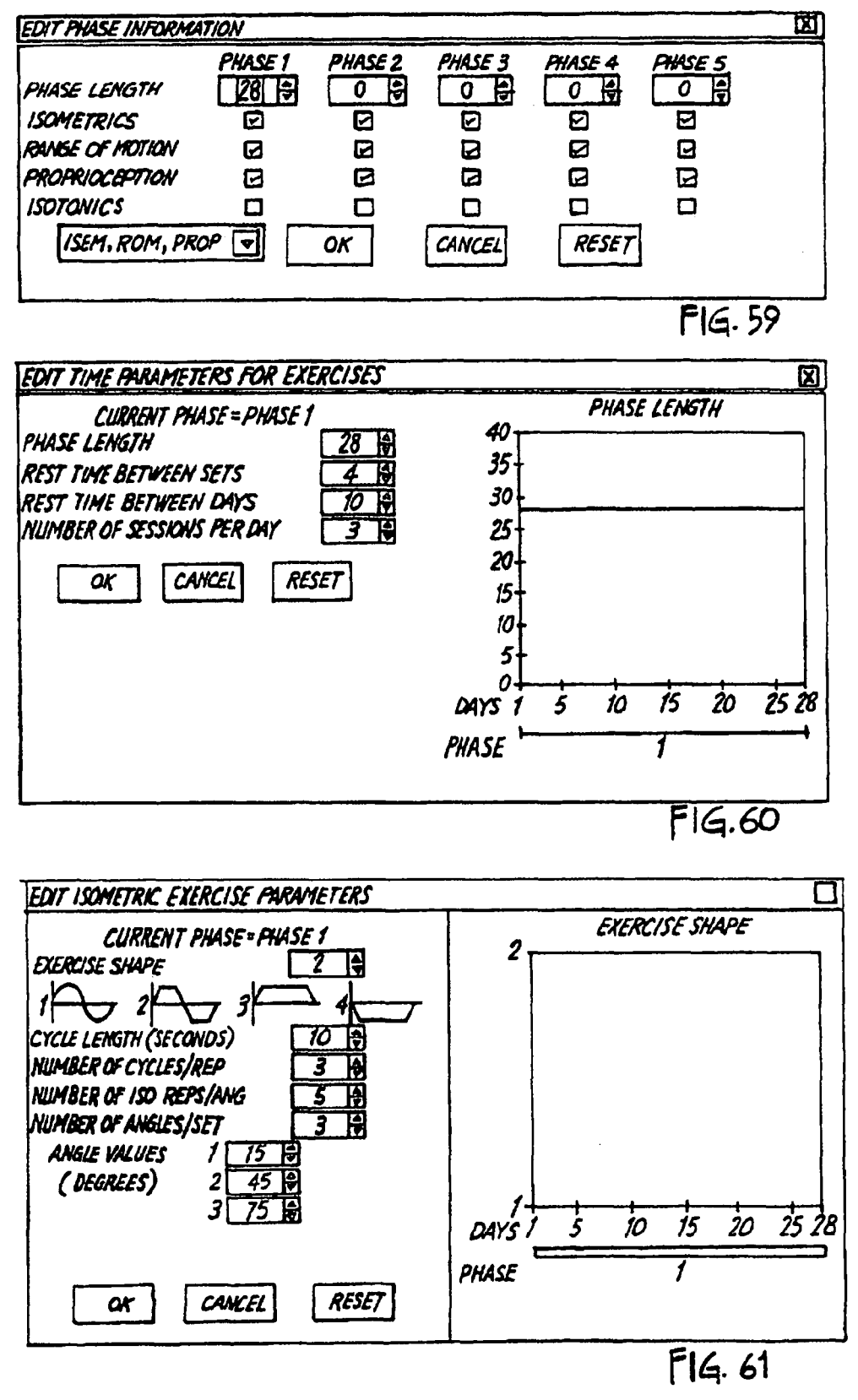

FIG. 59 is a schematic depiction of a computer screen window prompting a health care professional at a monitor station to select exercises routines.

FIG. 60 is a schematic depiction of a computer screen window depicting the entry of exercise time parameters into the monitor station.

FIG. 61 is a schematic depiction of a computer screen window depicting the entry of isometric exercise parameters into the monitor station.

DETAILED DESCRIPTION OF THE PREFERRED EMBODIMENTS

Figure 1:
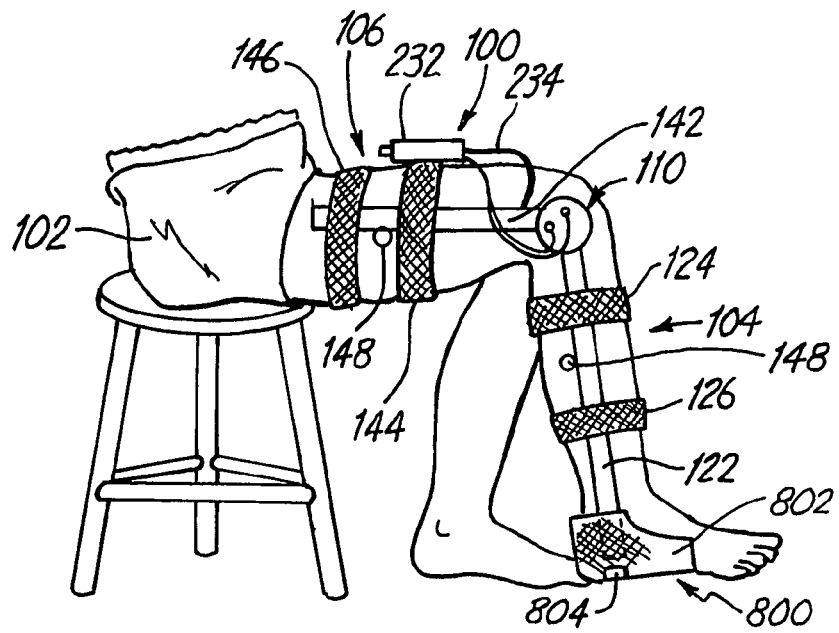
FIG. 1 is a side view of an embodiment of an orthosis mounted around the knee of a patient.

Orthoses can be used effectively to speed the rehabilitation of an injured and/or weakened joint of a patient. In particular, an orthosis can include a microprocessor to monitor and assist with the performance of exercises. The microprocessor can also track the patient's performance and provide a means of reporting the performance to a central collecting station or a health care professional. Important features have been identified that provide for efficient use of a microprocessor monitored orthosis. By simplifying the use of a rehabilitation orthosis through microprocessor instruction to the patient as well as simplifying and improving monitoring of the exercises, accessibility to useful levels of rehabilitative exercise is greatly enhanced. Some of the improved features can be used effectively in improved orthoses even without having microprocessor control.

Relevant orthosis fit around the joint of a patient, i.e., flexibly connected body portions. The orthosis can be designed to fit around any joint or series of joints including, for example, the knee, wrist, ankle, hip, elbow, shoulder, spine/back. Generally, the orthosis includes a plurality of support portions connected by a hinge or comparable connection. At least one support portion fits on one body portion on one side of a joint, while one or more other support portions fit on a second body portion on the other side of the joint. The hinge can have a conventional design or one of the improved designs described below. One or more support portions can be secured to the patient with the use of an external fixator or other similar attachment approach.

Relevant orthoses can be used to assist with one or more rehabilitation procedures. In particular, the orthosis preferably is useful to monitor the performance of isometric exercises. Isometric exercises generally can be performed relatively early in the rehabilitation of an injured and/or weakened joint. In other preferred embodiments, the orthosis also can monitor the performance of range-of-motion exercises, proprioception exercises, isotonic exercises and/or closed chain exercises. Similarly, the orthosis can be designed to apply and monitor selective pressure to reduce forces applied to worn components of joints.

Some preferred embodiments include an additional component to provide for closed chain exercises when used with the joint supporting component. Closed chain exercises involve muscular motion against resistance to mimic natural motions or to provide balanced stresses to the joint. Closed chain exercises can be contrasted with open chain exercises where a limb or the like is moved or stressed in space without any resistance against the motion other than perhaps the weight of the limb itself. Closed chain exercise may provide more balanced exercise of the various muscle groups within a patient's limb or trunk. The closed chain component may or may not be physically connected with the joint supporting orthosis components.

A strain sensor or strain gauge can be used to make measurements of isometric exercises by measuring stress within the orthosis. Several design features of the controller can be used to obtain useful strain measurements using relatively inexpensive hardware. These features are described below.

The coordination of the exercise routine preferably is handled by a microprocessor based controller that assists by prompting the patient for the performance of an exercise routine and by monitoring the routine. Generally, the controller is programmed with a target exercise routine selected by a health care professional. The controller assists the patient with the performance of the exercise by providing immediate feedback with respect to evaluating the performance of the exercises relative to the target routine. The controller may store selected information on the patient's performance of the exercises. This information can be downloaded for evaluation of compliance and performance by a health care professional.

Alternative instrumented exercise devices include an instrumented abduction/adduction exerciser and an instrumented therapeutic resistance (stretch) cord. These instrumented exercise devices can be used alone or in combination with an instrumented orthosis. Instrumentation of these exercise devices provides for the monitoring and evaluation processes used with the instrumented orthosis.

1. Orthosis Construction

A relevant orthosis includes a joint support component, one or more transducers, a control unit and, optionally, additional treatment component or components. Generally, the entire orthosis is portable in the sense that the joint support component can be supported completely by the corresponding body portions of the patient while the patient is mobile. Thus, the orthosis like a cast or the like is ambulatory, i.e., carried by the patient during their activities. Any additional treatment components may or may not be physically connected with joint support component. The joint support component includes support portions joined by a flexible connection or hinge.

A relevant orthosis generally includes, at least, one support portion attached on opposite side of the joint. The one or more support portions on one side of a joint are connected to the one or more support portions on the other side of the joint by a flexible connection. The flexible connection preferably is selectively flexible such that the flexible connection can be locked in a particular configuration. Of course, a suitable orthosis can cover more than a single joint, especially with a back orthosis. Nevertheless, elements can be identified as support portions if by no other feature than being the last on either end of a set of articulating elements comprising the orthosis. The support portions can have a variety of structures.

Figure 2:
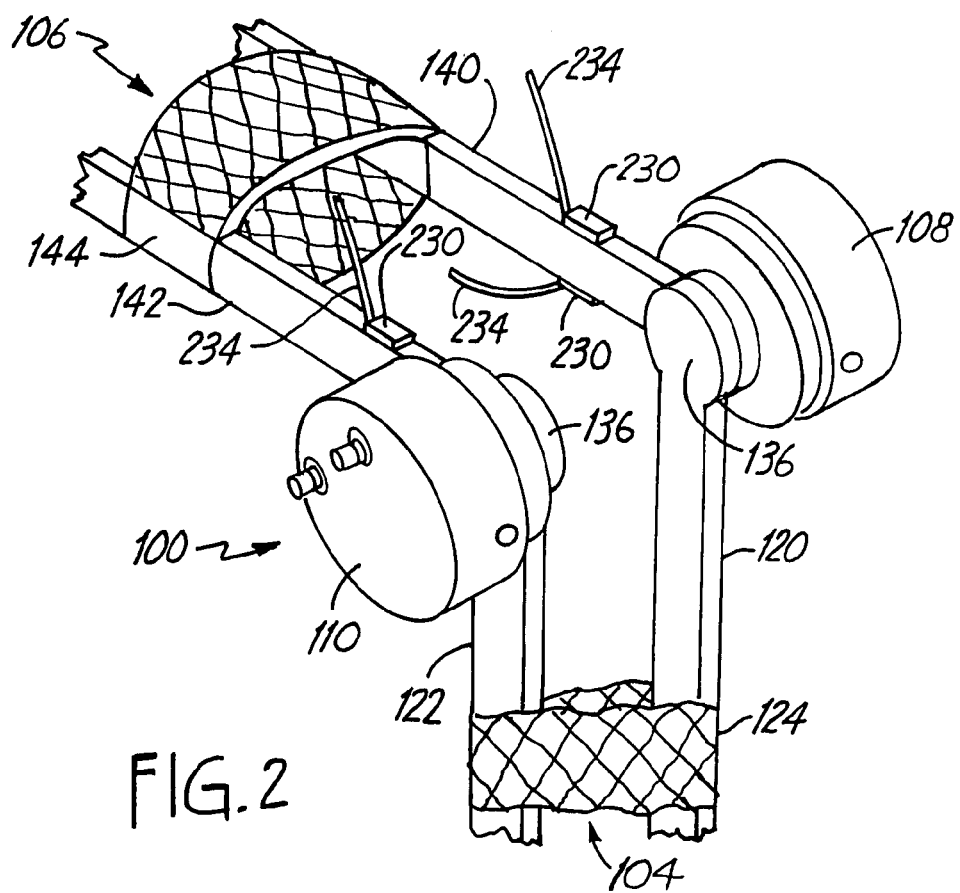
FIG. 2 is a fragmentary, perspective view of the orthosis of FIG. 1 removed from the patient.

FIGS. 1 and 2 display one embodiment of an orthosis or brace 100 shown on a patient 102. Orthosis 100 includes support portions 104, 106 connected by hinges 108, 110. The hinges can be mechanical, electromechanical or a combination thereof, as described further below. Support portion 104 includes a left frame member 120 and a right frame member 122 connected by flexible straps 124, 126.

Frame members 120, 122 generally are constructed from rigid materials such as steel, aluminum, other metals or alloys, fiberglass, composites, other similar materials, or combinations thereof. Flexible straps 124, 126 preferably are adjustable such that the support portion 104 can be fit to the patient. Adjustment of flexible straps 124, 126 can be performed with hook and loop fasteners or any of a variety of other fasteners including conventional fasteners. Flexible straps 124, 126 can be replaced in alternative embodiments by sheets of fabric or the like which can be adjusted with hook and loop fasteners or other fasteners including conventional fasteners. Similarly, support portion 106 includes a left frame member 140 and a right frame member 142 connected by flexible straps 144, 146.

Support portions 104, 106 can include connections 148 for attachment to Continuous Passive Motion (CPM) devices, for example, on frame members 120, 122, 140 and 142. Any of a variety of possible connections can be used that can transfer the force from the CPM device to the frame of the orthosis without damaging the orthosis. Suitable connections can be made with any of a variety of releasable fasteners such as snaps, clips, pivots and the like. CPM devices are passive in the sense that motors are used to flex joints. CPM devices can be useful in combination with an isometric exercise device since CPM devices can flex the joint over a particular range of motion when the muscles have not yet healed sufficiently to perform comparable motions actively. The corresponding CPM machine would have the appropriate component of the connector for attachment to the orthosis. The CPM machine can be connected to the controller for orthosis 100. The controller can be used to control the motor speed and the like. The connection can be by way of a RS232 connection, infrared connection, radio connection or the like.

Figure 3:
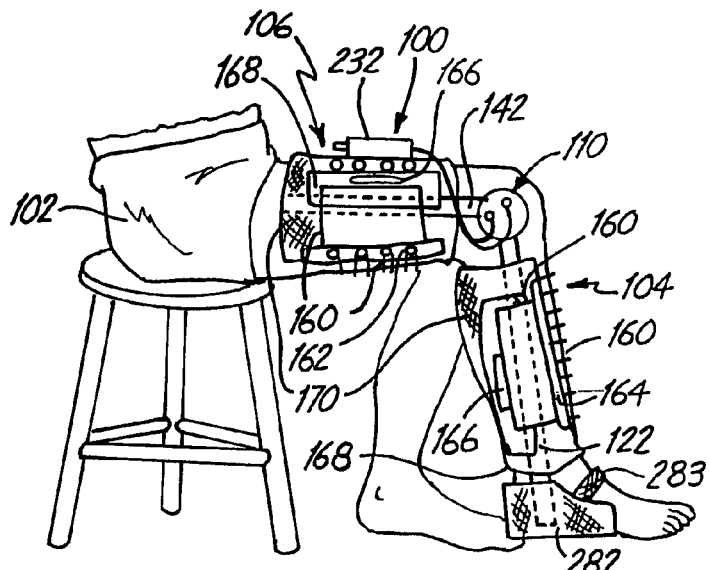
FIG. 3 is a side view of an alternative embodiment of an orthosis with a cord-based fastener using pulleys.

Another alternative embodiment for replacing straps 124, 126 is shown in FIG. 3. A cord based adjustable fastener includes cords 160 winding between pulleys 162. Pulleys 162 can be covered with pulley covers 164. Cords 160 extend to handles 166. Handles 166 include hooks that attach to corresponding loop sheets 168 on fabric covers 170 that wrap partly around the corresponding body portion. Selected placement of the handle with the hook and look fastener provides for a desired degree of constriction of the orthosis. The configuration of the hook and loop fasteners can be reversed with the loop associated with handles 164. Instead of using a handle to manually tighten or loosen the cord, a motor can be used to adjust the tension. Such a motorized, cord based adjustment was described for use in a back brace in U.S. Pat. Nos. 5,226,874 and 5,346,461, to Heinz et al., both of which are incorporated herein by reference.

Figure 4:
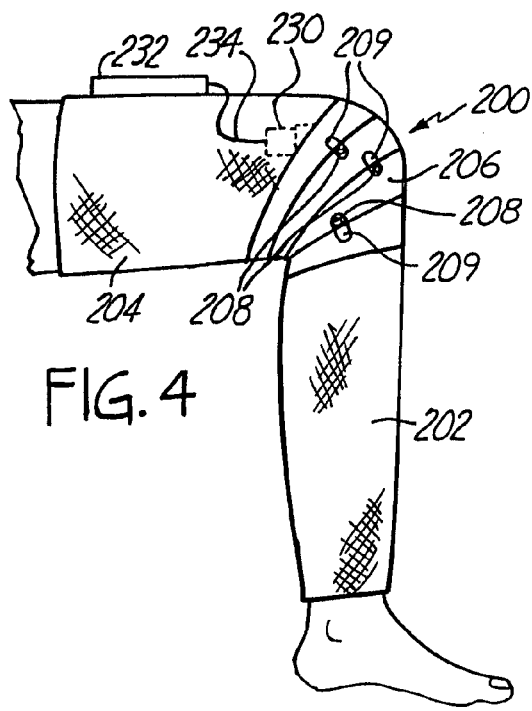
FIG. 4 is a side view of an embodiment of an orthosis with rigid shell support portions and an articulating hinge integrated with the support portions.

In an alternative embodiment of the orthosis 200, support portions 202, 204 involve extended elements that fit the appropriate body portion, as shown in FIG. 4. Support portions 202, 204 generally are rigid and can be constructed from a variety of materials. Preferred materials for the construction of support portions 202, 204 include, for example, molded plastic shells, plaster, heat moldable thermoplastics, water-activated fiberglass, heat shrink plastic and other cast forming materials. Support portions 202, 204 can be premolded in various sizes such that a particular size is selected based on measurements of the patient. Alternatively, support portions 202, 204 can be constructed to fit a particular patient. These custom molded support portions are molded to fit the body portions of the particular patient by a trained physician or technician.

Figure 5:
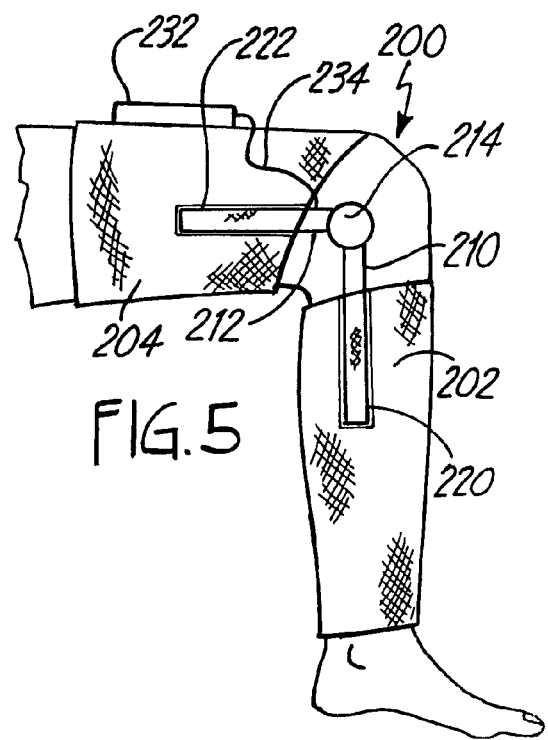
FIG. 5 is a side view of an embodiment of an orthosis with a rigid shell support portions and a hinge connected to the frame elements.

As shown in FIG. 4, support portions 202, 204 are connected by an articulating hinge 206. Articulating hinge 206 can be made with resilient collapsible materials such as a bendable straw, sliding sections that can slide past each other to articulate, or other similar constructions. Sliding sections can be locked relative to one another by way of clamps 208 attached to slots 209 defining a range of motion, where the clamps are tightened manually with wing nuts or the like, or electronically with solenoids or the like. Referring to FIG. 5, in an alternative embodiment support portions 202, 204 are connected with right frame elements 210, 212. Right frame elements 210, 212 are connected by a right hinge 214. Comparable left frame elements and left hinge on located on the opposite side of the patient's joint.

Right frame elements 210, 212 and the corresponding left frame elements can be molded into the support portions 202, 204 when the support portions are formed. In some preferred embodiments, sheaths 220, 222 are molded into support portions 202, 204. Right frame elements 210, 212 lock into sheaths 220, 222 such that right frame elements 210; 212 are held firm relative to support portions 202, 204. For example, the sheath can include a flange that allows a series of ridges to pass in a single direction such that the frame element fits into the sheath but cannot be removed. Similar lock elements are used plastic ties. Alternatively, a reversible locking mechanism can be used, for example, where a lock pin or the like is inserted through the sheath and into the frame element.

Right frame elements 210, 212 can be disengaged from sheaths 220, 222 either by disengaging a locking mechanism or by destroying the sheath 220, 222. Sheath 220, 222 can be constructed from an inexpensive but durable polymer. Thus, frame elements 210, 212 and hinge 214 can be reused in another orthosis. Comparable attachments would be used to secure the left side of the support portions. Right hinge 214, right frame elements 210, 212, sheaths 220, 222 can be placed into a kit. Generally, the kit would further include the corresponding left elements and/or a strain sensor and controller, as described below. The kit preferably would be placed within a single package although multiple packages can be used if desired.

In preferred embodiments, the orthosis includes one or more strain sensors. The strain sensors are useful for the performance and monitoring of isometric exercises with a selectively flexible connection/hinge in a locked position. Also, the strain sensor is useful for the measurement of forces during isotonic exercises. The strain sensors generally are located on a rigid element that is under stress when torque is applied to the selectively flexible connection/hinge. Thus, the preferred locations for the strain sensors depend on the particular construction of the orthosis. Referring to FIG. 2, strain sensors 230 are attached to frame members 140, 142. Strain sensors 230 can be connected to controller 232 (FIG. 1) by way of wires 234. Alternatively, strain sensors can be connected to controller 232 by way of some form of telemetry. Referring to FIG. 4, strain sensor 230 is attached to support portion 204.

When forces are applied by the patient against the orthosis, the orthosis tends to change position relative to the patient's joint. This shifting reduces the effectiveness of exercises being performed with the orthosis and may necessitate realignment of the orthosis for proper fit. The orthosis can be designed to reduce or eliminate this shifting.

Figure 6:
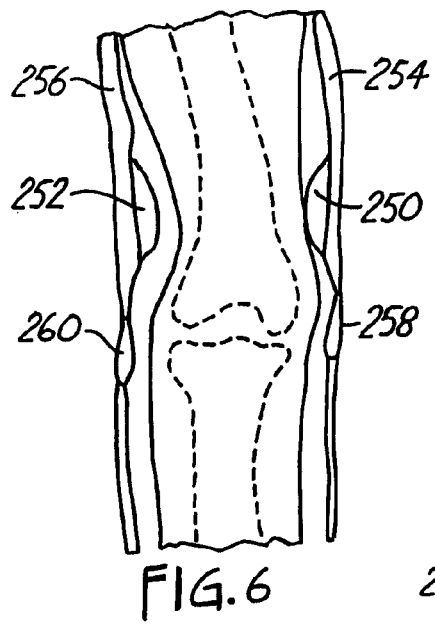
FIG. 6 is a front view of an orthosis around the knee of a patient, where the orthosis has protuberances to resist motion of the orthosis during exercises.
Figure 10:
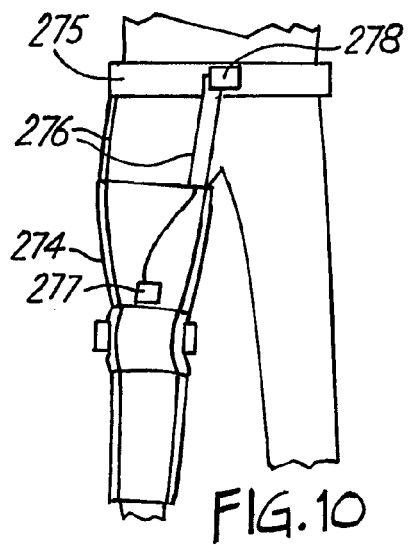
FIG. 10 is a perspective view of an orthosis around the knee of a patient, where the orthosis is attached to a belt to help hold the orthosis in place during exercises and activities such as walking.

A first approach to prevent a knee orthosis from slipping during exercise is to construct the orthosis with indentations 250, 252 in the femur supracondylar area just above the knee, as shown schematically in FIG. 6. Preferably, the orthosis is instrumented. To further improve the contact of the orthosis with the patient, a two sided adhesive pad can be applied to the patient, such as at indentations 250, 252. In this embodiment, the indentations or formed off of frame elements 254, 256 projecting above hinges 258, 260. Similar indentations can be used with other orthosis constructions and with orthoses designed for other joints such that the orthosis grips the underlying bone structure.

Figure 7:
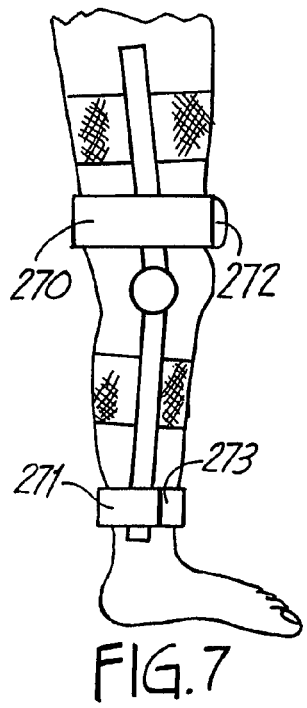
FIG. 7 is a side view of an orthosis around the knee of a patient, where the orthosis has binding straps to hold the orthosis in place during exercises.
Figure 8:
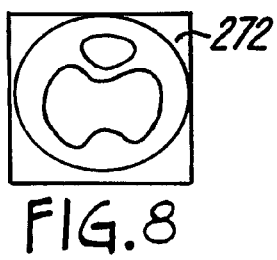
FIG. 8 is a rear view of a first gripping element in the orthosis of FIG. 7.
Figure 9:
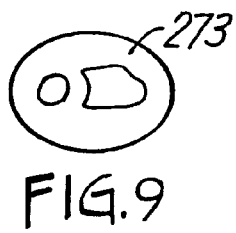
FIG. 9 is a rear view of a second gripping element of the orthosis of FIG. 7.

Referring to FIGS. 7-9, an alternative solution involves the use of additional securing cuffs 270 and/or 271. Securing cuffs 270, 271 are designed to be tightened more during exercise routines to help secure the orthosis relative to the joint. Cuff 270 includes a gripping element 272. The under side of gripping element 272 to be placed against the leg above the knee preferably has a semiquadrangular shape such that when tightened, gripping element 272 applies pressure above the kneecap and pushes on the knee without pushing on the vasculature and lymphatic drainage posteriorly. Cuff 271 includes gripping elements 273 placed on both sides of the shin just above the ankle. Cuff 271 steadies the orthosis from below. Cuffs 270, 271 can be tightened with a variety of fasteners including hook and loop fasteners and can include a pulley or quick ratchet system similar to that shown in FIG. 3. Alternatively, the cuffs can be tightened using a lever with a fulcrum in the middle and a strap on the bottom such that the strap tightens when the lever is moved from one side of the fulcrum to the other.

Another approach to securing the orthosis involves securing the orthosis 274 to a belt 275 by way of one or more straps 276. In preferred embodiments, straps 276 and belt 275 provide a path for electrical communication between electronic elements 277 and electronic elements 278 on belt 275. Straps 276 can be secured using hook and loop fasteners, hooks or any other reasonable fastener.

Figure 11A:
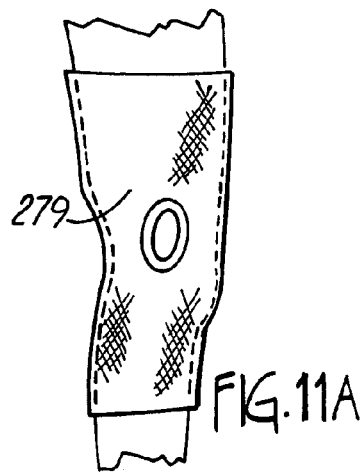
FIG. 11A is a front view of a high friction sleeve worn around the knee over which an exercise orthosis can be placed.
Figure 11B:
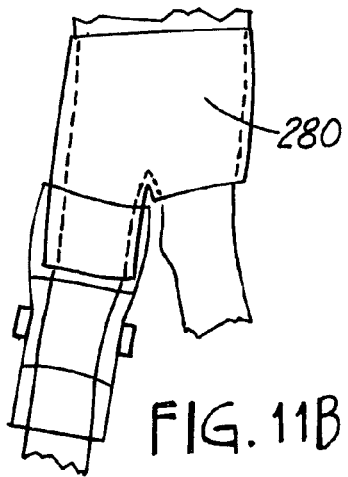
FIG. 11B is a front view of a high friction undergarment worn by a patient, where an exercise orthosis around the knee of the patient lies on top of a portion of the undergarment.

Still another approach involves increasing the friction of the surface contacting the orthosis or part of the orthosis. For example, in FIG. 11A a polymer sleeve 279 is worn around the knee and the orthosis would be placed over sleeve 279. Sleeve 279 can be made from a sheet or mesh of neoprene. The orthosis is secured to sleeve 279 using hook and loop fasteners, snaps or ribbing or the like for frictional securing. Similarly, as shown in FIG. 11B underwear 280 with high friction extending down to cover all or part of the area over which an orthosis is placed helps to reduce movement of the orthosis.

Figure 12:
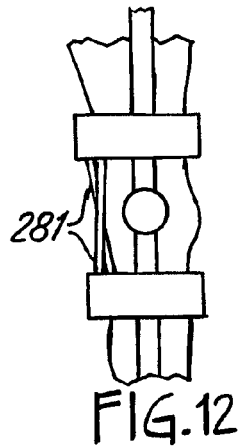
FIG. 12 is a side view of an orthosis secured with cross straps behind the fold of the knee.

Referring to FIG. 12, another approach to securing the orthosis involves the placement of crossed straps 281 behind the knee. Straps 281 apply forces that tend to maintain straps 281 in the fold of the knee. Furthermore, for a knee orthosis, the orthosis can end with a heel cup 282 or stirrup with a strap 283 or the like around the foot to hold the bottom of the orthosis around the heel of the foot. The knee orthosis is secured to heel cup 282 with appropriate connectors to fix the position of the hinge at the knee, as shown in FIG. 3. Similar anchor-type structures can be placed on orthoses covering other body parts to resist shifting of the orthosis.

With any of these approaches for inhibiting orthosis motion during use, the method preferably distributes the restraining forces sufficiently such that no portion of the skin is subject to excessive pressures that could bruise the skin as well as damage or interfere with neural or circulatory functions.

The instrumented orthoses described above involve an external framework that surrounds a patient's joint. The orthoses are appropriately designed to secure comfortably the orthosis around the joint and to resist movement of the orthosis when forces are applied to the orthosis. As an alternative to the use of an instrumented orthosis surrounding the respective body portions, the instrumented orthosis can include one or more rigid attachments to the patient. These alternative forms of the orthosis use structures such as external fixators or the like for attachment. External fixators have been used to secure broken bones and to reduce fractures by attaching an external, rigid frame to a patient's bone with pins. When integrated into the instrumented orthoses described herein, the structure of an external fixator involves the attachment of the external frame to one or more hinge elements. Suitable hinge elements for use in orthoses with an external fixator structure are the same as those hinge elements that are suitable in orthoses with a purely external framework.

Figure 13:
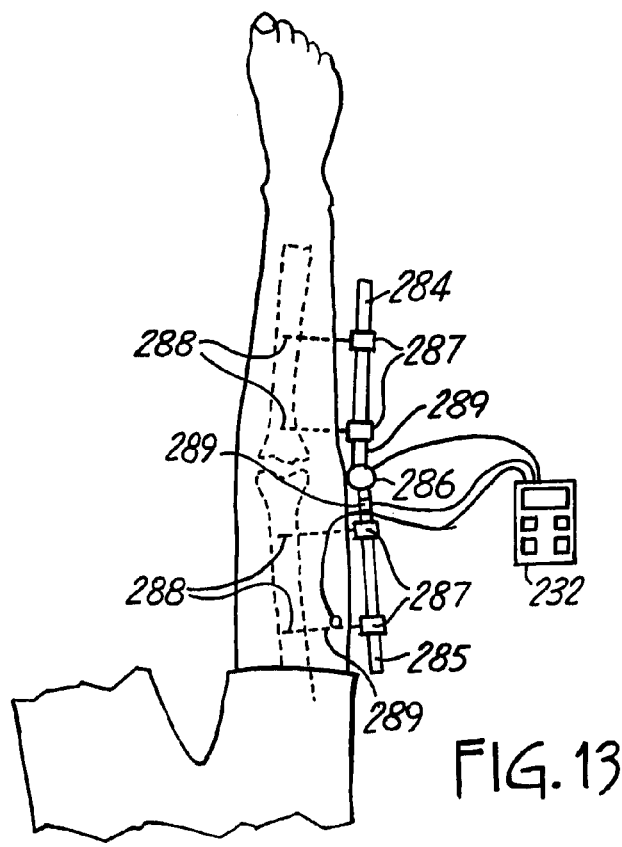
FIG. 13 is a fragmentary, top view of an instrumented intermediary segment secured to the patient with pins using features of an external fixator.

A first embodiment of an instrumented orthosis secured with features of an external fixator is depicted in FIG. 13. Frame elements 284, 285 are connected with a connector 286. Connector 286 can be a flexible connector such as a hinge, or a rigid connection that holds the first support portion and the second support portion at a fixed angle. If connector 286 is a hinge, the hinge can include fasteners for the attachment of a removable resistance element. Alternatively, the hinge can include an intrinsic resistance element. The resistance element preferably proved adjustable resistance such that a desired resistance to the rotation of the hinge can be selected.

Clamps 287 are attached to each frame element 284, 285. As shown in FIG. 13, two clamps 287 are secured to each frame element 284, 285, although one or more than two clamps can be secured to each frame element, if desired. Each clamp 284, 285 is further secured to a pin 288. Pins 288 intrude into the patient and are inserted into the bone, as shown in FIG. 13 with phantom lines. Generally, the clamps and frame elements can be positioned to obtain a desired orientation with respect to the bone. Additional frame elements can be used to obtain a desired orientation between the frame elements secured with pins and the hinge elements.

A variety of clamp and frame element structures can be used. Suitable clamps are described further in U.S. Pat. No. 5,674,221 to Hein et al., entitled "External Fixator With Improved Clamp And Methods For Use," incorporated herein by reference, and in U.S. Pat. No. 5,891,144 to Mata et al., entitled "External Fixator," incorporated herein by reference. Generally, transducers that are connected to controller 232 are attached to an orthosis with external fixator structures in a comparable way as with orthoses having purely external frameworks.

The external fixator generally includes one or more transducers 299. Transducer 299 can be a strain sensor such that strain within the lever arms can be measured. Alternatively, transducer 299 can be a position sensor if the connector is a hinge. The position sensor measures the relative orientation of the lever arms. Additional transducers 299 can be included to measure deforming bone/tissue forces. For example, a strain sensor can be added to the pins, such that strain within the pins is measured.

Figure 14:
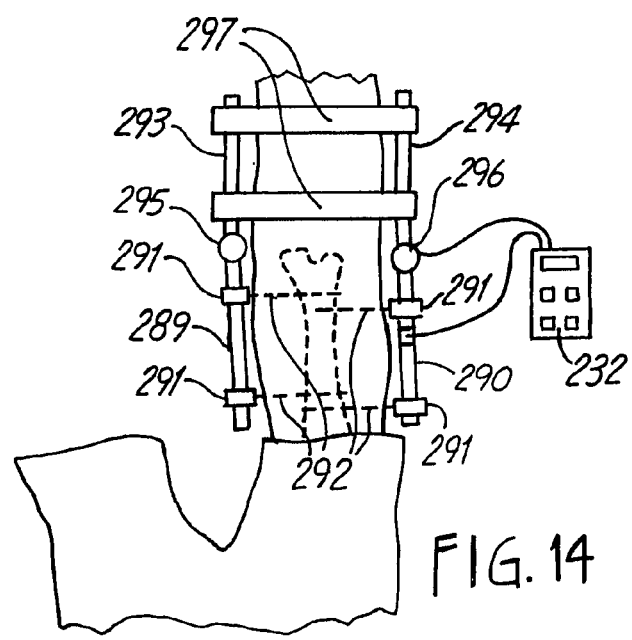
FIG. 14 is a fragmentary, top view of an alternative embodiment of an instrumented intermediary segment secured to the patient with pins using features of an external fixator.

An alternative embodiment of an instrumented orthosis with external fixator type connections is shown in FIG. 14. In this embodiment, frame elements 289, 290 are placed on either side of the body part. Clamps 291 are secured to frame elements 289, 290 and to pins 292 that pass into the patient's bone, as shown in phantom lines in FIG. 14. Frame elements 289, 290 are connected to frame elements 293, 294 with hinge elements 295, 296. Frame elements 293, 294 are secured on the patient with straps 297. Pins 292 help to prevent motion of the entire orthosis during exercise. Various features of the orthosis embodiments in FIGS. 13 and 14 can be combined as desired.

Similar structures can be used for attachment to the spine. In these systems, pins can be replaced with spinal hooks or screws. Suitable spinal attachment systems are described further in U.S. Pat. No. 5,281,222 to Allard et al., entitled "Spinal Implant System," incorporated herein by reference.

As described above with respect to FIGS. 1-5, the flexible connection can be a hinge, a set of articulating elements or the like. In preferred embodiments, the flexible connection includes a position sensor such that the relative orientation of the connection can be measured and monitored by the controller 232. U.S. Pat. No. 5,052,375, to Stark et al. entitled "Instrumented Orthopedic Restraining Device and Method of Use," incorporated herein by reference, discloses the use of a potentiometer-like mechanism used as a position sensor. Other suitable position sensors can be used. Position sensing is useful for the evaluation of range-of-motion exercises and other comparable exercises.

Furthermore, preferred flexible connections can be locked in selected orientations. If the flexible connection can be locked, isometric exercises can be performed at the locked orientation. The lock can be released and relocked at a new orientation to perform additional exercises at the new location. A couple of locking mechanisms are described in U.S. Pat. No. 5,052,375, supra. Similarly, it is useful for the flexible connection to be able to apply selected amounts of resistance to rotation. If selected amounts of resistance can be applied, the orthosis can be used more effectively for the performance of isotonic exercises. Copending U.S. patent application Ser. No. 08/442,945 to Stark, entitled "An Orthopedic Device Supporting Two or More Treatment Systems and Associated Methods," incorporated herein by reference, describes the electronic selection of a desired amount of mechanical resistance using the control unit.

While electronic control of the rotational resistance in the flexible connection has advantages, cost and design simplicity favors a purely mechanical hinge. The strain sensor readings can be accurately calibrated to reflect the forces applied to move the hinge against a setting on the mechanical resistance applicator. Thus, the controller can be used to monitor the isotonic exercises even though the resistance is not electronically controlled. In this respect, a resistance applicator 300 (FIGS. 15-29) has been designed for use with a hinge. The resistance applicator can be made integral with the hinge, but in preferred embodiments resistance unit 300 can be separated from the hinge such that no resistance is applied to the hinge when resistance is not desired. Resistance applicator 300 is designed to amplify small changes in the resistance that correlate with easily made changes in the position of a knob.

Figure 15:
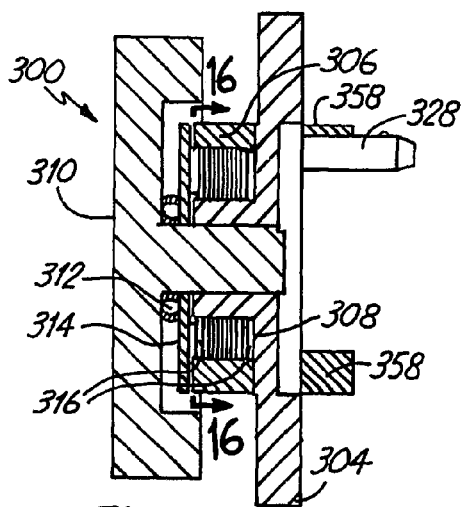
FIG. 15 is a sectional view of an embodiment of a resistance applicator taken through the middle of the resistance applicator.
Figure 16:
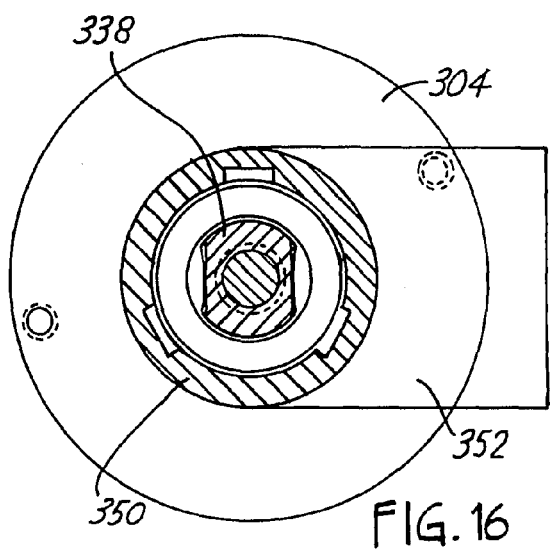
FIG. 16 is a sectional view of the resistance applicator of FIG. 15 taken along lines 16-16 of FIG. 13.
Figure 17:
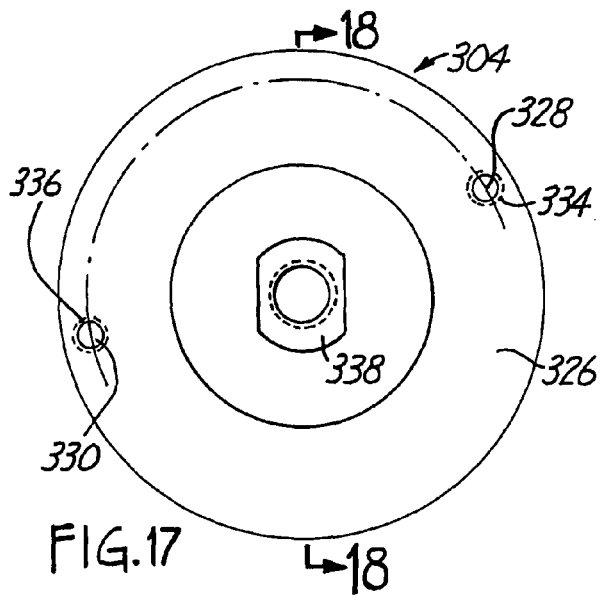
FIG. 17 is a top view of a housing of the resistance applicator of FIG. 15.
Figure 18:
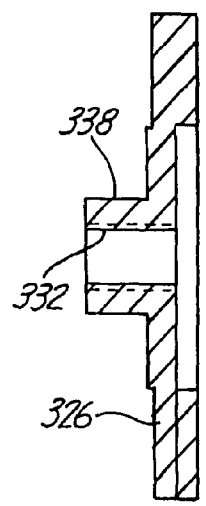
FIG. 18 is a sectional view of the housing of FIG. 17 taken along line 18-18, where the lock pin has been removed.
Figure 19:
FIG. 19 is a side view of a first lock pin of the housing of FIG. 17.
Figure 20:
FIG. 20 is a side view of a second lock pin of the housing of FIG. 17.
Figure 24B:
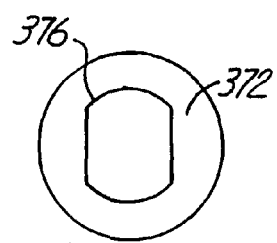
FIG. 24B is a top view of a housing ring of the resistance applicator of FIG. 15.
Figure 25:
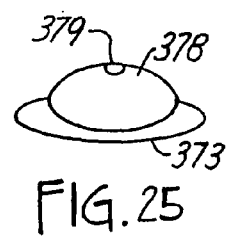
FIG. 25 is a perspective view of a compression spring of the resistance applicator of FIG. 15.

Referring to FIG. 15, a cross section through the center of an embodiment of resistance applicator 300 is shown. Similarly, FIG. 16 displays a cross section taken along lines 16-16 of FIG. 15. Resistance applicator 300 includes housing 304, a crank 306, a compression structure 308, knob 310, bearing unit 312, washer 314 and spacers 316.

Referring to 17-19, housing 304 includes base 326 and lock pins 328, 330. Lock pins 328, 330 provide releasable connection for attachment of resistance applicator 300 to a hinge. Alternative locking approaches can be used for the attachment of the friction applicator to the hinge. Base 326 includes threaded hole 332 for engaging knob 310 and threaded holes 334, 336 for engaging lock pins 328, 330, respectively. Base 326 further includes protrusion 338 for engaging compression structure 308. Lock pin 328 includes threads 340 for engaging threaded hole 334, and lock pin 330 includes threads 342 for engaging threaded hole 336. Alternatively, lock pins 328, 330 can be welded or the like to base 326.

Figure 21:
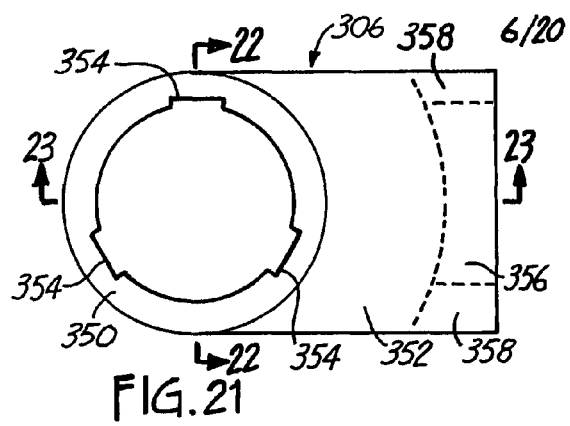
FIG. 21 is a top view of a crank of the resistance applicator of FIG. 15.
Figure 22:
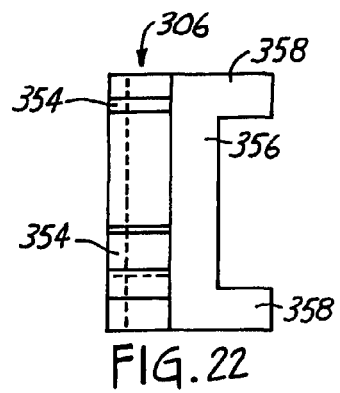
FIG. 22 is a sectional view of the crank of FIG. 21 taken along line 22-22.
Figure 23:
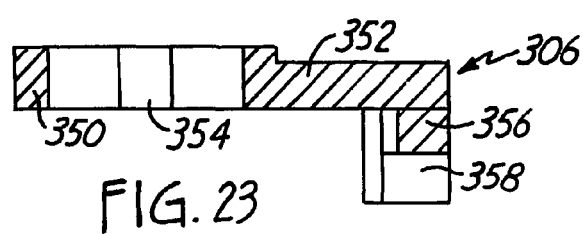
FIG. 23 is a sectional view of the crank of FIG. 21 taken along line 23-23.
Figure 24A:
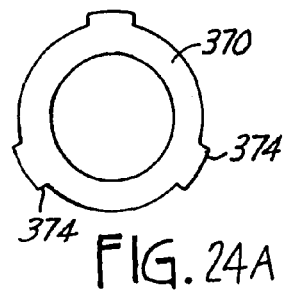
FIG. 24A is a top view of a crank ring of the resistance applicator of FIG. 15.

Referring to FIGS. 21-23, crank 306 has a central portion 350 and an arm portion 352. Center portion 350 includes notches 354 for engaging compression structure 308. Arm portion 352 includes ridge 356 and pads 358. Ridge 356 and pads 358 engage frame member 122 (FIGS. 1 and 2) or comparable frame member of an orthosis, such that rotation of the hinge of the orthosis rotates crank 306 relative to housing 304.

Compression structure 308 provides for small changes in the resistance due to changes in the distance between washer 314 and housing 304 as knob 310 is rotated, thus amplifying resistance changes by way of the knob. Compression structure 308 generally produces friction as a result of shear forces within compression structure 308 due to relative motion of housing 304 and crank 306. In the embodiment in FIGS. 15-29, compression structure 308 includes alternating crank discs 370 (FIG. 24A) and housing discs 372 (FIG. 24B) to form a multiple clutch plate. Compression structure 308 further includes a compression spring 373.

Crank discs 370 include protrusions 374 that engage notches 354 such that crank discs 370 rotate with crank 306. Housing discs 372 have a central hole 376 shaped to engage protrusion 338 in housing 304 such that housing discs 372 rotate with housing 304. Compression spring 373 includes an elastic protruding section 378 with a central hole 379. Compression spring 373 can be replaced with an spring washer or the like. In one preferred embodiment, compression structure includes 7 housing discs 372 and 6 crank discs 370 in an alternating layers. Other quantities of crank discs 370 and housing discs 372 can be used as desired.

Figure 26:
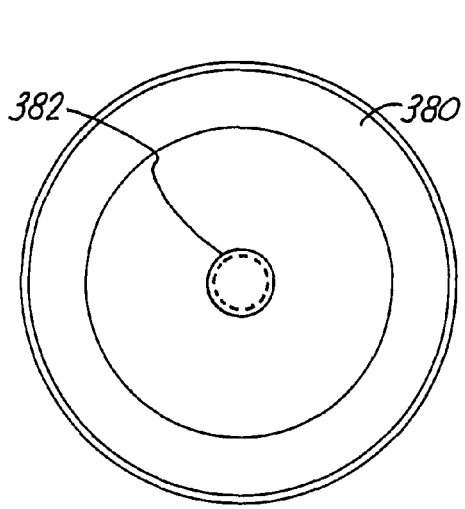
FIG. 26 is a bottom view of a knob of the resistance applicator of FIG. 15.
Figure 27:
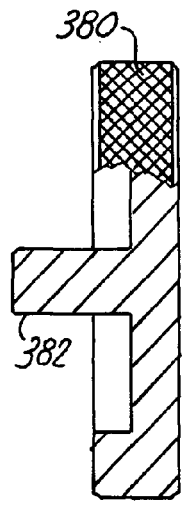
FIG. 27 is a fragmentary, side view of the knob of FIG. 26, where a portion of the grip of the knob has been removed.
Figure 28:
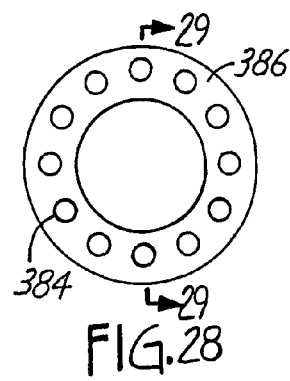
FIG. 28 is a top view of a bearing unit of the resistance applicator of FIG. 15.
Figure 29:
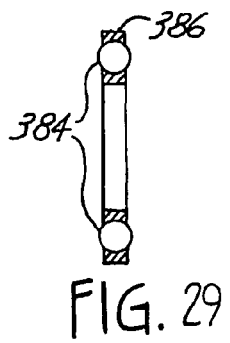
FIG. 29 is a sectional view of the bearing unit of FIG. 28 taken along line 29-29 of FIG. 28.

Referring to FIGS. 26-27, knob 310 includes a grip handle 380 and a threaded shaft 382 with threads and diameter suitable for engaging the threads of threaded hole 332 in housing 304. Referring to FIGS. 28-29, bearing unit 312 includes a ring of ball bearings 384 in a bearing case 386. Bearing unit 312 can be replaced with other bearing structures or other friction reducing approaches such as hydro bearings.

Washer 314 has a suitable inner diameter such that threaded shaft 382 can pass through the inner diameter but bearing unit 312 cannot pass. Washer 314 has an outer diameter such that washer 314 rests on center portion 350 of crank 306 covering the opening to compression unit 308 between housing 304 and crank 306. Two optional spacers 316 preferably are located with one on each side of compression unit 308. Spacers 316 have the shape of a washer but with a suitably larger inner diameter and smaller outer diameter than washer 314 such that spacers 316 fit within the cavity between crank 306 and housing 304 holding compression structures 308.

The primary components of the resistance applicator 300 preferably are made from metals and/or alloys. Aluminum alloys and stainless steel are suitable metals for the construction of housing and crank components. Rigid polymers can be used in place of metals for the housing and crank elements. The spacers preferably are made of brass. The housing disc preferably is made from spring steel, and the crank disc preferably is made from spring tempered phosphor bronze. The bearing case can be made from Nylon®.

Resistance applicator 300 is designed to attach to a hinge such that housing 304 moves with a frame member attached to one side of the hinge while crank 306 moves with a frame member attached to the other side of the hinge. Thus, rotation of the hinge results in rotation of housing 304 relative to crank 306. Tightening of knob 310 presses washer 314 down onto compression unit 308. Housing rings 372 and crank rings 370 rotate relative to each other when housing 304 moves relative to crank 306. Increasing the pressure on compression unit 308 results in increased resistance in the rotation of housing 304 relative to crank 306 because of friction between housing rings 372 and crank rings 370. Increasing the number of housing rings 372 and/or crank rings 370 increases the amount of resistance. This design provides for sensitive adjustment of rotational resistance provided by resistance applicator 300 by rotation of knob 310. Housing rings 372 and crank rings 370 can have non-uniform thickness or non-uniform shape such that the degree of resistance varies as a function of rotational angle.

A particular embodiment of a left hinge 400 for use with resistance applicator 300 is shown in FIGS. 30-32. This hinge has a construction that provides for particularly easy release of the lock by a patient with one hand. The orientation of the hinge is measured by a position sensor to assist the patient in resetting the lock at a desired orientation. A right hinge would be the mirror image of the hinge in FIGS. 30-32.

Hinge 400 includes a outer plate 402, washer 404, locking unit 406, ring lever 408, electrical resistance disc 410 and inner plate 412. Outer plate 402 is connected to a frame member 418. Strain sensor 230 can be attached to frame member 418. Outer plate 402 and inner plate 412 include concentric stop holes 420, bolt holes 422, connection holes 424 and slot 426. The corresponding holes are aligned between left outer plate 402 and inner plate 412.

One or two stop pins 430 (FIG. 33) can be placed through two aligned stop holes 420 in outer plate 402 and inner plate 412 to define limits or end stops of hinge rotation. Barrel bolts 432 (FIG. 34) including a male member 434 and a female member 436 or other fastener are secured through bolt holes 422 to hold hinge 400 together. Lock pins 328, 330 of resistance applicator 300 can be secured through connection holes 424 to releasably secure resistance applicator 300 in an operable position with respect to hinge 400. Electrical resistance disc 410 rests within a hollow 438 within inner plate 412. Electrical resistance disc 410 makes electrical contact with wire 440.

Locking unit 406 includes control disc 446, slider 448, slider spring 450 and lock-out latch 452. Control disc 446 included a slit 454 in which slider 448 slides. Slider 448 has a groove 456 and an indentation 458 with a catch 460. Lock-out latch 452 has a knob 462 and a bar 464. Bar 464 slides within slots 426 and can fit within groove 456 to hold slider 448 in a depressed, unlocked, position.

Ring lever 408 is connected with a frame member 470. Ring lever 408 has an opening 472 with a diameter slightly larger than the diameter of control disc 446 such that control disc 446 can fit within opening 472. Control disc 446 preferably has a thickness slightly larger than ring lever 408. A set of concentric, notches 474 are located around the edge of opening 472 of ring lever 408. Catch 460 of slider 448 fits within the notches 474 to lock the hinge at a particular orientation when slider 448 is in an extended position. Depressing slider 448 against the force of spring 450 disengages catch 460 from one of the notches 474 such that hinge 400 is free to rotate within the bounds establishes by any stop pins 430. Ring lever 408 includes an electrical contact 476 set within a hole 478 that contacts electrical resistance disc 410. Electrical contact 476 is connected by wire 480 to controller 232 or alternative resistance meter. Washer 404 can be placed between outer plate 402 and control disc 446.

Outer plate 402, inner plate 412, ring lever 408, control ring 446, lock-out latch 452 and slider 448 preferably are made from rigid, durable materials. In particular, outer plate 402 and inner plate 412 are preferably made from an aluminum alloy, and ring lever 408, control ring 446, lock-out slide 452 and slider 448 preferably are made from stainless steel. Spring 450 generally would be made from resilient steel or the like. Washer 404 and stop pin 430 generally are made from polytetrafluoroethylene or the like. Electrical resistance disc 410 can be made from circuit board material with a resistance element screen-printed on its surface.

Frame members 418 and 470 extend to opposite sides of the hinge such that movement of frame member 418 relative to frame member 470 involves rotation of hinge 400. When hinge 400 rotates, outer ring 402 and inner ring 412 rotate relative to ring lever 408. Outer ring 402, inner ring 412 and control disc 446 are held fixed with respect to each other by way of bolts passing through bolt holes 422. The orientation of hinge 400 is locked unless slider 448 is depressed such that catch 460 is withdrawn from notches 472. Lock-out slide 452 can hold slider 448 in the depressed, unlocked position. The position of ring lever 408 relative to inner ring 412 can be measured by way of the position of electrical contact 476 along electrical resistance disc 410. The relative position of electrical contact 476 along electrical resistance disc 410 provides a variable electrical resistance useful for position/orientation sensing.

Figure 35:
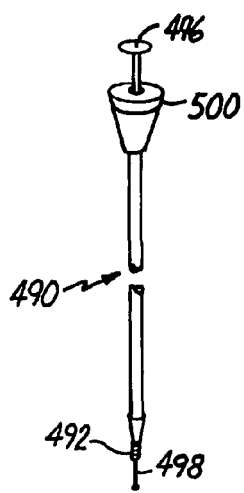
FIG. 35 is a fragmentary perspective view of a manual, hinge lock release.
Figure 36:
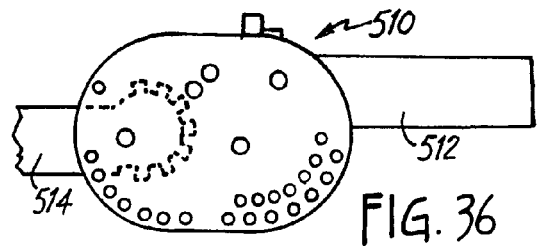
FIG. 36 is a side view of a dual axis hinge suitable for use with resistance applicator of FIG. 15.
Figure 37:
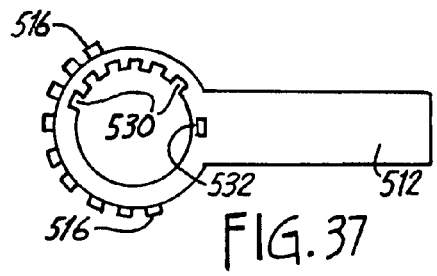
FIG. 37 is a side view of a proximal arm of the dual axis hinge of FIG. 36.
Figure 38:
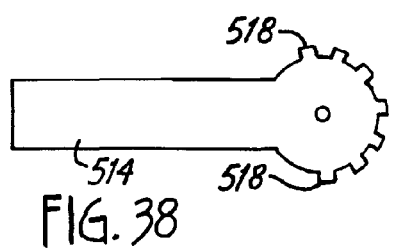
FIG. 38 is a side view of a distal arm of the dual axis hinge of FIG. 36.
Figure 39:
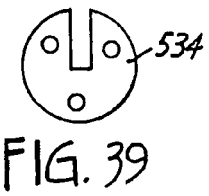
FIG. 39 is a side view of a control ring of the dual axis hinge of FIG. 36.
Figure 40:
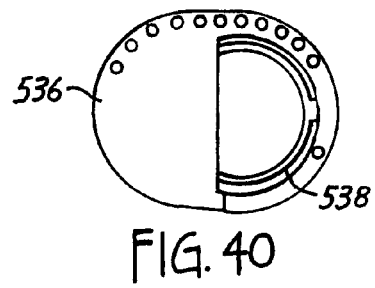
FIG. 40 is a side view of an inner plate of the dual axis hinge of FIG. 36.
Figure 41:
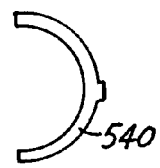
FIG. 41 is a side view of a resistance ring of the dual axis hinge of FIG. 36.

It may be convenient to provide for release of a hinge with a remote control. U.S. Pat. No. 5,052,375 provides for the release of the hinge using a command from the control unit. It may be desirable to have a simple mechanical remote release. A simple photographic shutter release 490 (FIG. 35) can be adapted for this purpose. Shutter release 490 can be screwed at threaded tip 492 into hinge 400 at threaded hole 494 in control ring 446 (FIG. 32). Pressing plunger 496 advances cable 498. When shutter release 490 is screwed into hinge 400 advancing cable 498 depresses slider 448 thereby unlocking hinge 400. Rotating knob 500 causes plunger 496 to spring back to its extended position withdrawing cable 498 and locking hinge 400 as slider 448 extends such that catch 460 engages a notch 472. Alternative designs for mounting of a manual hinge release involve pulling a plunger that in turn pulls slider 448 such that the lock is disengaged and such that releasing the plunger reestablishes the hinge lock.

Certain joints such as the knee are cams that do not involve rotation about a single axis. A biaxial hinge can be used to more closely approximate the motion of the joint cam. A biaxial hinge 510 generalizing on the structure of hinge 400 is shown in FIGS. 36-41. Biaxial hinge 510 includes a proximal arm 512 and a distal arm 514. Proximal arm 512 includes teeth 516 which engage teeth 518 on distal arm 514. Proximal arm 512 further includes lock notches 530 and an electrical contact 532 for position (orientation) sensing. Control ring 534 operates similarly to control ring 446 in hinge 400 to control the locking/unlocking of the hinge. Inner plate 536 includes an indentation 538 for securing electrical resistance disc 540. Electrical resistance disc 540 provides for variable electrical resistance according to the orientation of the hinge due to the relative position of the electrical contact 532 with respect to electrical resistance disc 540.

In simplified embodiments, controller 232 may just include analog circuits and a suitable display. In preferred embodiments, controller 232 includes a digital processor to provide a more sophisticated interface with the patient and to preform more involved monitoring functions. The digital processor preferably is a microprocessor. The digital processor can be programmed in any of a variety of computer languages including, for example, basic, assembler, C, C++ and the like. Preferably, controller 232 is portable, which in this context means that the controller is small enough to be held in the hand of a patient. More preferably, controller 232 is small enough to be placed in a standard shirt pocket.

A preferred microprocessor based controller 232 has several subsystems including a power supply such as a nine volt battery, a transducer bias circuit such as described below, A/D converters, a microprocessor, real time clock, RAM and non-volatile storage such as FLASH or EEPROM, a graphic display such as a 64×128 pixel LCD display with a corresponding driver, keypad, audible or tactile feedback device, data link to transducer, and RS232 standard output for serial connection or modem access.

In one particular embodiment, the microprocessor is a Motorola MC68HC11AlFN 8-bit microcontroller with built-in deep sleep shutdown mode for power conservation between active events, a programmable serial interface and an 8-channel, 8-bit A/D converter. In this embodiment, controller 232 can provide analog multiplexing and A/D conversion for up to 8 analog input signals over a voltage range from 0.0 to +5.0 volts. For example, three of the channels can be devoted to provide signal conditioning for up to three strain sensors, and three of the channels can be devoted to providing signal conditioning for up to three position (angle) sensors. The remaining two input channels then can be used for additional treatment devices.

The controller module memory is partitioned into FLASH, SRAM and EEPROM. Each section is independently addressable. In one particular embodiment, FLASH is 128 K words, and EEPROM is 32 K words with 8-bits (I byte) per word. A 16 K portion of SRAM is used for memory management. The EEPROM supports in-circuit reprogramming by way of the microcontroller serial channel for code updates. The SRAM has battery backup, and FLASH provides non-volatile storage of recorded data during times when the microprocessor is not powered. The real time clock also is battery powered to allow time keeping to continue when the microcontroller circuitry is off. The real time clock is capable of generating periodic interrupts at a programmable rate to power switching circuitry to activate the microcontroller during an alert mode of operation.

The RS-232 interface consists of three conductor (TxD, RxD and GND) jack type connector with a mechanical switch to automatically switch power on to all on-board electronics when the plug is inserted. The baud rate of the interface is programmable with standard rates such as 9600 and 19200. A suitable display is a Hantronix HGS13Y or Densitron™ LE3328 LCD with Hitachi HD61202 and HD61203 LCD controller chip sets. The display can be run with a five volt supply that can be separate or not from the power supply for the rest of controller 232. In this embodiment, a four key keypad is interfaced with the microcontroller.

Figure 42:
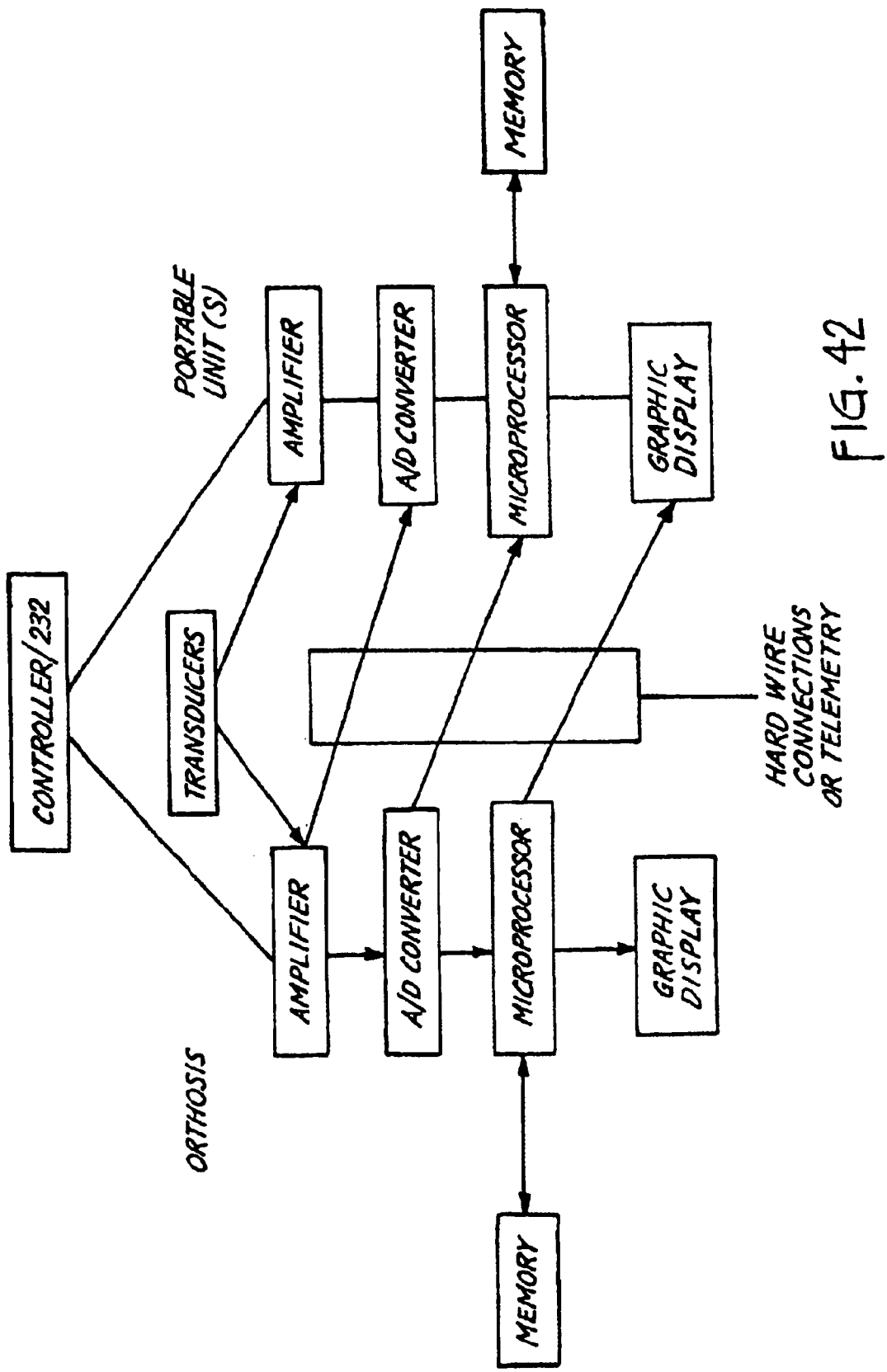
FIG. 42 is a schematic illustration of possible division of components of the controller between placement on the orthosis and placement in a separate portable unit.

All of the components of controller 232 can be placed on the orthosis or in a separate case. The components of controller 232 can be integrated into a single package or physically partitioned into portions mounted on the orthosis frame and/or portions placed into one or more small cases. This is shown schematically in FIG. 42, where connections between the Orthosis side to the portable unit(s) side indicates that a connection can be made by a hard wire connection or telemetry. Generally, the components are not duplicated such that various combinations can be made following a selected path through the chart. In one preferred embodiment, controller 232 is mounted in a single case that is releasably attached to the orthosis frame so that the case can be carried on the frame and removed when desired to read the display more easily. In an alternative preferred embodiment, the display and corresponding drivers can be mounted in one case that can be moved for easier viewing while the remaining components are attached to the frame of the orthosis. The display can be interfaced with the remaining portions of the controller with a wire, by radio communication or by infrared communication. A video card with an RF modulator to converting broad band video into analog NTSC signals in controller 232 can be attached to a television set rather than to a graphic display. Use of a television provides better viewing as well as conserves battery power since the display alternatively would be consuming significant amounts of battery power. An alternative output for persons who are vision-impaired is to provide audible feedback, either in the form of recognizable sounds that change when a target is reached, through variations in pitch or volume, or by a voice synthesizer that speaks to the patient such as "Push Harder," "Good," or "Now rest for a moment."

Controller 232 preferably stores a software program that manages the use of the device for patient rehabilitation. The software can provide for alerting the patient to scheduled times for the performance of exercises using audible and/or vibratory signals. Controller 232 preferably provides instructions on the exercises as well as feedback and reinforcement messages to the patient. Further details on the operation of the controller are provided below.

Stored information relating to the patient's performance of exercises generally is downloaded to the supervising health care professional at specified intervals. The download of the information can be performed in a variety of ways. If the patient goes to the office of the health care professional, controller 232 can be directly connected to the monitor station/computer using the RS232 port or other port using suitable protocols including standard protocols. Alternatively, controller 232 can be attached to a modem by way of the RS232 port or other suitable port. Since with certain embodiments the file sizes are relatively small, a single chip, 9 volt supply Rockwell® 2400 baud modem can be used. Controller 232 can be in radio communication with a monitor station. Controller 232 then would include a radio transmitter and, optionally, a receiver. Radio communication with a monitor station is described further in copending U.S. Patent Applications to Stark et al., Ser. No. 08/389,680, now U.S. Pat. No. 5,929,782 entitled "Communication System For an Instrumented Orthopedic Restraining Device and Methods Therefore" and Ser. No. 08/804,950, now U.S. Pat. No. 5,823,975 entitled "Local Monitoring System For an Instrumented Orthopedic Restraining Device and Methods Therefore," both of which are incorporated herein by reference. The display or television set similarly can be in communication with controller 232 by way of radio transmissions or infrared communication such that a wire attachment is not necessary.

In order for the value of electrical resistance associated with a strain sensor to be useable as a measure of applied stress during isometric exercises, the values must be referenced to a "null" valve approximately corresponding to a value when no strain is applied to the orthosis. The null value can be set by a manual adjustment performed by the health care professional or by the patient. The "null" value, however, is preferably established automatically without the need for calibration by the user. Furthermore, the variations in the resistance due the strain sensor preferably are converted into a voltage value that is amplified to make efficient use of an analog-to-digital (A/D) converter with a specified number of binary digits.

Figure 43:
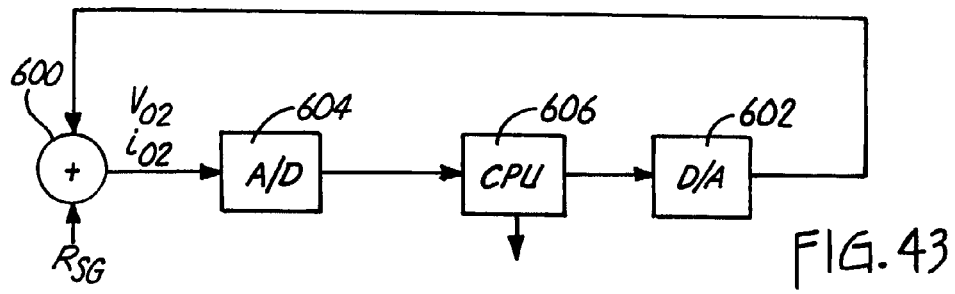
FIG. 43 is a schematic diagram indicating components used in the amplification and balancing of the strain measurement.

An approach for performing this calibration is outlined schematically in the block diagram of FIG. 43. A summing amplifier 600 amplifies a signal based on the resistance of the strain sensor relative to an input signal from a digital-to-analog (D/A) converter 602. The signal from summing amplifier 600 goes to an A/D converter 604. The signal from A/D converter 604 goes to processor (CPU) 606. Processor 606 evaluates whether the signal from the A/D converter is within a desired range and adjusts the signal to D/A converter, if appropriate to bring the signal from the A/D converter to be within a specified range. An National Semiconductor® 8 bit, 8 channel D/A chip can be used. Processor 606 further uses the signal for monitoring the exercise routine and displaying the results, or sends the signal to a different processor to perform these functions.

Figure 44:
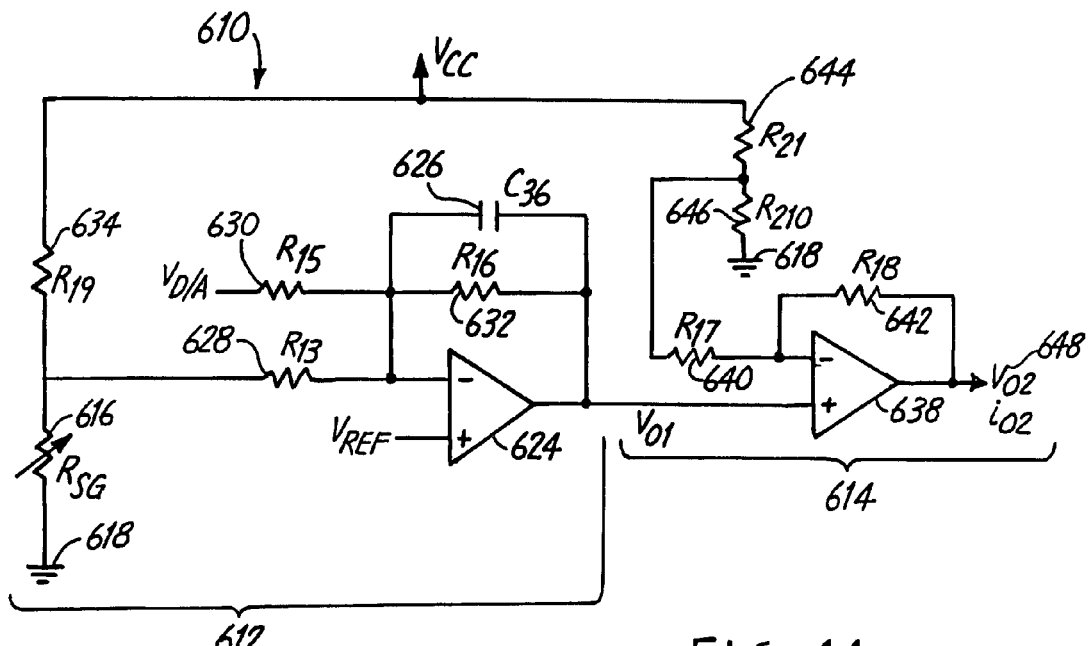
FIG. 44 is a circuit diagram of one embodiment of a summing amplifier useful as a component in the diagram of FIG. 43.

An embodiment of summing amplifier 610 is shown in FIG. 44. Amplifier 610 is a two stage amplifier including a first amplifier circuit 612 and a second amplifier circuit 614. First amplifier circuit 612 includes strain sensor resistance $R_{SG}$ 616 connected to ground 618, a reference voltage $V_{REF}$, source voltage $V_{CC}$ and D/A reference voltage $V_{D/A}$. First amplifier circuit 612 further includes amplifier 624, capacitor $C_{36}$ 626 and resistors $R_{13}$ 628, $R_{15}$ 630, $R_{16}$ 632 and $R_{19}$ 634. First amplifier circuit 612 outputs a voltage $V_{01}$ to second amplifier circuit 614.

Second amplifier circuit 614 includes amplifier 638 and resisters $R_{17}$ 640, $R_{18}$ 642, $R_{21}$ 644 and $R_{210}$ 646. Resister $R_{210}$ is further connected to ground. Second amplifier circuit 614 outputs voltage $V_{02}$ and current $i_{02}$ to A/D converter 604.

The output voltage for summing amplifier 610 can be calculated to be:

$$V_{02} = X_1 V_{Ref} - X_2 V_{CC} - X_3 V_{D/A}, \text{ where}$$

$$X_1 = \left[\left(\frac{R_{17} + R_{18}}{R_{17}}\right) - \right.$$

-continued $$\frac{R_{18}R_{21}R_{210}}{(R_{17})^2(R_{21}+R_{210})+R_{17}R_{21}R_{210}}\Bigr]\times\Bigl[\frac{R_{13}(R_{15}+R_{16})+R_{15}R_{16}}{R_{13}R_{15}}-$$

$$\frac{R_{16}}{R_{13}}\frac{R_{19}R_{strain}}{R_{strain}(R_{13}+R_{14})R_{13}R_{14}}\Bigr]$$

$$X_2 = \Bigl(\Bigl(\frac{R_{17}+R_{18}}{R_{17}}\Bigr)-\Bigl(\frac{R_{18}R_{21}R_{210}}{(R_{12})^2(R_{21}+R_{210})+R_{17}R_{21}R_{210}}\Bigr)\Bigr)\times$$

$$\Bigl(\frac{R_{16}R_{strain}}{R_{strain}(R_{13}+R_{19})+R_{13}R_{19}}+\frac{R_{18}R_{210}}{R_{17}(R_{21}+R_{210})+R_{21}R_{210}}\Bigr)$$

$$X_3 = \Bigl(\frac{R_{16}}{R_{15}}\Bigr)\Bigl(\Bigl(\frac{R_{17}+R_{18}}{R_{17}}\Bigr)-\Bigl(\frac{R_{18}R_{21}R_{210}}{(R_{12})^2(R_{21}+R_{210})+R_{17}R_{210}R_{21}}\Bigr)\Bigr)$$

For use with a general purpose, 350 ohm strain gauge/sensor, suitable accuracy is obtained using resistors with a 1% tolerance except as indicated below. Suitable strain gauges/sensors are available from Vishay Micromeasurements Group (Raleigh, N.C.) (e.g., type 125AD, part number EK-XX-125AD-350 with dual copper pads), or JP Technologies (San Bernardino, Calif.). The input voltage $V_{CC}$ can be set to 5.0V±0.1% and $V_{Ref}$ can be set to 2.5V±0.1%. Then, one suitable set of values for the resistors and capacitors are $R_{13}$=1 KΩ, $R_{15}$=150 KΩ, $R_{16}$=100 KΩ, $R_{17}$=1.5 KΩ, $R_{18}$=32 KΩ, $R_{19}$=350 KΩ±0.1%, $R_{21}$=2.5 KΩ, $R_{210}$=2.5 KΩ, $R_{SG}$=350Ω±0.3% and $C_{36}$=0.01 μF. With these values of components the change in strain gauge resistance to move the output voltage from about 0V to about 5V is in the range from 1.2515Ω to 1.3568Ω. The summing amplifier overall provides a nominal gain of about 2300 with an accuracy of about +/−0.125 ft-lbs.

Figure 45:
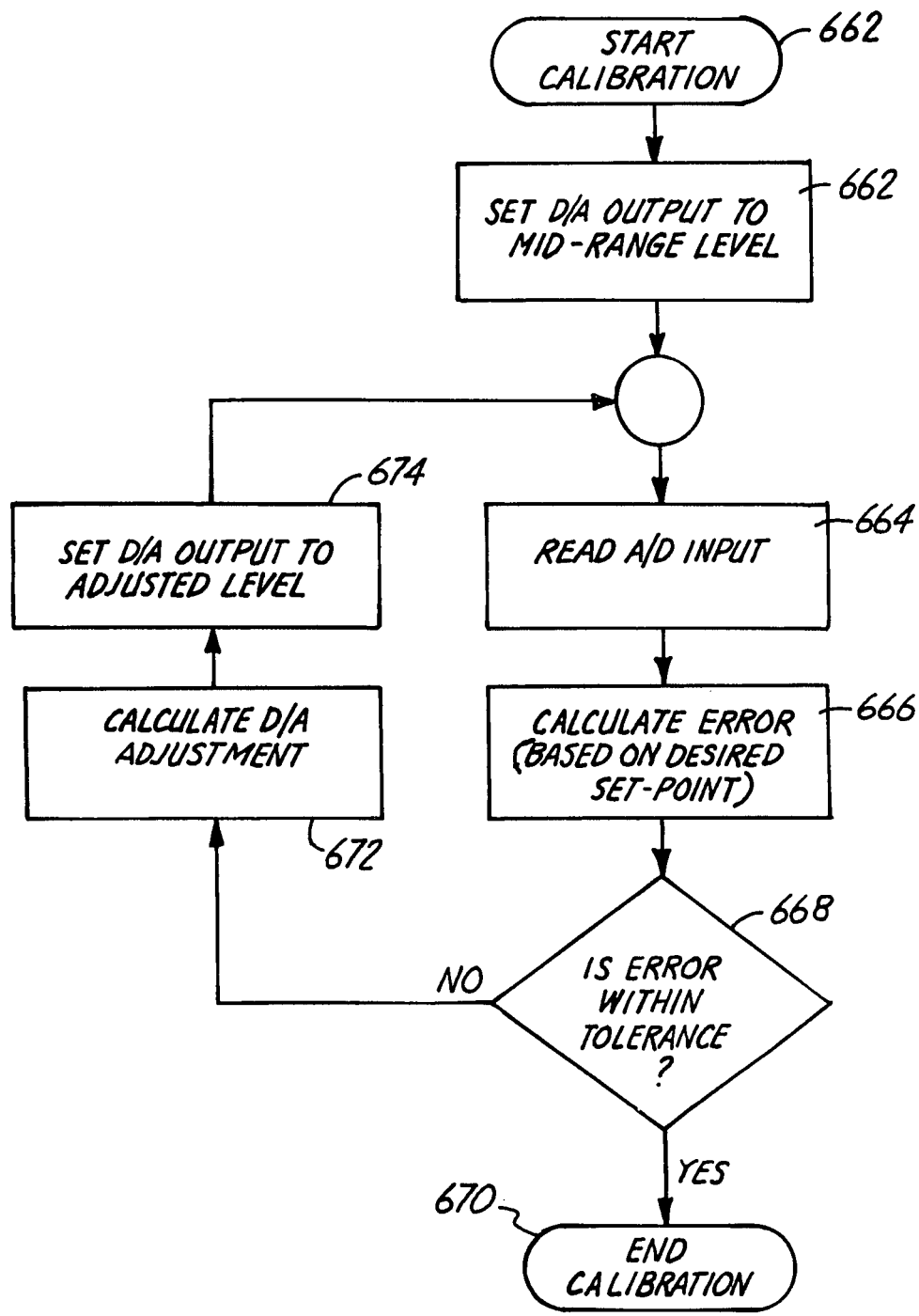
FIG. 45 is a flow diagram outlining the process for calibrating the strain measurements.

A flow chart 660 outlining the performance of the calibration is shown in FIG. 45. The calibration is initiated 662 by setting the D/A output to the summing amplifier 600 to a midrange value assuming that no stress is being applied to the orthosis by the patient. Then, the A/D input is read 664 by the CPU 606. The error in the digitized strain measurement is calculated 666 based on a desired set-point given the parameters of the summing amplifier 600 and the properties of the A/D converter 604. The error is compared 668 with acceptable tolerance values. If the error is within tolerance values, the calibration is terminated 670. If the error is outside of tolerance values, a new value of output from the D/A converter is calculated 672 to bring the error of the output from the A/D converter to within tolerance values. The value of the output from the D/A converter is set 674 to the adjusted value. Then, the input from the A/D converter is read 664 again and steps 664-668 are repeated until the error is within tolerance values.

Additional treatment units can be combined with the exercise orthosis to assist with the rehabilitation of a joint. For example, the controller 232 can coordinate isometric and/or isotonic exercise treatments along with energy propagating transducer treatments. Exercise/transducer combined treatment approaches are described generally in copending U.S. patent application Ser. No. 08/442,945 to Stark, entitled "An Orthopedic Device Supporting Two or More Treatment Systems and Associated Methods," incorporated herein by reference. Energy propagating transducer based treatments include, for example, ultrasonic treatments, pulsed electromagnetic treatments and electrical conductance treatments.

In addition, a treatment device for alleviating pain due to osteoarthritis can be monitored by controller 232 or comparable control unit. The osteoarthritis treatment device could be effectively used alone or combined with an exercise orthosis. Joins often wear unevenly. This results in pain due to bone on bone contact where cartilage has worn away. A support can be placed around the joint to shift the stresses to the less worn portions of the joint thus alleviating pain.

Figure 46:
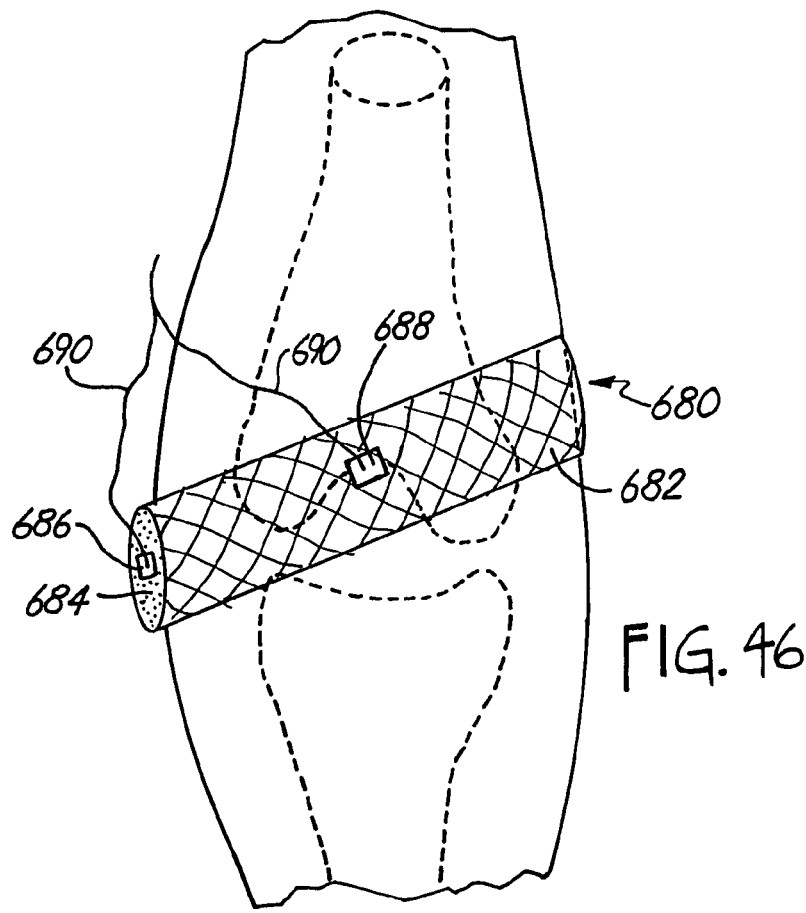
FIG. 46 is a front, perspective view of a condyle sensor placed around the knee of a patient.

Referring to FIG. 46, an appropriate osteoarthritis support 680 for a knee is shown. Osteoarthritis support 680 includes a restraint 682 and a force applicator 684. Knees often wear excessively on the medial (inner) side of the knee. Applying force on the lateral (outer) side of the knee shift stress from the medial to the lateral side of the knee. Occasionally knees wear excessively on the lateral side, in which case the support can be adjusted accordingly. Force applicator 684 can be a pad, a bladder or similar device. Force applicator 684 should distribute the force over a reasonable area so that the skin is not damaged and no significant circulatory or neural functions are interrupted. Restraint 682 can be any suitable strap or the like such that the forces are balanced in a suitable location displaced from the joint.

The amount of a force applied to the joint preferably is measured to avoid the application of excessive force and to monitor compliance. The applied lateral forces can be measured using a pressure sensor or strain sensor 686 in or on force applicator 684 and/or using a strain sensor 688 on restraint 682. Pressure sensors/strain sensors 686, 688 can be connected to the controller 232 by way of wires 690.

Suitable strain sensors were described above. Pressure sensor 686 can be any reasonable type. A variety of suitable pressure sensors are commercially available. Preferred pressure sensors include the MPX series of pressure sensors manufactured by Motorola because of their linear output and small size. Other suitable pressure sensors use silver oxide ink surfaces separated by a dielectric material or piezoelectric materials that produce a voltage when stressed. Suitable pressure sensors include strain sensors attached to the surface of a bladder since the surface strain is a function of the pressure in the bladder.

Osteoarthritis support 680 to alleviate osteoarthritis can be beneficially used with an exercise orthosis. The performance of isometric or isotonic exercises stimulates the secretion of natural lubricating fluids within the joint. Thus, the support can alleviate the pain sufficiently to perform the exercises, which lead to further pain alleviation due to the secretion of lubricating fluids. The combination of the exercise orthosis and osteoarthritis support 680 can provide considerable improvement in the condition of the patient. Osteoarthritis support 680 can be easily redesigned for other joints or to alleviate pain associated with unusual wearing of a particular joint.

Figure 47:
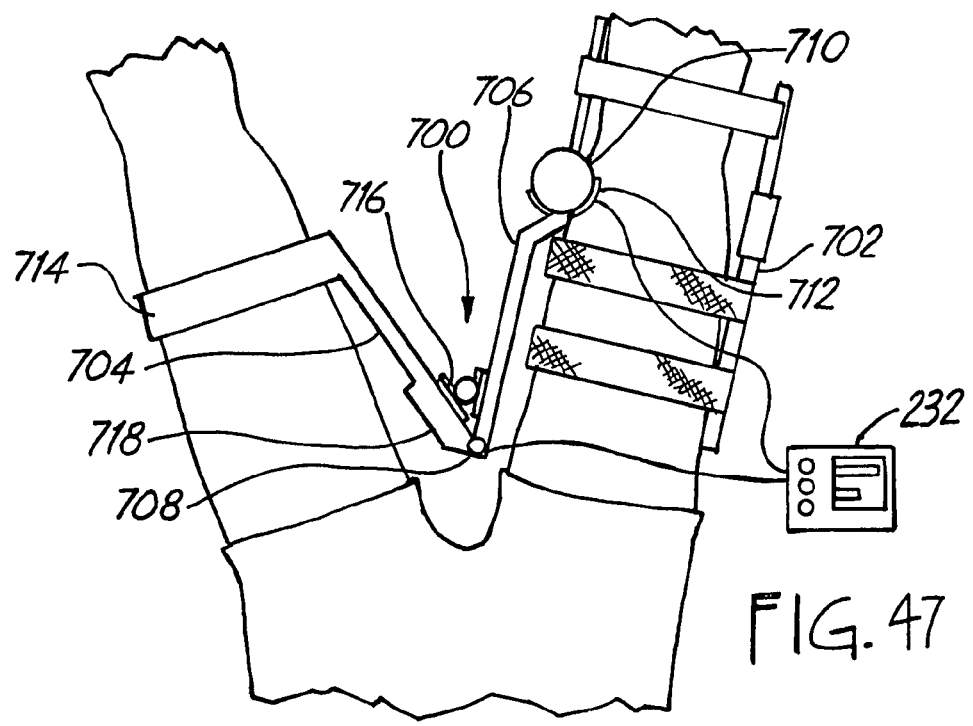
FIG. 47 is a front view of an instrumented abduction/adduction exerciser.

Other instrumented exercise units can be used in conjunction with the orthosis/brace using a single controller 232 or multiple controllers, or alone as an alternative to the orthosis/brace. One such alternative exercise unit is an abduction/adduction exercise device. A first embodiment of an instrumented abduction/adduction exerciser 700 is shown in FIG. 47. Exerciser 700 is used in conjunction with an orthosis 702.

Abduction/adduction exerciser 700 includes two lever arms 704, 706. Lever arms 704, 706 are joined at hinge 708. Lever arm 706 of exerciser 700 releasably attaches to hinge 710 of orthosis 702 with connector 712. Lever arm 704 is attached to a padded cuff 714 that can be secured around the patient's leg with a hook-and-loop fastener or the like.

Generally, hinge 708 can be released and locked at a selected orientation. Hinge 708 is locked at an orientation for the performance of isometric exercises. Alternatively, hinge 708 freely rotates, and lever arms 704, 706 are held at a nominal position by spring 716 and can be moved toward each other with the application of force. The amount of force needed to move lever arms 704, 706 can be varied by suitable selection of spring 716.

Instrumented abduction/adduction exerciser 700 includes a strain sensor 718 or the like to measure stresses within exerciser 700. Strain sensor 718 is connected to controller 232 or to a separate control unit. Thus, when the patient flexes or stresses and releases exerciser 700, as part of an exercise routine, the compressive forces applied by the patient can be measured, prompted and monitored similarly to forces applies to an orthosis.

In this particular embodiment, abduction/adduction exerciser 700 is designed to be flexed by a patient's legs. Straightforward modifications can be used to design a comparable exerciser for use with other flexible body parts, such as an exerciser flexed by movement of a patient's arm relative to their body trunk.

Figure 48:
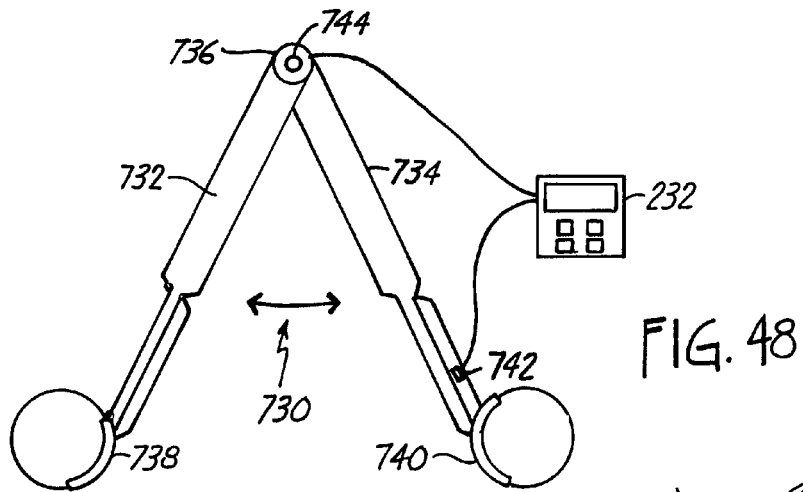
FIG. 48 is a front view of an alternative embodiment of an instrumented abduction/adduction exerciser.

Referring to FIG. 48, an alternative embodiment of an abduction/adduction exerciser 730 includes lever arms 732, 734. Lever arms 732, 734 are connected at variable resistance hinge 736. Variable resistance can be applied, for example, with the mechanical resistance applicator described above with respect to FIGS. 15-29. Alternatively, electronically controlled variable resistance hinges described above can be used. Lever arms 732, 734 are attached to cuffs 738, 740 that are designed to engage the patients leg or other suitable body part.

Abduction/adduction exerciser 730 includes suitable transducers, such as a strain sensor 742 and/or a position sensor 744 connected to hinge 736. Transducers 742, 744 are connected to controller 232 or to another suitable control unit/display. Measurements from the transducers can be used to monitor, prompt and evaluate the exercises by the patient.

Another alternative instrumented exercise device is an instrumented therapeutic cord, i.e., bands or tubes. The uninstrumented versions of these devices are sold under the tradenames of Thera-Band®, MediCordz® and Stretch-Cordz®. Instrumented therapeutic cords provide a versatile, low cost exercise alternative, which can be used alone or in combination with an instrumented orthosis, as described herein. The unifying theme of these devices is the presence of an elastic cord that provides resistance against motion by the patient.

Figure 50A:
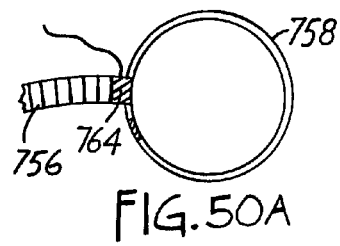
FIG. 50A is a fragmentary, top view of a cuff used with an instrumented therapeutic cord.
Figure 49:
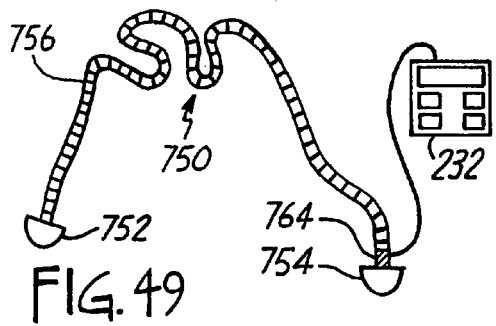
FIG. 49 is a top view of an instrumented therapeutic cord.
Figure 50B:
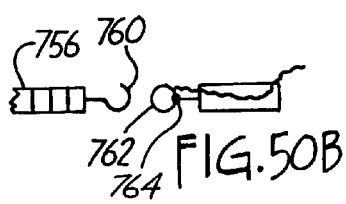
FIG. 50B is a fragmentary, top view of a therapeutic cord with an instrumented attachment.

A embodiment of an instrumented therapeutic cord 750 is depicted in FIG. 49. Therapeutic cord 750 includes two handles/clamps 752, 754 connected to elastic cord 756. One or more the handles/clamps can be replaced with a cuff 758, as shown in FIG. 50A. Cuff 758 can be designed to fit around a patient's waist or limb, or a table leg or other rigid object for the performance of certain exercises. Referring to FIG. 50B, one or more handles/clamps can be replaced with a fastener 760 such as a hook that connects to a fixed handle 762. A variety of approaches can be used to fasten the instrumented therapeutic cord to a fixed object for the performance of exercises. Additional handles/clamps or cuffs can be used, as desired, for the performance of specific exercises.

Cord 756 is connected to a transducer 764 directly or indirectly by way of a handle or the like. As shown in FIGS. 49 and 50A, the transducer 764 is attached between cord 764 and handle 754 or cuff 758, although transducer 764 can be attached to other portions of cord 764. If transducer 764 is attached indirectly, the transducer should be attached to a handle or the like that experiences strain when forces are applied to cord 756, such that in either embodiment, the forces measured by the transducer are functions of the forces applied to the cord. Transducer 764 can be a strain sensor or stretch sensor. Suitable stretch sensors are commercially available based on piezoelectric transducers, molecular [?], grid resistance transducers or the like. The transducer can be attached to a suitable substrate for mounting. Transducer 760 can be connected to controller 232 or other suitable control unit.

To perform exercises with an instrumented therapeutic cord, one of the handles/clamps 752, 754 can be attached to an immovable object such as a door knob of a closed door. The patient then stretches the cord, using the other handle/clamp 752, 754, a cuff 758 or the like, with a hand, foot, limb or other body part to exercise the corresponding muscles. Alternatively, the patient stretches cord 756 while contacting the therapeutic cord 750 at two or more points, such as two handles/clamps 752, 754. A large variety of exercises can be performed by appropriately selecting the arrangement of the therapeutic cord.

To adjust the exertion required in the exercises with the therapeutic cord, therapeutic cords are commercially available with different amounts of resistance. If desired, the different levels of resistance can be color coded by the color of the cord, the handle or a portion of the cord. Each cord with different levels of resistance need to be calibrated such that the transducer reading can be correlated with the exerted forces. Controller 232 can be programmed with separate look-up tables for each level of resistance. If the resistance level of the cord is input into the controller, the controller can make the suitable correlation.

For the performance of closed chain exercises, a body portion pushes against an essentially immovable surface. The surface can be a floor, a wall, a table top or the like. In order to monitor the forces being applied, a sensor is used that is placed between the body part and the surface. For example, in FIG. 1 orthosis 100 includes a foot support 800. Foot support 800 includes a connecting member 802 and a pressure sensor 804.

Figure 51:
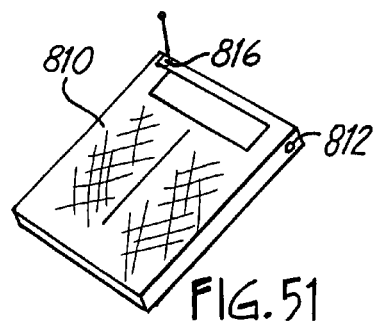
FIG. 51 is a perspective view of a scale modified for use in the performance of closed chain exercises.
Figure 52:
FIG. 52 is a perspective view of a patient performing closed chain exercises with an exercise orthosis around the knee and using a scale of FIG. 51.

As an alternative to using a foot support connected to an orthosis surrounding a joint, the force sensor can be a separate unit. In particular, foot support 800 can be replaced by a scale 810 or the like, as shown in FIGS. 51 and 52. Scale 810 preferably includes a port 812 for connection with a wire 814 to controller 232. Alternatively, scale 810 can include a radio transmitter 816 that transmits measurements to controller 232.

Figure 53:
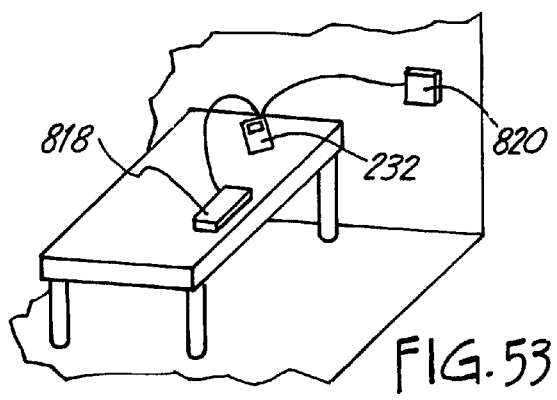
FIG. 53 is a perspective view of two sensors located within a room, the sensors being useful for the performance of closed chain exercises.

If closed chain exercises are to be performed with joints other than the knee, a suitable force sensor can be used. For example, a elbow can be exercised pushing with a hand against a pad sensor 818 on a table or pad sensor 820 against a wall, as shown in FIG. 53. These sensors can be connected to the controller in the same way as scale 810.

A plurality of force sensors can be used for the performance of closed chain exercises. The controller can instruct the patient to vary the respective forces on the two force sensors. For example, two instrumented scales can be used with one scale having forces applied with an injured leg and the second scale having forces applied with an uninjured leg. the patient can be instructed to switch forces between the two legs at a prescribed rate.

A monitor station can be used by the health care professional to plan and monitor the treatment of the patient. Any computer can be used to perform this function. In particular, Windows® based systems are suitable although Unix®, Macintosh®, LINUX®, html-based or JAVA® systems could also be used. The monitor station should have suitable ports for connection with the controller 232.

With any of the additional treatment units including an osteoarthritis support, an abduction/adduction exerciser, a therapeutic cord and a closed chain exercise monitor, as with the instrumented orthosis itself, the display can be used to present various summaries and statistics to the patient. Suitable statistics to be displayed include, for example, exercise times, repetitions, calories expended, and curves where the area under the curve represents work exerted by the patient during an exercise cycle. Similarly, the variance between a target goal and actual performance during an exercise can be displayed.

2. Orthosis Control

The controllers described above preferably are programmed under the control of an appropriate health care professional. Selection of the desired program is described further below. In this section, the monitoring of selected types of treatments using a microprocessor based controller is described.

In one preferred embodiment, the controller has four modes of operation: OFF, STANDBY, ALERT and FULL ON. In the OFF mode, primary and backup battery powers are removed, and no operations are taking place in the controller. In the STANDBY mode, no primary battery power is online, and backup battery power is used to maintain the real time clock and SRAM. Back-up power can be supplied by a coin cell or the like. STANDBY mode is generally used while the primary battery is being replaced or recharged.

In ALERT mode, the real time clock produces a signal at programmed, periodic intervals to activate all on-board electronic components. ALERT-ACTIVE submode has all circuits active. Exercises are generally performed during the ALERT-ACTIVE mode. In ALERT-SLEEP submode, only the real time clock and SRAM memory remain active. ALERT-SLEEP mode is the standard mode of operation between exercise prompts. To allow switching between submodes, primary and backup battery power should be available during the ALERT mode. A beeper function can be used to prompt the patient that an exercise time has been reached.

FULL-ON mode primarily is used during programming and data transfer operations. All on-board electronics and the display are active. FULL-ON mode can be activated automatically when an interface cable is connected.

In a preferred embodiment, the controller can prompt and monitor the performance of isometric exercises, range of motion exercises, proprioception exercises and/or isotonic exercises. When the health care professional programs the controller, the desired exercises from this set are selected along with the associated parameters and timing conditions for the selected exercises. Also, the controller preferably can store two or more sets of exercise routines that can be used in different time intervals relative to the start of rehabilitation. In other words, after a first set of exercise routines have been used for a certain period of time, the controller selects a second, generally more difficult, set of exercises for the patient to perform. These exercises can be performed for any selected joint.

Preferably, the controller prompts the patient at the time for performance of the selected exercises. In some embodiments, the patient presses a key when they are ready to proceed. The display on the monitor can graphically show the patient's motions with suitable coordinates for the particular exercise and compare them with a target, if suitable. The controller can store all of the data points or averages over a set of exercises performed over a period of time. In some embodiments, one button of the controller is a pain button that the patient hits when they feel pain during the exercises. Pain data points from the pressing of the button can be correlated with time, position and activity so that further information for evaluation of the exercise routine is available.

To perform the isometric exercises, the hinge/flexible connector is adjusted to a particular angle. If a manual hinge is used, the hinge is manually adjusted. The controller may instruct the patient if the hinge is set at the desired angle. At the correct angle, the patient applies stress against the fixed hinge in one direction or the other. The controller instructs the patient if the applied stresses are within tolerance values of a target value. The controller preferably prompts the patient regarding the timing of the exercises, including the repetition rate and the amount of time to hold an applied stress. After the selected number of repetitions are performed the exercises are terminated or a new angle of the hinge is selected. The process is repeated until exercises are performed at all of the desired angles.

Figure 54:
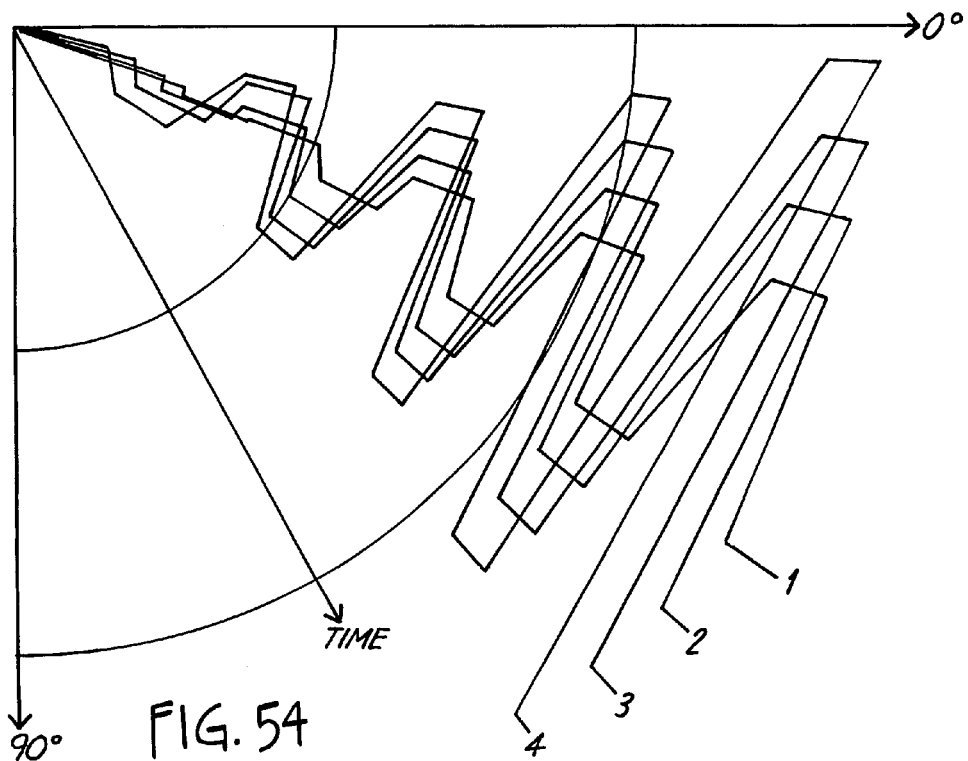
FIG. 54 is a plot of range of motion exercises as measured with an orthosis of the invention.

Improvement in the joint benefits from attention to achieving a desirable range-of-motion (ROM). The ROM can be monitored using the orthosis with a suitable position sensing hinge/flexible connector, as described above. The hinge is set to allow rotation, at least over a portion of the possible rotation range. The performance of ROM exercises is plotted schematically in FIG. 54 using polar coordinates. The angular coordinate represents the angle of the hinge in the orthosis, and the radial coordinate depicts time. Four routines are depicted. These routines could be used for four weeks of exercises or four other suitable time periods. Each higher number routine represents motion over an increased angular range.

Proprioception in this context refers to the patient's sense of position in space, such as the bend of a particular joint. This seeming innate knowledge is a learned phenomenon involving a complex interaction of nerve sensations from sensors that are processed and combined with feedback and correction. A joint has dozens of single-celled measurement sensors: Golgi tendon organs, Paninian-like receptors, Ruffini corpuscles and the like. The brain and spinal cord process the information from these cellular sensors. When a joint is damaged, dozens of sensors may be permanently lost. For example, the anterior cruciate ligament of a knee has over 60 sensor/receptor cells may be lost when the ligament tears. The body makes up for lost receptors by recruiting new sensor information from adjacent places. A new pathway and analysis must be relearned by the nervous system. With a properly designed orthosis this process can be accelerated and enhanced.

In one embodiment, the controller display prompts an action through a graphic display, for example, to get a ball back into a circle, and the patient must react quickly, reflexively with the rehabilitating joint in the orthosis to move the ball on the screen. The position of the ball on the screen is correlated with the position of the joint by way of the position sensor in the orthosis operably connected to the controller. By changing the position of the joint, e.g. knee, the patient can move the ball back into the circle or to another target of some kind. The patient has a limited amount of time to perform the action. As the patient progresses, generally she is given less and less time to respond until the joint has completed recovery. For a joint located on a limb, recovery can be evaluated relative to the joint on the contralateral limb. This exercise can be embedded into a wide variety of game-type environments, where the input comes from the orthosis rather than a joystick or the like. These exercises improve cooperation and coordination. A similar game format can be used to perform isometric exercises where the amount of strain measured by the strain sensor is used to move the cursor.

Figure 55:
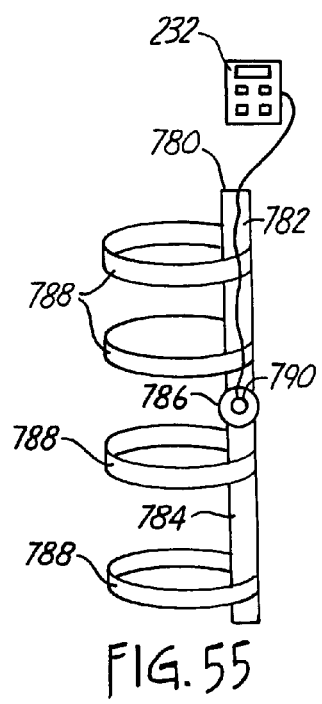
FIG. 55 is a side view of a proprioception brace for performing coordinated proprioception exercises with two limbs.

Because proprioception involves the whole body, a collateral, i.e., uninjured, limb may have significant impact on proprioception performance of the injured limb. It may be advantageous to train the limbs, such as an injured and uninjured leg, together. A simple brace can be placed on the uninjured limb. A suitable proprioception brace 780 is shown in FIG. 55. Brace 780 includes an upper frame member 782 and a lower frame member 784 connected by a hinge 786. Suitable straps 788 or the like can be used to secure brace 780 to the uninjured limb. Straps 788 can attach with hook-and-loop fasteners or other simple fastening system.

Hinge 786 preferably includes a position sensor 790 that can be connected to controller 232. In one application, the patient wearing an instrumented orthosis on the injured limb (e.g., leg) and a proprioception brace on the uninjured limb (e.g., leg) can be instructed to shift forces from one limb to the other with specific timing indicated by motion of an object shown on the screen of the controller. For example, the patient may be instructed to shift weight from one leg to the other in a series of closed chain, i.e., weight bearing, proprioception exercises.

Isotonic exercises are similar to the range-of-motion exercises except that selected resistance is provided in the hinge/flexible connection. Resistance is provided by a manual unit such as resistance unit 300 above or by an electrical resistance hinge actuated by the controller. In any case, a desired amount of resistance is set manually or automatically. The joint is then flexed over a prescribed range-of-motion. Controller can monitor the degree of flexing of the joint using the position sensor and the amount of forces applied during the flexing using the strain sensor. The strain sensor can be calibrated such that a strain reading can be matched with a corresponding torque applied to the hinge. If the instrumented orthosis includes both a strain sensor and a position sensor, the outputs relating to the two different transducers can be displayed with the two dimensional motion on the display of a cursor or the like, with the position in the respective dimensions being determined by the reading of a corresponding transducer.

As noted above, the controller can be attached to a variety of additional devices, such as closed chain exercise units, energy propagating transducers, condyle sensors and the like, to assist with treatment. Generally, the monitoring of the operation of these additional units can be performed with the controller in a straightforward manner. The use of the closed chain exercise units is described in more detail.

The performance of closed chain exercises can be performed in either a static/isometric mode or a dynamic isotonic mode. In the static mode, the patient flexes the knee or other joint to the desired angle and then leans against an opposing surface to apply a desired amount of force. The hinge can be locked or unlocked during the exercises. After performing a programmed number of repetitions, the patient is instructed to move the joint to a different orientation. At the new orientation, the patient again applies force according to a pre-programmed target amount of force. The process is repeated until the exercises are performed at all the selected orientations. Again, the exercise can be incorporated into a variety of game formats, such as a slalom skier, basketball free throws, a road race course, a simple moving bar graph, "Pong," or the like.

Figure 56:
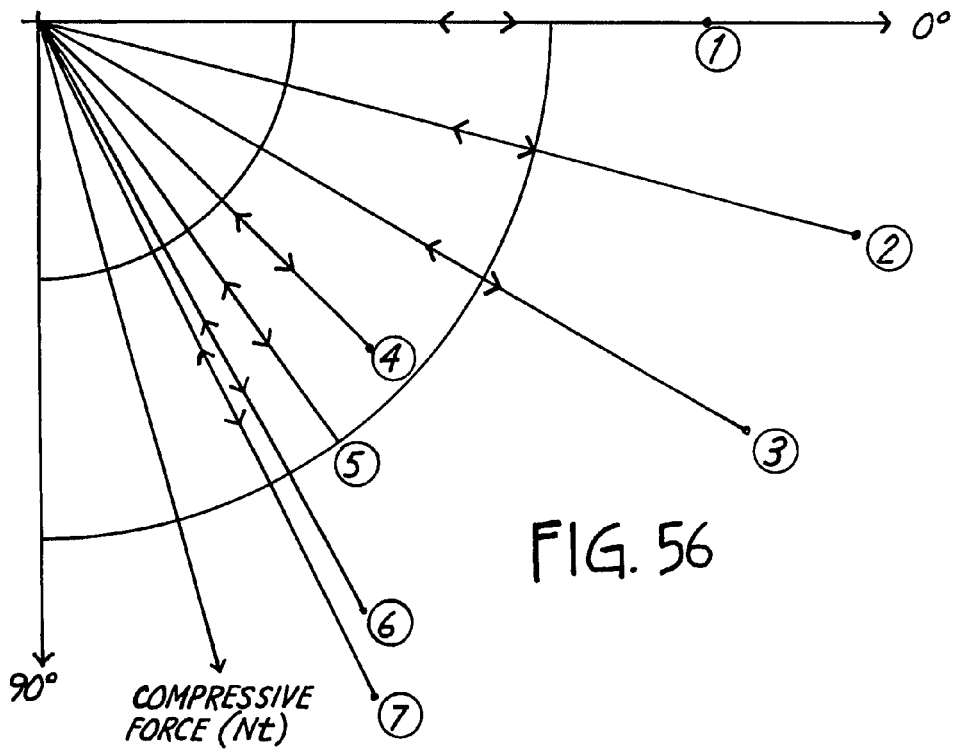
FIG. 56 is a plot of static closed chain exercises as measured with an orthosis of the invention.

This process is depicted schematically in FIG. 56 for the performance of closed chain exercises at 7 different angles. The plot in FIG. 56 is in polar coordinates where the angular coordinate represents the rotation about the hinge and where the radial coordinate is the force applied to the closed chain force sensor. The angle and force can be monitored by the controller and stored for future evaluation. Similarly, the angle and force can be displayed to provide immediate feedback to the patient during the exercises.

To perform dynamic closed chain exercises, the hinge of the orthosis is free to rotate during the exercises. The orthosis is first brought to a particular orientation. Then, a desired amount of force is applied at that orientation for a period of time. While the force is applied against the closed chain force sensor, the hinge is rotated to another selected orientation. At the new orientation, the amount of force applied is changed and held for a particular period of time. Again, the orientation is changed while the force is being applied. The process is repeated according to the programming in the controller. Dynamic closed chain exercises create small but useful and controlled amounts of joint shear.

Figure 57:
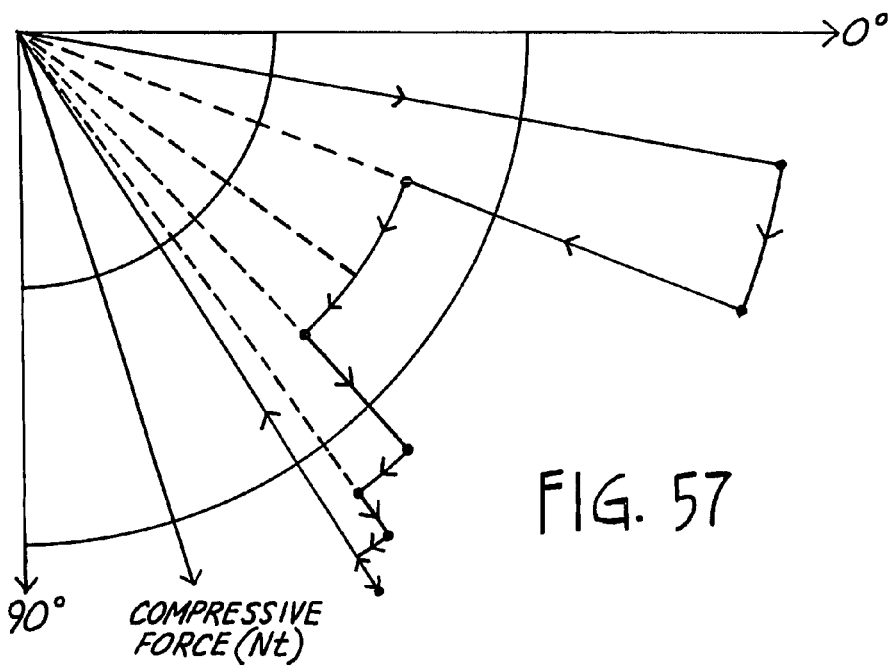
FIG. 57 is a plot of dynamic closed chain exercises performed with an orthosis of the invention.

The procedure for a single dynamic closed chain exercise routine is depicted schematically in FIG. 57 in polar coordinates. The angular coordinate corresponds to the angular orientation of the hinge of the orthosis and the radial coordinate is the amount of force applied to the closed chain force sensor. The arrows indicate changes in applied forces or orientations performed by the patient while the points indicate stop points where forces and orientation are held fixed for a period of time. The entire exercise can be repeated with the same parameters or different parameters according to a prescribed program. Also, the changes in orientation can be reversed such that the patient moves the hinge from larger angles to smaller angles.

The control unit can be programmed to accept other input from the patient. In particular, inquiries can be directed to the patient at the start of an exercise routine, at the end of an exercise routine or at other times. The answers are stored for downloading to a health care professional along with suitable information regarding the performance of programmed exercises. Additional information on the types of inquiries are described further below.

Figure 58:
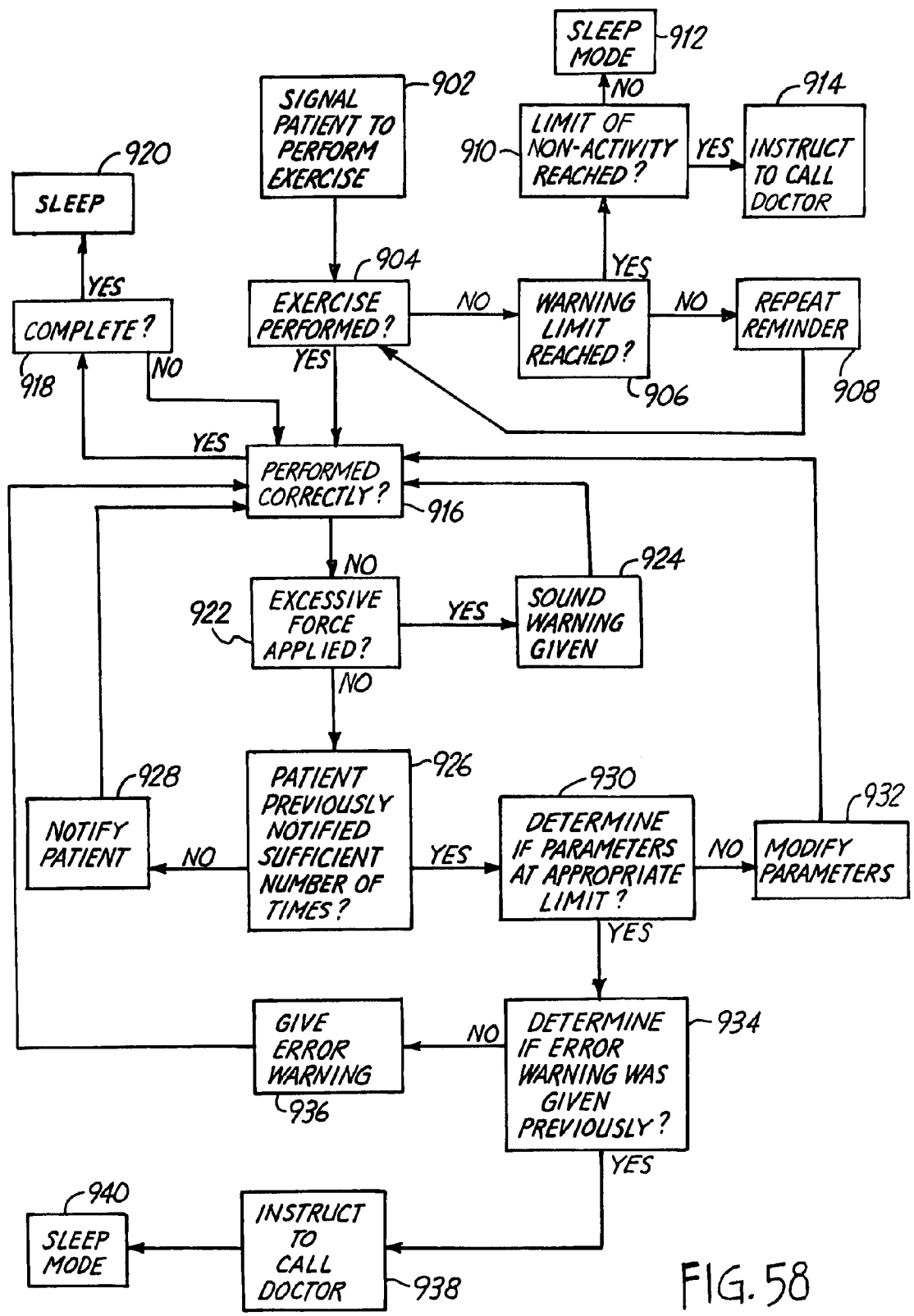
FIG. 58 is a flow diagram showing one embodiment of contingent intervention operation of the controller.
Figure 62:
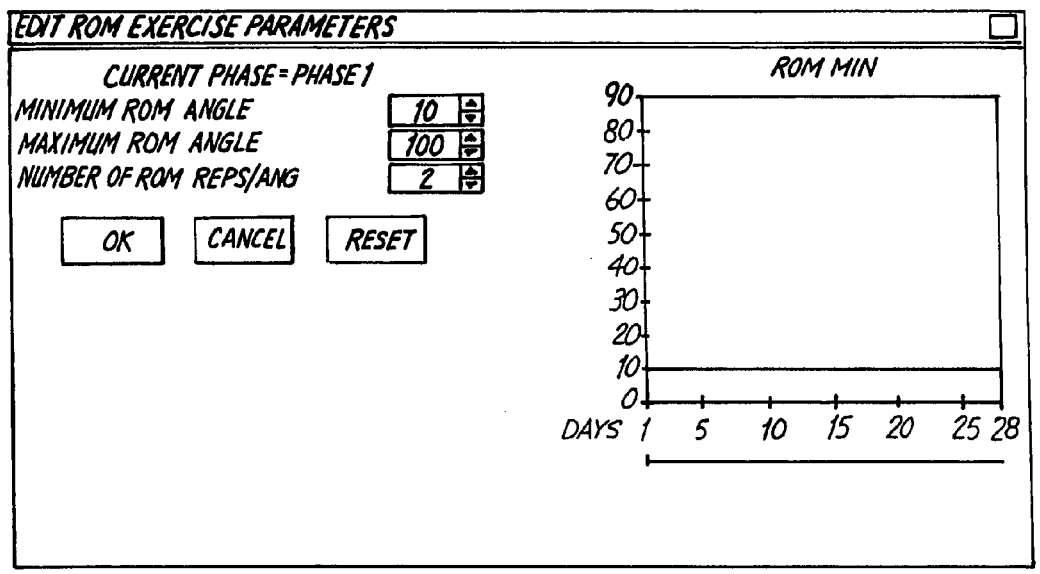
FIG. 62 is a schematic depiction of a computer screen window depicting the entry of range of motion exercise parameters into the monitor station.
Figure 63:
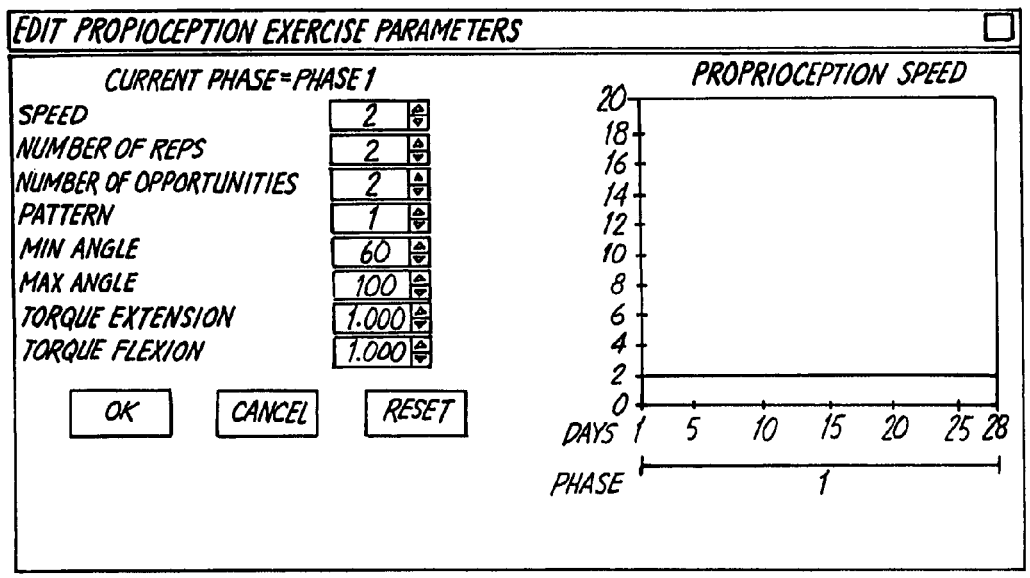
FIG. 63 is a schematic depiction of a computer screen window depicting the entry of proprioception exercise parameters into the monitor station.
Figure 64:
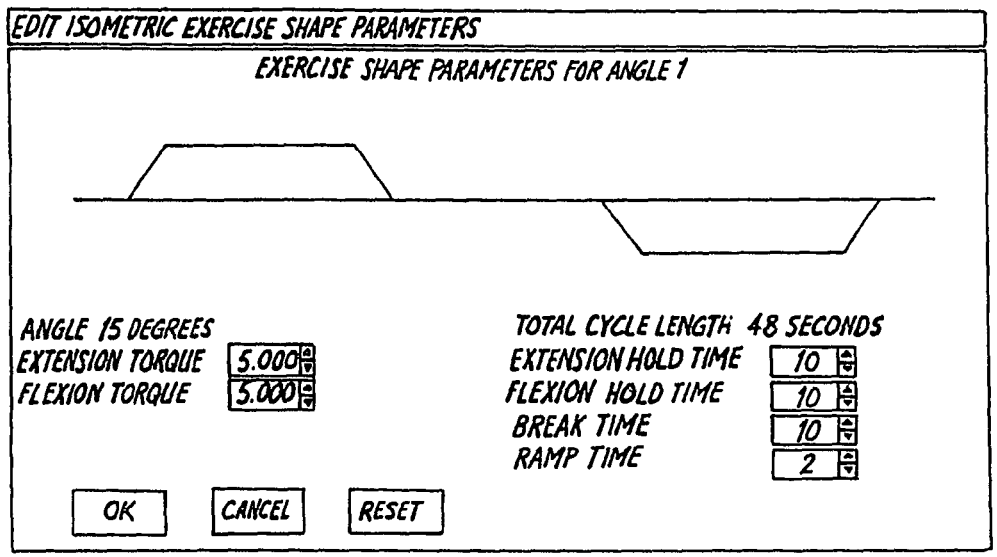
FIG. 64 is a schematic depiction of a computer screen window depicting the entry of isometric exercise shape parameters into the monitor station.

As part of the monitoring operation, the controller preferably, continuously monitors the performance of an exercise to prevent difficulties. On embodiment of this contingency processing is outlined in FIG. 58. The patient is signaled 902 to initiate the performance of exercises. The performance of the exercises is evaluated to determine if exercises are being performed 904. If not, a counter is evaluated to determine if the warning limit has been reached 906. If the warning limit not, the reminder or signal to initiate the exercises is repeated 908, and the evaluation if exercises are being performed 904 is repeated. If the limit on number of warnings has been reached, it is evaluated if the limit of non-activity periods has been reached 910. If the limit of non-activity periods has not been reached, the controller enters sleep mode 912. If the limit of non-activity periods has been reached, the patient is instructed 914 to call the doctor.

If exercises have been started at step 904, the transducer parameters are evaluated to determine if the exercises are being performed 916 within specified parameters. If they are within tolerance ranges, it is evaluated if the exercises are complete 918. If the exercises are complete, the controller enters sleep mode 920. If the exercises are not complete, the evaluation of the performance 916 of the exercises is repeated.

If the exercises are not being performed within tolerance values, the exercises are evaluated to determine if excessive force is being applied 922. If excessive force is being applied, a sound warning is given 924, and the evaluation of the exercises 916 is repeated. If excessive force is not being applied, it is determined 926 if the patient was previously warned a maximum number of time that the exercise is not being performed correctly. If the maximum number of warning has not been given, the patient is notified 928 again, and the evaluation 916 is continued. If the patient has been warned a predetermined number of times previously, the exercise parameters are evaluated to determine 930 if they are at programmed limits. If not, the parameters are modified 932, and the evaluation 916 is repeated. If the parameters are at pre-programmed limits, it is determined 934 if an error warning has previously been given that the parameters are at their limits. If the error warning was not previously given, the warning is given 936, and the monitoring 916 is repeated. If the warning was previously given, the patient is instructed 938 to call the doctor, and the controller enters a sleep mode 940.

Periodically, the information stored by the processor is downloaded to a health care professional. Various methods for downloading the information were described above. In principle, the controller can store all of the information about the performance of particular sets of exercise routines and download all of this information for analysis. Alternatively, the controller can perform some initial data analysis to reduce the amount of data that must be stored and transferred. Thus, raw or analyzed data can be transferred.

The preliminary analysis, if any, performed by the controller can include grouping and/or averaging of groups of exercises over certain periods of time and/or performed at particular times of the day. This analysis can involve an evaluation of variation with the progress of time to assist the health care professional evaluate whether the patient is making sufficient improvement and to evaluate whether the exercise routine programmed into the controller is appropriate. In one embodiment, the controller downloads the date, time, number of repetitions of an exercise, force curves, range-of-motion end stops achieved, number of hits in a proprioception game, and number of times the patient pushed the pain button.

3. Use of Orthosis

To reduce the chance of the patient injuring themselves using the orthoses described herein, the patient preferably is examined by a trained health care professional prior to using the orthosis. Upon evaluating the condition of the patient, the controller is programmed for suitable exercises. In preferred embodiments, the monitor station assists the health care professional (HCP) with the programming process. In particular, the monitor station can lead the programmer through a set of questions to design to type of exercise routine desired. Based on the answers to the questions, the monitor station pieces together the program for the controller. Once the controller is connected to the monitor station by way of an RS 232 connection, a modem connection, a radio connection, an IR connection or other suitable connection using an appropriate protocol, the program is downloaded into the controller.

Generally, the monitor station stores information on a particular patient, so the HCP initially instructs the monitor station whether the patient is a new patient or a continuing patient. Initial questions preferably include patient's age within a set of ranges, patient's sex, joint involved, and type of injury.

In one preferred embodiment, the monitor leads the HCP through a series of screens to fill in information related to the performance of exercises within up to five different time periods, as shown in FIGS. 59-64. The HCP can indicate the number of days that each phase will last. The parameters for each type of exercise to be performed in each phase are then set, see FIGS. 60-64. The monitor can be programmed to suggest exercise routines based on information entered about the patient. The HCP can modify the suggested routines as desired.

Additional screens can be used to provide additional input regarding additional treatment add ons and/or information regarding the controller and the means for communicating with the controller. Once the HCP has completed the specification of the exercise routine, the controller is connected to the monitor station and the controller is programmed with the exercise routine.

At prescribed periods of time, information stored in the controller regarding the performance of the exercises by the patient can be downloaded into the monitor station. The time interval can be determined based on the storage capacity of the controller, the suitable length for evaluation of progress by HCP or other similar issues. The download of information from the controller to the monitor station can be performed at the health care facility where the monitor station is located or at a remote location. If performed at the health care facility, the information can be downloaded by direct hook up of the controller with the monitor station or through a modem, radio connection, infrared connection or the like. Remote hook up can be performed with a modem connection, radio communication or other longer range connection including, for example, the internet.

Figure 65:
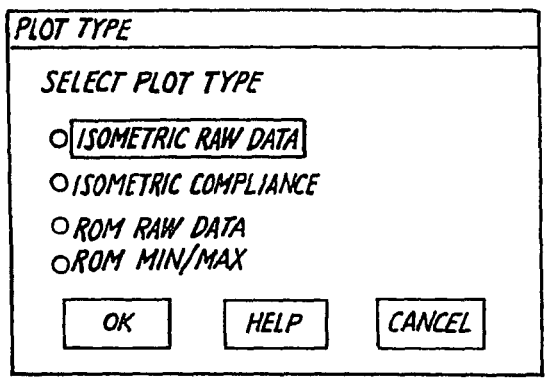
FIG. 65 is a schematic depiction of a computer screen window requesting entry of an instruction related to the plot of downloaded exercise data.
Figure 66:
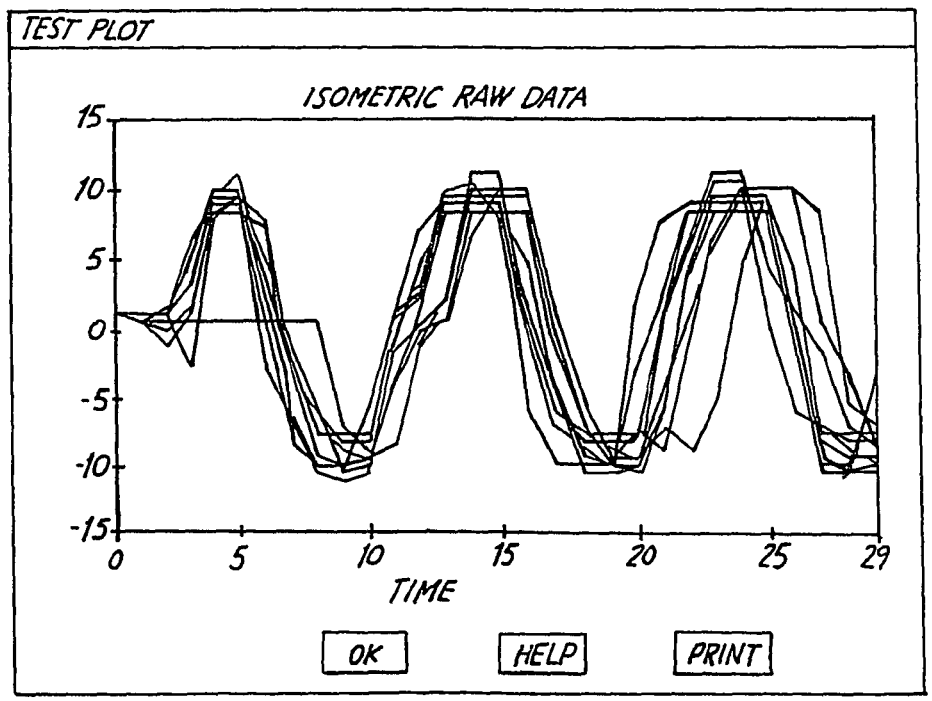
FIG. 66 is a schematic depiction of the plot of raw data on the performance of isometric exercises on a monitor station screen.

Suitable analysis is performed of the data. for example, the downloaded data on the exercises can be plotted in raw form or following some form of data averaging or selection. Examples are shown in FIGS. 65-66. Based on an evaluation of the downloaded data, the HCP can maintain the exercise program in its initially programmed form or modify the exercise program to account for unexpected developments. In preferred embodiments, the HCP can reprogram the controller remotely such that any desired changes in the routine can be made without the patient needing to visit the health care facility.

To facilitate the monitoring function, real time telecommunication can be performed such that information on the exercises can be received by the health care professional as the exercises are being performed. Similarly, the patient and health care professional can exchange communications in real time. Real time telecommunications can involve teleconferencing or videoconferencing. In addition, the patient and/or health care professional can interface with a web site to access or maintain data base information and or as a communication portal. Additional information on these remote monitoring approaches is provided in U.S. patent application Ser. No. 09/266,866 to Oyen et al., entitled REMOTE MONITORING OF AN INSTRUMENTED ORTHOSIS," incorporated herein by reference.

One of several important functions of a microprocessor controlled orthosis is to monitor compliance with performance of exercises. A useful adjunct to the compliance monitoring function can be achieved by performing a psychological evaluation of the patient. The psychological test can be used to evaluate the suitability of the programmed exercises as well as indicate other potential problems with the healing process not directly linked to the exercises.

A relatively simple form of the psychological test can involve questions for the patient prior to the performance of the exercises regarding the patient's readiness to perform the exercises and after the exercises regarding the usefulness of the exercises. The inquiries can take the form of selecting from a selection of a representative graphical representations, such as a happy face, a frowning face etc. A more sophisticated test can involve questions regarding pain being felt by the patient. One systematic set of questions regarding pain have been developed at McGill University and are known as the McGill Pain Questionnaire. The questions relate to the degree of pain, the location of pain, changes in pain and the sensation of pain. The answers can be presented as numerical values that are scored according to a prescribed formula. A further description of the McGill Pain Questionnaire is described in R. Melzack, "The McGill Pain Questionnaire: Major Properties and Scoring Methods," Pain 1:277-299 (1975), incorporated herein by reference. The questionnaire can be updated and modified as appropriate.

The psychological test can be used as part of the evaluation of the patient. In particular, the exercise routine can be modified in response partly to the to mental attitude of the patient to help assure further compliance with the exercises and to increase the comfort level of the patient. The balance of all of these factors can lead to faster rehabilitation of the patient. Additional description of the use of psychological evaluation as an adjunct to orthopedic treatment is provided in U.S. patent application Ser. No. 09/339,071 to Stark et al., entitled "REHABILITATIVE ORTHOSES," incorporated herein by reference.

The embodiments described above are intended to be exemplary and not limiting. Further embodiments are within the claims below. Although the present invention has been described with reference to preferred embodiments, workers skilled in the art will recognize that changes may be made in form and detail without departing from the spirit and scope of the invention.

What is claimed is:

1. A portable controller comprising:
   a keypad;
   a display;
   a communications port in communication with a remote health care facility through a communications channel, the communications port in communication with a sensor ambulatory with a patient that makes measurements of a physiological parameter of the patient; and
   a computer processor communicatively coupled to the display and the sensor, the processor configured to:
   prompt the patient to perform exercises in the form of a video game, the exercises selected by the computer processor from one of at least two sets of exercise routines programmed into the computer processor, the selection based upon the time elapsed since the start of a rehabilitation period,
   send signals to the display that cause the display to show an object of the video game at a location on the display, the location the object is displayed at is a function of a signal received from the sensor, the signal received from the sensor is received in response to the patient attempting to perform the exercises,
   present inquiries on the display and receive answers on the keypad,
   correlate the answers and the measured physiological parameter of the patient with a time period, and
   transmit the answers and measured physiological parameter over the communications channel to the remote health care facility,
   wherein the inquiries comprise questions related to mental attitude of the patient; and
   wherein the processor is configured to be reprogrammable at a location remote from the controller.

2. The portable controller of claim 1 wherein the communications port comprises a modem.

3. The portable controller of claim 1 wherein the communications port comprises a radio transmitter.

4. The portable controller of claim 1 wherein a question relates to a degree of pain.

5. The portable controller of claim 1 wherein a question relates to a location of pain.

6. The portable controller of claim 1 wherein a question relates to a change in pain.

7. The portable controller of claim 1 wherein additional questions relate to the prompted exercises, the prompted exercises being monitored using the controller based on the physiological parameter.

8. The portable controller of claim 1 wherein the exercises relate to proprioception.

9. The portable controller of claim 1 wherein the exercises relate to isometric exercises.

10. The portable controller of claim 1 wherein the exercises are performed using an orthotic structure secured to the patient and wherein the exercises are monitored using a transducer associated with the orthotic structure.

11. The portable controller of claim 10 wherein the monitored exercise involves range-of-motion.

12. The portable controller of claim 10 wherein the monitored exercises involve closed chain exercises.

13. The portable controller of claim 1 wherein the controller stores exercise routines and the controller displays the patient's performance in comparison with a target performance.

14. The portable controller of claim 1 wherein the controller warns the patient if excessive force is applied.

15. The portable controller of claim 1 wherein the controller downloads information to the remote health care facility.

16. A portable controller comprising:
   a keypad;
   a display;
   a communications port in communication with a remote health care facility through a communications channel, the communications port in communication with a treatment device ambulatory with the patient, the treatment device including a sensor; and
   a computer processor communicatively coupled to the display and the sensor, that is the processor configured to:
   prompt the patient to perform exercises in the form a video game, the exercises selected by the computer processor from one of at least two sets of exercise routines programmed into the computer processor, the selection based upon the time elapsed since the start of a rehabilitation period,
   send signals to the display that cause the display to show an object of the video game at a location on the display, the location the object is displayed at is a function of a signal received from the sensor, the signal received from the sensor is received in response to the patient attempting to perform the exercises,
   monitor the performance of the exercises by the patient,
   present inquiries on the display and receive answers on the keypad,
   correlate the answers and the performance of the exercises by the patient with a time period, and
   transmit the answers over the communications channel to the remote health care facility,
   wherein the inquiries comprise questions related to mental attitude of the patient, and
   wherein the processor is configured to be reprogrammable at a location remote from the controller to alter the treatment received by the patient.

17. The portable controller of claim 16 wherein a question relates to a change in pain.

18. The portable controller of claim 16 wherein additional questions relate to exercises that are also monitored using the controller.

19. The portable controller of claim 16 wherein the exercises are performed using an orthotic structure secured to the patient and wherein the sensor is associated with the orthotic structure, and the exercises are monitored using the sensor associated with the orthotic structure.

* * * * *

UNITED STATES PATENT AND TRADEMARK OFFICE
CERTIFICATE OF CORRECTION

| | | |
|---|---|---|
| PATENT NO. | : 8,678,979 B2 | Page 1 of 1 |
| APPLICATION NO. | : 11/714669 | |
| DATED | : March 25, 2014 | |
| INVENTOR(S) | : Stark et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 650 days.

Signed and Sealed this
Eleventh Day of August, 2015

Michelle K. Lee
*Director of the United States Patent and Trademark Office*